(12) United States Patent
Singamaneni et al.

(10) Patent No.: US 11,813,056 B2
(45) Date of Patent: Nov. 14, 2023

(54) MATERIALS AND METHODS FOR IMPLEMENTING IMMUNOASSAY ON MICRONEEDLE PATCH FOR DETECTION AND QUANTIFICATION OF BIOANALYTES IN INTERSTITIAL FLUID

(71) Applicant: Washington University, St. Louis, MO (US)

(72) Inventors: Srikanth Singamaneni, St. Louis, MO (US); Zheyu Wang, St. Louis, MO (US); Jingyi Luan, St. Louis, MO (US)

(73) Assignee: Washington University, St. Louis, MO (US)

( * ) Notice: Subject to any disclaimer, the term of this patent is extended or adjusted under 35 U.S.C. 154(b) by 596 days.

(21) Appl. No.: 16/943,157

(22) Filed: Jul. 30, 2020

(65) Prior Publication Data
US 2021/0033604 A1   Feb. 4, 2021

Related U.S. Application Data

(60) Provisional application No. 62/880,973, filed on Jul. 31, 2019.

(51) Int. Cl.
*A61B 5/145*   (2006.01)
*A61M 37/00*   (2006.01)
(Continued)

(52) U.S. Cl.
CPC ........ *A61B 5/14514* (2013.01); *A61K 9/0021* (2013.01); *A61M 37/0015* (2013.01); *G01N 33/5306* (2013.01); *G01N 33/54386* (2013.01); *G01N 33/6869* (2013.01); *A61M 2037/0061* (2013.01)

(58) Field of Classification Search
CPC ......... G01N 33/54386; G01N 33/5306; G01N 33/6869; G01N 2333/5412; G01N 33/54366; A61B 5/14514; A61B 5/6851; A61K 9/0021; A61M 37/0015; A61M 2037/0061; A61M 2037/0023; A61M 2037/003; A61M 2037/0038; A61M 2037/0046; A61M 2037/0053
See application file for complete search history.

(56) References Cited

U.S. PATENT DOCUMENTS

| | | | |
|---|---|---|---|
| 6,334,856 B1* | 1/2002 | Allen | A61K 9/0021 216/75 |
| 2003/0199811 A1* | 10/2003 | Sage, Jr. | A61B 17/54 606/186 |
| 2011/0212485 A1* | 9/2011 | Mitragotri | A61B 10/0283 435/325 |

OTHER PUBLICATIONS

Bodenlenz et al., Open flow microperfusion as a dermal pharmacokinetic approach to evaluate topical bioequivalence. Clinical pharmacokinetics, 2017, 56 (1), pp. 91-98.
(Continued)

*Primary Examiner* — Amber R Stiles
(74) *Attorney, Agent, or Firm* — Armstrong Teasdale LLP

(57) ABSTRACT

The present disclosure is directed to microneedle patches for direct sampling and ultrasensitive detection of protein biomarkers in dermal interstitial fluids. The microneedle patches are comprised of polymers with high protein absorption capability (e.g. polystyrene) and are modified with capture biorecognition elements that are specific to target analytes in the interstitial fluid (ISF). Systems and methods are further provided for detection of a target ISF analyte obtained by in vivo sampling of the ISF using a microneedle patch.

20 Claims, 73 Drawing Sheets

(51) Int. Cl.
G01N 33/543 (2006.01)
G01N 33/68 (2006.01)
G01N 33/53 (2006.01)
A61K 9/00 (2006.01)

(56) References Cited

OTHER PUBLICATIONS

Bonnet et al., Special Issue on Bone Disease Mechanisms: Periostin action in bone. Molecular and Cellular Endocrinology, 2016, 432, pp. 75-82.
Cai et al., Magnet Patterned Superparamagnetic Fe3O4/Au Core-Shell Nanoplasmonic Sensing Array for Label-Free High Throughput Cytokine Immunoassay, Advanced Healthcare Materials, 2019, 8 (4), 1801478, 23 pages.
Chang et al., A swellable microneedle patch to rapidly extract skin interstitial fluid for timely metabolic analysis. Advanced Materials, 2017, 29 (37), 1702243, 8 pages.
Coffey et al., Dynamic application of microprojection arrays to skin induces circulating protein extravasation for enhanced biomarker capture and detection. Biomaterials, 2016, 84, pp. 130-143.
Coffey et al., Rapid and selective sampling of IgG from skin in less than 1 min using a high surface area wearable immunoassay patch. Biomaterials, 2018, 170, pp. 49-57.
Colnot, Skeletal cell fate decisions within periosteum and bone marrow during bone regeneration. Journal of Bone and Mineral Research, 2009, 24 (2), pp. 274-282.
Copeland et al.pp. , Acute inflammatory response to endotoxin in mice and humans. Clin. Diagn. Lab. Immunol., 2005, 12 (1), pp. 60-67.
Davis et al., Insertion of microneedles into skin: measurement and prediction of insertion force and needle fracture force. Journal of biomechanics, 2004, 37 (8), pp. 1155-1163.
Dulkeith et al., Gold nanoparticles quench fluorescence by phase induced radiative rate suppression. Nano letters, 2005, 5 (4), pp. 585-589.
Dwek, The periosteum: what is it, where is it, and what mimics it in its absence? Skeletal radiology, 2010, 39 (4), pp. 319-323.
Gole et al., Azide-derivatized gold nanorods: functional materials for "click" chemistry. Langmuir, 2008, 24 (1), pp. 266-272.
Gromov et al., Tumor interstitial fluid—A treasure trove of cancer biomarkers. Biochimica et Biophysica Acta (BBA)- Proteins and Proteomics, 2013, 1834 (11), pp. 2259-2270.
He et al., A Hydrogel Microneedle Patch for Point-of-Care Testing Based on Skin Interstitial Fluid. Advanced Healthcare Materials, 2020, 9 (4), 1901201, 11 pages.
Heikenfeld et al., Accessing analytes in biofluids for peripheral biochemical monitoring. Nature biotechnology, 2019, 37 (4), pp. 407-419.
Hong et al., Ethyl acetate extracts of alfalfa (*Medicago sativa* L.) sprouts inhibit lipopolysaccharide-induced inflammation in vitro and in vivo. Journal of biomedical science, 2009, 16:64, 12 pages.
Hu et al., Gold nanostructures: engineering their plasmonic properties for biomedical applications. Chemical Society Reviews, 2006, 35 (11), pp. 1084-1094.
Kampman, The treatment of cocaine use disorder. Science advances, 2019, 5 (10), eaax1532, 8 pages.
Kiistala, Suction blister device for separation of viable epidermis from dermis. J Invest Dermatol, 1968, 50, pp. 129-137.
Kinsey et al., Anti-cocaine vaccine development. Expert review of vaccines, 2010, 9 (9), pp. 1109-1114.
Kool et al., Suction blister fluid as potential body fluid for biomarker proteins. Proteomics 2007, 7 (20), pp. 3638-3650.
Krogstad et al., Microdialysis methodology for the measurement of dermal interstitial fluid in humans. British Journal of Dermatology, 1996, 134 (6), pp. 1005-1012.
Kyutoku et al., Role of periostin in cancer progression and metastasis: inhibition of breast cancer progression and metastasis by anti-periostin antibody in a murine model. International journal of molecular medicine, 2011, 28 (2), pp. 181-186.
Lee et al., Dependence of the Enhanced Optical Scattering Efficiency Relative to That of Absorption for Gold Metal Nanorods on Aspect Ratio, Size, End-Cap Shape, and Medium Refractive Index. J. Phys. Chem. B, 2005, 109, pp. 20331-20338.
Luan et al., Ultrabright fluorescent nanoscale labels for the femtomolar detection of analytes with standard bioassays, Nature Biomedical Engineering, 2020, 4 (5), pp. 518-530.
Martell et al., Cocaine vaccine for the treatment of cocaine dependence: a randomized double-blind placebo-controlled efficacy trial. Arch Gen Psych, 2009, 66, pp. 1116-1123.
Merle et al., The multiple facets of periostin in bone metabolism. Osteoporosis International, 2012, 23 (4), pp. 1199-1212.
Moore et al., Periosteal thickness and cellularity in mid-diaphyseal cross-sections from human femora and tibiae of aged donors. Journal of anatomy, 2014, 224 (2), pp. 142-149.
Muller et al., Surface modified microprojection arrays for the selective extraction of the dengue virus NS1 protein as a marker for disease. Analytical chemistry, 2012, 84 (7), pp. 3262-3268.
Muller et al., A comparative proteomic study of human skin suction blister fluid from healthy individuals using immunodepletion and iTRAQ labeling. Journal of proteome research, 2012, 11 (7), pp. 3715-3727.
Nedrebø et al., Differential cytokine response in interstitial fluid in skin and serum during experimental inflammation in rats. The Journal of physiology, 2004, 556 (1), pp. 193-202.
Sakai et al., Remodeling of actin cytoskeleton in mouse periosteal cells under mechanical loading induces periosteal cell proliferation during bone formation. PLOS One, 2011, 6 (9), 11 pages.
Samant et al., Mechanisms of sampling interstitial fluid from skin using a microneedle patch. Proceedings of the National Academy of Sciences, 2018, 115 (18), pp. 4583-4588.
Scott et al., Overcoming immune dysregulation with immunoengineered nanobiomaterials. Annual review of biomedical engineering, 2017, 19, pp. 57-84.
Shorter et al., Novel pharmacotherapeutic treatments for cocaine addiction. BMC medicine 2011, 9:119, 9 pages.
Taylor et al., Hapten-specific naive B cells are biomarkers of vaccine efficacy against drugs of abuse. Journal of immunological methods, 2014, 405, pp. 74-86.
Taylor et al., Minimally-invasive, microneedle-array extraction of interstitial fluid for comprehensive biomedical applications: transcriptomics, proteomics, metabolomics, exosome research, and biomarker identification. Laboratory animals, 2018, 52 (5), pp. 526-530.
Tebbe et al., Colloidally stable and surfactant-free protein-coated gold nanorods in biological media. ACS applied materials & interfaces, 2015, 7 (10), pp. 5984-5991.
Tran et al., Proteomic characterization of dermal interstitial fluid extracted using a novel microneedle-assisted technique. Journal of proteome research, 2018, 17 (1), pp. 479-485.
Wang et al., Transdermal colorimetric patch for hyperglycemia sensing in diabetic mice. Biomaterials, 2020, 119782, 20 pages.
Yan et al., Circulating periostin levels increase in association with bone density loss and healing progression during the early phase of hip fracture in Chinese older women. Osteoporosis International, 2017, 28 (8), pp. 2335-2341.
Zhang et al., Encoded Microneedle Arrays for Detection of Skin Interstitial Fluid Biomarkers. Advanced Materials, 2019, 31 (37), 201902825, 8 pages.

\* cited by examiner

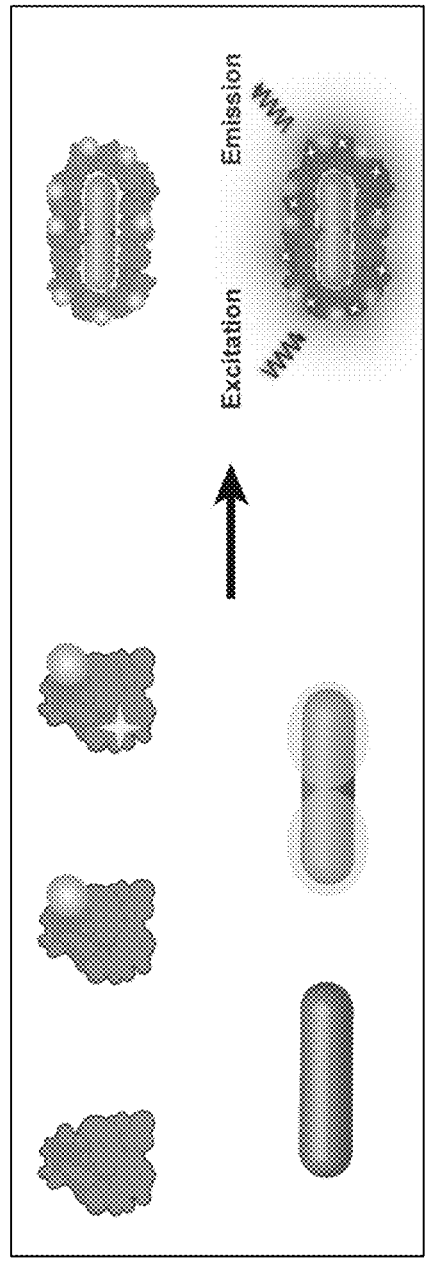
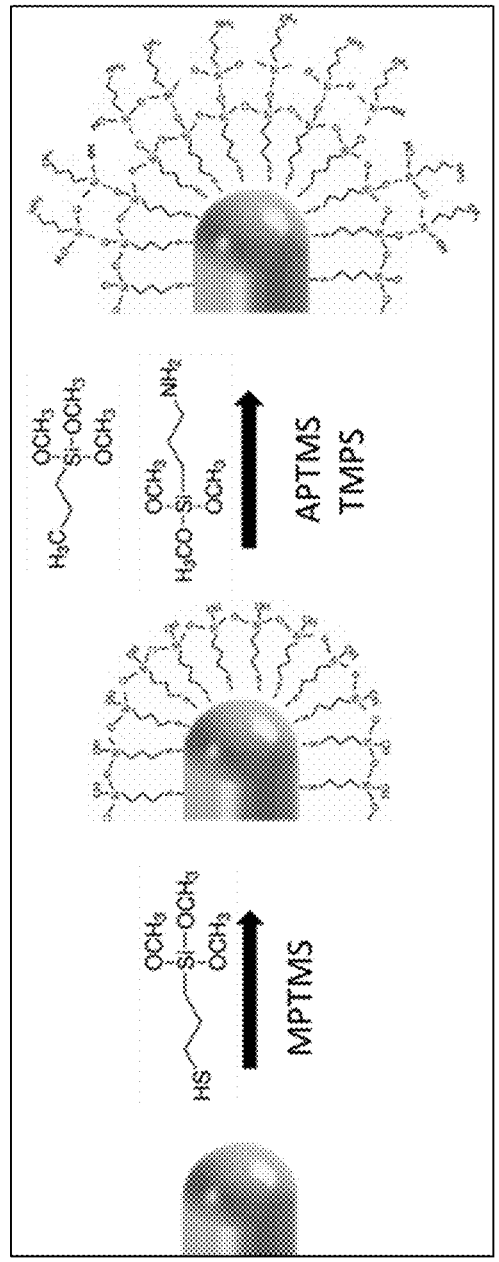
FIG. 19A
FIG. 19B

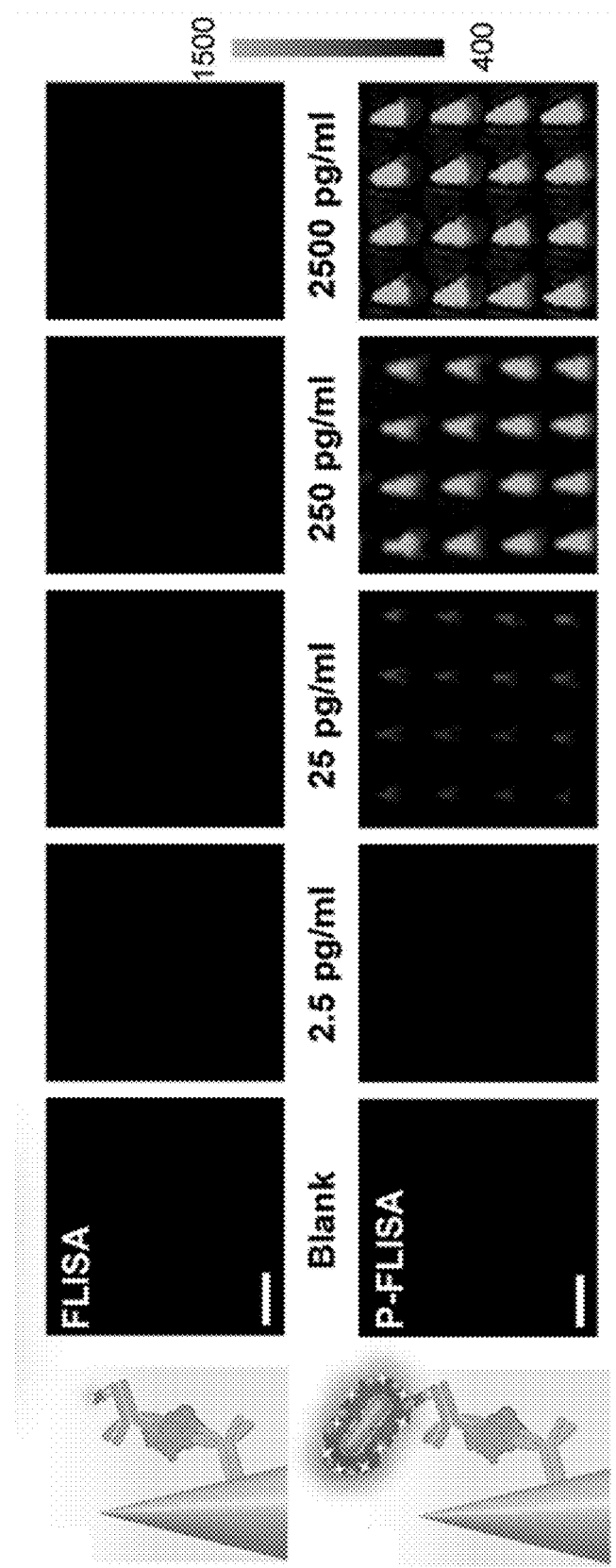

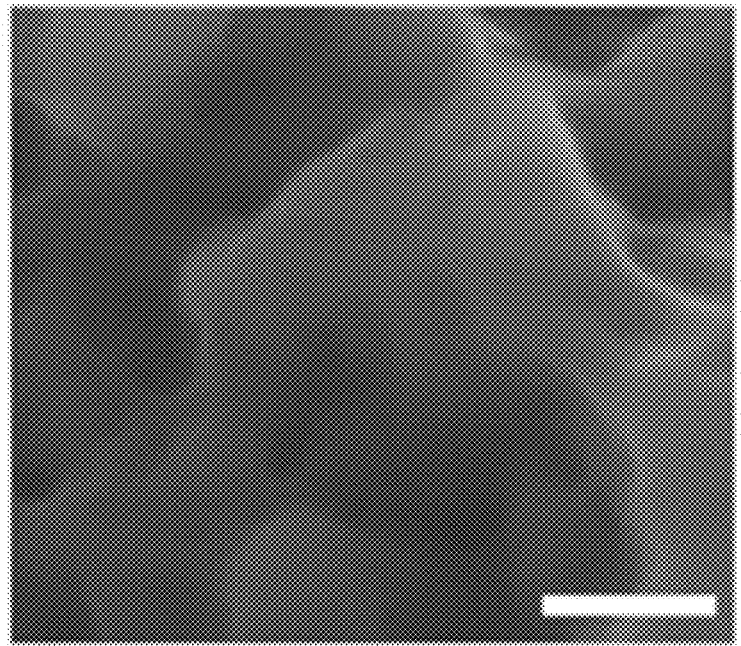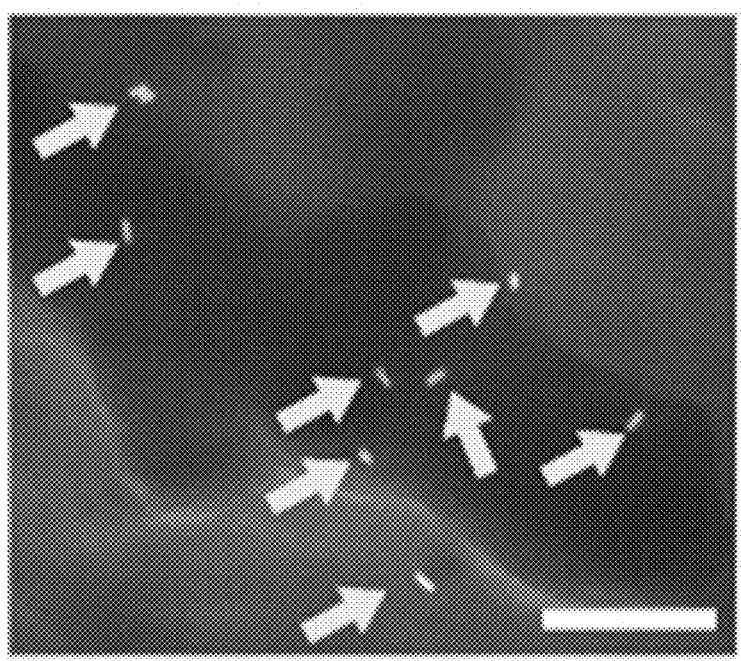
FIG. 32

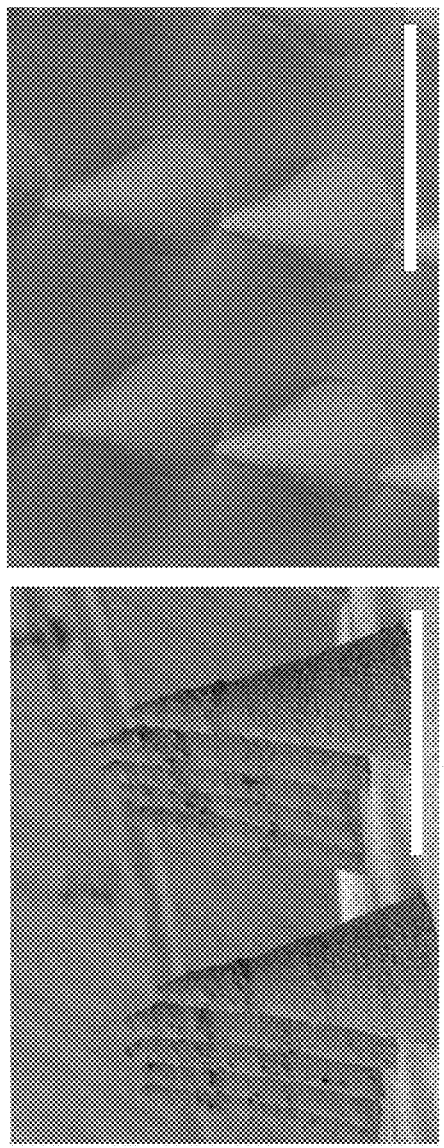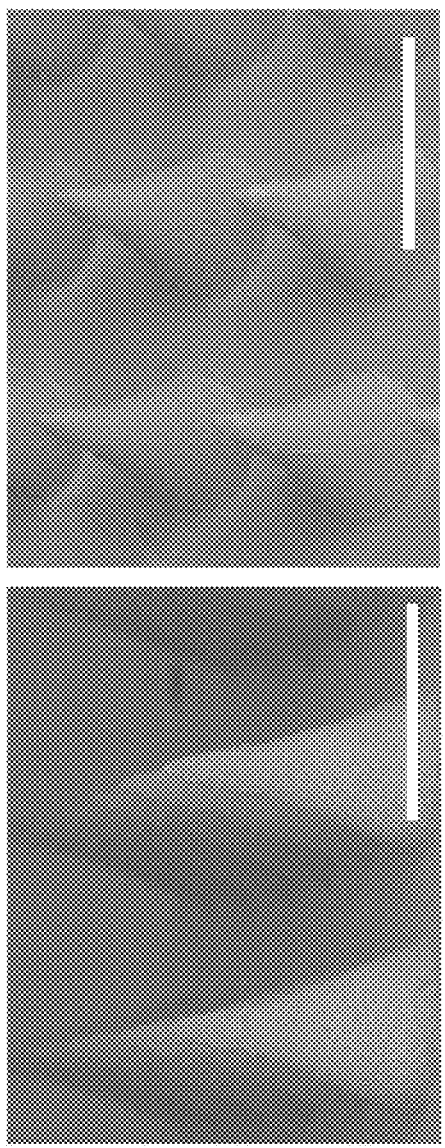
FIG. 45B    FIG. 45D
FIG. 45A    FIG. 45C

US 11,813,056 B2

MATERIALS AND METHODS FOR IMPLEMENTING IMMUNOASSAY ON MICRONEEDLE PATCH FOR DETECTION AND QUANTIFICATION OF BIOANALYTES IN INTERSTITIAL FLUID

CROSS-REFERENCE TO RELATED APPLICATIONS

This application claims priority to U.S. Provisional Application No. 62/880,973, filed Jul. 31, 2019, the content of which is incorporated herein by reference in its entirety.

GOVERNMENT SUPPORT CLAUSE

This invention was made with government support under DE027098 and CA141521 awarded by the National Institutes of Health and under 1900277 awarded by the National Science Foundation. The government has certain rights in the invention.

FIELD OF THE DISCLOSURE

The present disclosure is generally directed to a "microneedle patch" for direct sampling and ultrasensitive detection of protein biomarkers in dermal interstitial fluid. More specifically, the present disclosure is directed to microneedle patches comprised of polymers with high protein absorption capability (e.g., polystyrene) and modified with capture biorecognition elements (e.g., capture antibodies) that are specific to target analytes in the interstitial fluid (ISF).

BACKGROUND OF THE DISCLOSURE

Interstitial fluid, among various peripheral biofluids such as saliva, sweat, and tears, is a particularly rich source of soluble bioanalytes including proteins, peptides, metabolites and nucleic acids, which exhibits close correlation with blood. It also represents the loco-regional biomolecular composition of specific tissues of interest, such as within the tumor microenvironment. Simple and effective methods that enable comprehensive analysis of ISF can lead to transformative advances in novel biodiagnostic technologies that are not only minimally-invasive and pain-free, but also ideally suited for point-of-care (POC) and resource-limited settings. Extraction of ISF followed by ex vivo analysis has not been widely embraced in both pre-clinical and clinical applications due largely to (i) difficulty in extracting ISF, which is time-consuming and requires bulky instruments; and (ii) the extremely small amount of ISF that can be extracted using current technology, making comprehensive analysis challenging. Voltage application from iontophoresis ISF withdrawal might cause irritation over the long term. ISF withdrawal by vacuum suction is cumbersome due to the size of the machine, sample collection may be adversely affected by sweat, and strong suction may alter analyte concentration. For example, microneedle-assisted extraction of ISF (FIG. 1) yields only about 3-5 μL of sample volume (e.g., only about 2 μL of biofluid from 4 cm² of human skin even after 20 minutes of vacuum suction) which is simply insufficient for comprehensive proteomic and metabolomic analysis as sensors must be bathed in ISF. In fact, in pre-clinical settings (e.g., small animal models), to measure the concentration of target biomarkers, pooling an adequate amount of ISF from multiple subjects is common, which inevitably masks the subject-to-subject biological variability.

BRIEF DESCRIPTION OF THE DISCLOSURE

In one aspect, a bilayered microneedle patch is disclosed. The bilayered microneedle patch comprises: a magnetic backing layer; and a microneedle layer attached to the magnetic backing layer, wherein the microneedle layer comprises an array of microneedles.

In another aspect, an assay for detection of a target interstitial fluid (ISF) analyte is disclosed. The assay comprises: a microneedle patch comprising a magnetic backing layer and a microneedle layer attached to the magnetic backing layer, wherein the microneedle layer comprises an array of microneedles coated with a plurality of capture biorecognition elements; a plurality of detection biorecognition elements; and a plurality of fluorescent labels comprising a plasmonic-fluor.

In yet another aspect, a method for detecting a target interstitial fluid (ISF) analyte is disclosed. The method comprises: administering a microneedle patch to penetrate a dermal layer of a subject and sample the ISF of the subject, wherein the microneedle patch comprises a magnetic backing layer and a microneedle layer attached to the magnetic backing layer, wherein the microneedle layer comprises an array of microneedles coated with a plurality of capture biorecognition elements; removing the microneedle patch from the dermal layer of the subject; adding a plurality of detection biorecognition elements to the microneedle patch; adding a plurality of fluorescent labels to the microneedle patch, wherein each of the plurality of fluorescent labels comprises a plasmonic-fluor; and detecting the target ISF analyte based on a fluorescence signal from the plasmonic-fluor.

DESCRIPTION OF DRAWINGS

The drawings described below illustrate various aspects of the disclosure.

FIG. 19A is an exemplary embodiment of a schematic illustration showing the synthesis of a plasmonic-fluor in accordance with the present disclosure. FIG. 19B is an exemplary embodiment of a schematic illustration showing the formation of poly-siloxane layer on the AuNR as the spacer layer in accordance with the present disclosure.

FIG. 25 is an exemplary embodiment of a fluorophore-linked immunosorbent assay (FLISA) at various analyte concentrations in accordance with the present disclosure. Scale bar 500 mm.

FIG. 26 is an exemplary embodiment of a p-FLISA at various analyte concentrations, scale bar 500 mm, in accordance with the present disclosure.

FIG. 32 is an exemplary embodiment of representative SEM images showing pristine microneedle (top) and after being probed by plasmonic-fluor on microneedle (bottom), plasmonic-fluors indicated by arrows in accordance with the present disclosure. Scale bar 500 nm.

FIG. 45A is an exemplary embodiment of a side view SEM image depicting microneedle conical shape and sharp tips before administration of the microneedle patch in accordance with the present disclosure. FIG. 45B is an exemplary embodiment of a top view SEM image depicting microneedle conical shape and sharp tips before administration of the microneedle patch in accordance with the present disclosure. FIG. 45C is an exemplary embodiment of a side view SEM image depicting that the microneedles maintained their conical shape and sharp tips after administration of the microneedle patch on the mouse ventral skin in accordance with the present disclosure. FIG. 45D is an exemplary embodiment of a top view SEM image depicting that the microneedles maintained their conical shape and sharp tips after administration of the microneedle patch on the mouse ventral skin in accordance with the present disclosure. Scale bar, 500 μm.

DETAILED DESCRIPTION OF THE DISCLOSURE

Figure 1:
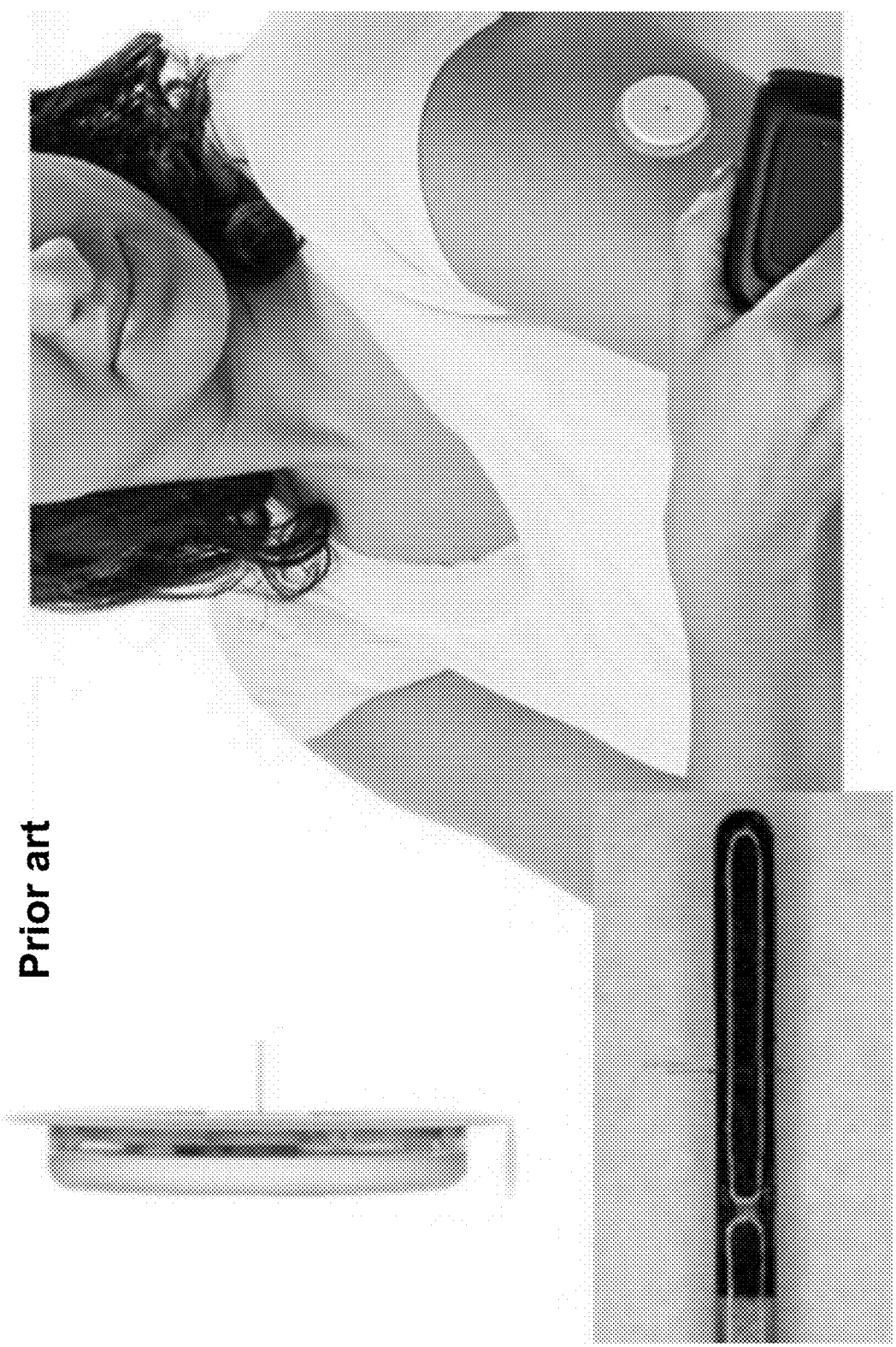
FIG. 1 is an exemplary embodiment of a prior art microneedle-assisted extraction of ISF.

Detection and quantification of protein biomarkers in interstitial fluid (ISF) is informative but remains challenging. In contrast to ISF extraction, microneedles functionalized with biorecognition elements specifically capture target biomarkers in ISF, followed by ex vivo analysis. Direct exposure of microneedles to ISF allows the biorecognition elements on the microneedles to capture target biomarkers in situ, thus offering a promising technology for simple and efficient biodetection. However, physiological concentration of the protein biomarkers in the ISF is usually lower when compared to that in blood. Moreover, analyte-antibody binding kinetics are significantly deteriorated due to the "dense" tissue environment, which results in slower diffusion of target biomolecules to the sensor surface (i.e. microneedle surface), further lowering the probability of analyte capture and consequent signal intensity corresponding to the analyte. These challenges exacerbate the difficulty in detection of protein biomarkers in interstitial fluid. Hence, previous reports are limited to mice that have been intravenously injected with high concentrations of recombinant target markers as pseudo models, or to biomolecules present at relatively high levels (μg/ml in blood). Lastly, existing microneedle-based in vivo sampling and detection methods are limited to qualitative analysis in which the target biomarker concentration is represented as relative fluorescence intensity, absorbance value or normalized relative quantity. This limitation precludes quantitative comparisons of the biomarker concentrations across different experiments and across different labs in biomedical research and decreases opportunities for standardization of the cut-off values for clinical biomarkers.

Devices, systems, and methods are disclosed herein for minimally-invasive, ultrasensitive, and quantitative measurement of target protein biomarkers in ISF as demonstrated through microneedle-based in vivo sampling and subsequent on-needle analysis. To improve the sensitivity of the microneedle-based immunoassay, an ultrabright fluorescent nanolabel was utilized, termed plasmonic-fluor, which improved the limit-of-detection of various ISF protein biomarkers by nearly 800-fold compared to conventional fluorophores and significantly shortened the in vivo sampling time (down to one minute). Moreover, by harnessing the bilayered design of the microneedle, replication of conventional immunoassay procedures was achieved on microneedle patches, including a calibration curve based on "standard micropatches".

Using a series of mouse models, the microneedle patch was demonstrated for use in ultrasensitive and quantitative monitoring of various protein biomarkers through a simple stick-and-peel process. Incorporation of magnetic backing layer enables simple and seamless implementation of conventional immunoassay procedures on the microneedle patch, leading to quantitative measurement of biomarkers with high consistency. First, the efficiency of a cocaine vaccine was successfully probed by monitoring cocaine-specific antibodies in dermal ISF. Second, sensitive detection and longitudinal monitoring of inflammatory biomarker levels in mice was demonstrated after induction of endotoxin-mediated shock. Last, the application of the microneedle patch was successfully validated in the efficient sampling, detection, and quantification of the matricellular protein periostin in the calvarial periosteum (a novel and challenging detection site) using both control wild type (WT) and periostin knock-out ($Postn^{KO}$) mice, which reveals localized information which cannot be inferred from other systemic fluids, such as blood. The minimally invasive microneedle patch obviates the need for repeated blood-drawing in a short period, which can cause poor patient compliance or potential death of experimental mice in preclinical settings.

The microneedle patch penetrates the dermal layer and samples the interstitial fluid in a pain-free manner, allowing the specific and selective binding of the target analyte to the capture biorecognition element (e.g., a capture antibody) antibody. The microneedle patch is also blocked to minimize non-specific adsorption of interfering proteins. The analyte bound on the microneedle was subsequently probed ex vivo by an extremely bright fluorescence nanolabel, e.g. plasmonic-fluor, to realize the ultrasensitive detection of the bioanalytes.

Conventional detection and quantification of analytes in interstitial fluid relies on extracting the ISF using microneedle, followed by detection ex vivo. However, sample withdrawal of ISF has several drawbacks, including the cumbersome size of the mechanical hardware (for example, vacuum) and thus of the device required for sample withdrawal; the time required for sample withdrawal, which directly increases the ISF lag; and the onset of sweating, which can confound the measurement accuracy. Furthermore, it is not certain whether ISF samples can be reliably extracted through needles or poration of the skin without altering analyte concentrations.

The present disclosure significantly simplifies the overall detection process by direct capture of target analyte in vivo instead of extracting the ISF through cumbersome methods and analyzing them ex vivo. The extremely bright nanolabel "plasmonic-fluor" enables femtomolar detection sensitivity, which is lower than the physiological range of most biomarkers. This level of sensitivity for bioanalyte (especially protein biomarker) detection in interstitial fluid has not been achieved by any other existing technologies. Considering the simplification and the ultra-sensitivity of the microneedle patch, high commercial potential is expected with applications in biomedical research and clinical diagnostics.

In some embodiments of the present disclosure, a bilayered microneedle patch is disclosed, wherein the patch comprises a magnetic backing layer and a microneedle layer. In some embodiments, the microneedle layer is attached to the magnetic backing layer. In some embodiments, the microneedle layer comprises an array of microneedles. In some embodiments, the array of microneedles comprises at least one, at least two, least three, at least five, at least ten, at least fifty or at least one hundred microneedles.

In some embodiments, the array of microneedles has a center-to-center spacing of about 100 µm, about 200 µm, about 300 µm, about 400 µm, about 500 µm, or about 600 µm between microneedles. In some embodiments, the array of microneedles has a center-to-center spacing of less than about 100 µm or less than about 600 µm between microneedles.

In some embodiments, at least one, at least two, at least three, at least five, at least ten or at least one hundred of the microneedles are coated with at least one capture biorecognition element (e.g., at least one capture antibody). In some embodiments, the microneedles are coated with multiple capture biorecognition elements.

In some embodiments, the microneedle layer comprises polystyrene, polyvinyl chloride, polypropylene, cycloolefin, or combinations thereof.

In some embodiments, the backing layer comprises a mixture of polymers and magnetic nanoparticles. The polymers are selected from polystyrene, polyvinyl chloride, polypropylene, cycloolefin, and combinations thereof. The magnetic nanoparticles are selected from iron-containing magnetic materials, nickel-containing magnetic materials, cobalt-containing magnetic materials, and other magnetic materials. In some embodiments, the magnetic nanoparticles are $Fe_3O_4$ nanoparticles. In some embodiments, the mixture comprises polystyrene and $Fe_3O_4$ nanoparticles.

In some embodiments, an assay for detection of a target ISF analyte is disclosed. In some embodiments, the assay comprises a microneedle patch comprising a magnetic backing layer and a microneedle layer attached to the magnetic backing layer, wherein the microneedle layer comprises an array of microneedles coated with a plurality of capture biorecognition elements (e.g., capture antibodies); a plurality of detection biorecognition elements (e.g., detection antibodies); and a plurality of fluorescent labels comprising plasmonic-fluor.

In some embodiments, the detection biorecognition elements comprise biotin.

In some embodiments, the plurality of fluorescent labels further comprises streptavidin. In some embodiments, the detection antibody is directly conjugated to the plasmonic-flour.

In some embodiments, the target ISF analyte is a protein biomarker selected from pro-inflammatory cytokines, antibodies in response to bacterial infections, antibodies in response to viral infections, antibodies in response to vaccination, biomarkers and small molecules. In some embodiments, the pro-inflammatory cytokine is mouse interleukin 6 (IL-6). In some embodiments, the biomarker is a CA125, a neutrophil gelatinase-associated lipcalin (NGAL) or a kidney injury molecule 1 (KIM1). In some embodiments, the small molecule is cortisol.

In some embodiments, the capture biorecognition elements are selected from DNA aptamers, proteins, peptides, periostin, capture antibodies, antibodies against cardiac troponin, antibodies against CA125, antibodies against neutrophil gelatinase-associated lipcalin (NGAL), and antibodies against kidney injury molecule 1 (KIM1).

In some embodiments, a method for detecting a target ISF analyte is disclosed. In some embodiments, the method comprises administering a microneedle patch to penetrate a dermal layer of a subject and sample the ISF of the subject, wherein the microneedle patch comprises a magnetic backing layer and a microneedle layer attached to the magnetic backing layer, wherein the microneedle layer comprises an array of microneedles coated with a plurality of capture biorecognition elements (e.g., capture antibodies); removing the microneedle patch from the dermal layer of the subject; adding a plurality of detection biorecognition elements (e.g., detection antibodies) to the microneedle patch; adding a plurality of fluorescent labels to the microneedle patch, wherein each of the plurality of fluorescent labels comprises a plasmonic-fluor; and detecting the target ISF analyte based on a fluorescence signal from the plasmonic-fluor.

EXAMPLES

The following examples illustrate various aspects of the disclosure.

Example 1: Design and Fabrication of the Microneedle Patch

Figure 2:
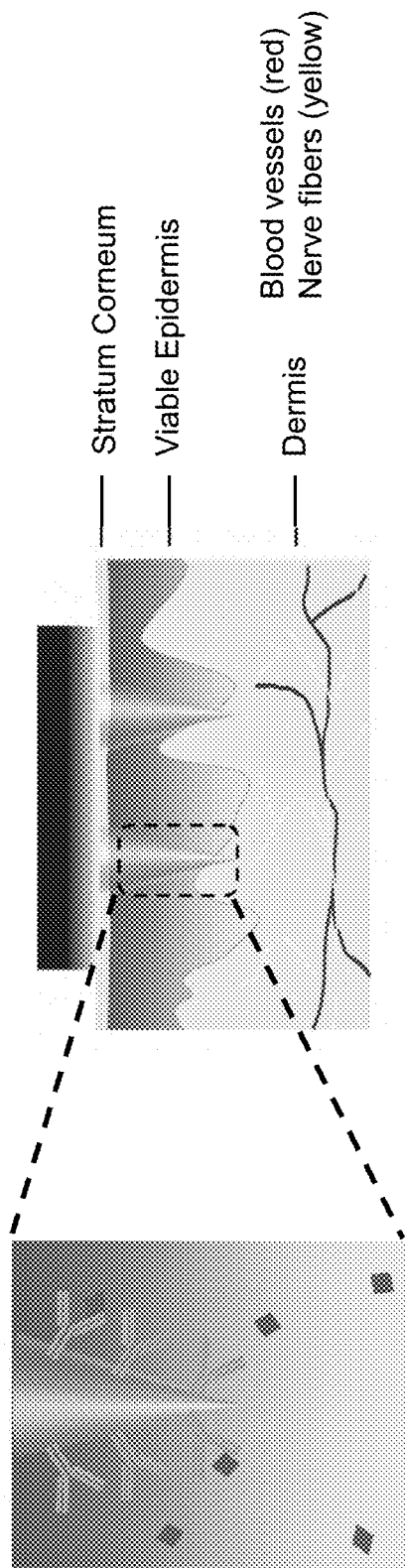
FIG. 2 is an exemplary embodiment of dermal penetration of a microneedle patch in accordance with the present disclosure.
Figure 3:
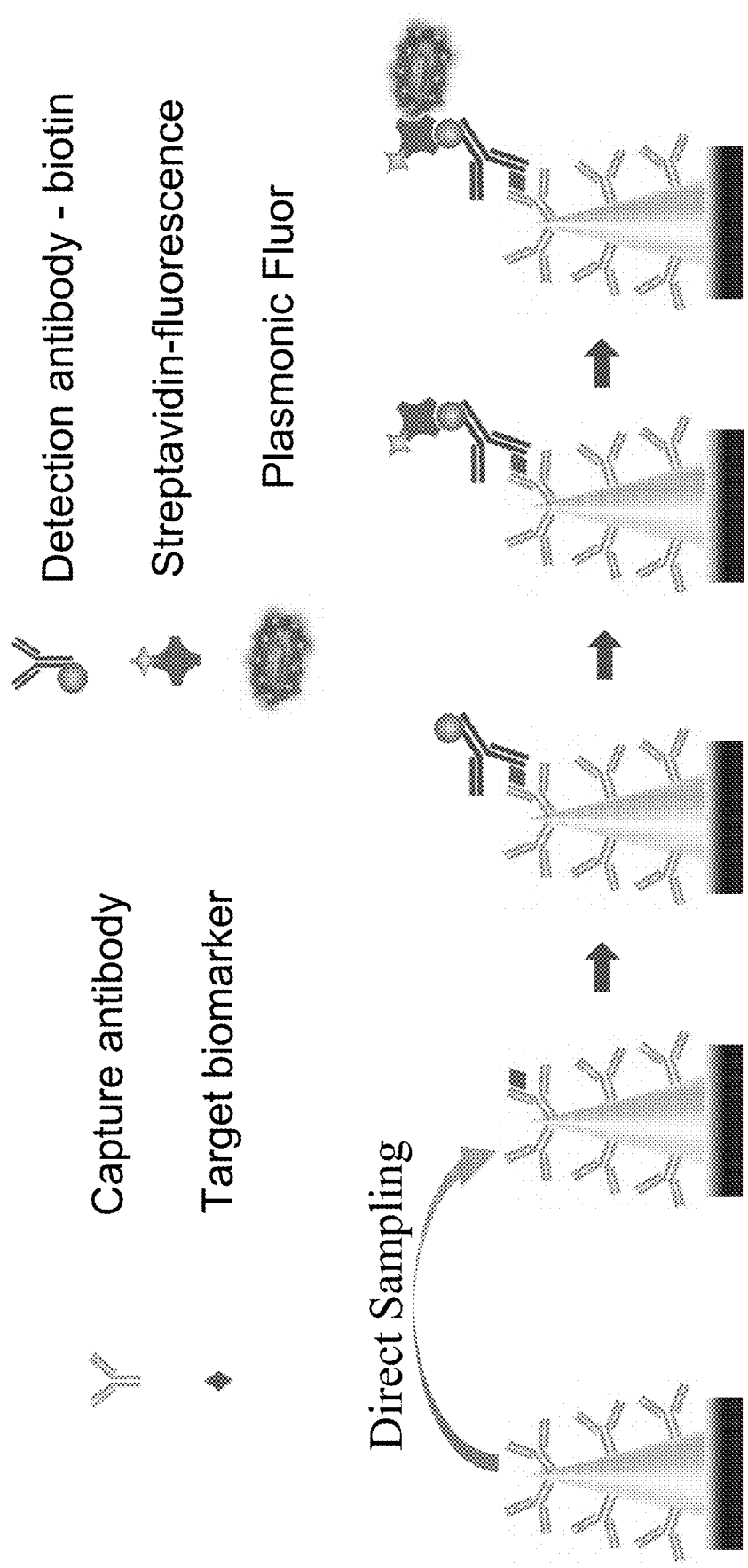
FIG. 3 is an exemplary embodiment of an illustration of direct sampling and on-needle detection of target biomarkers in accordance with the present disclosure.
Figure 4:
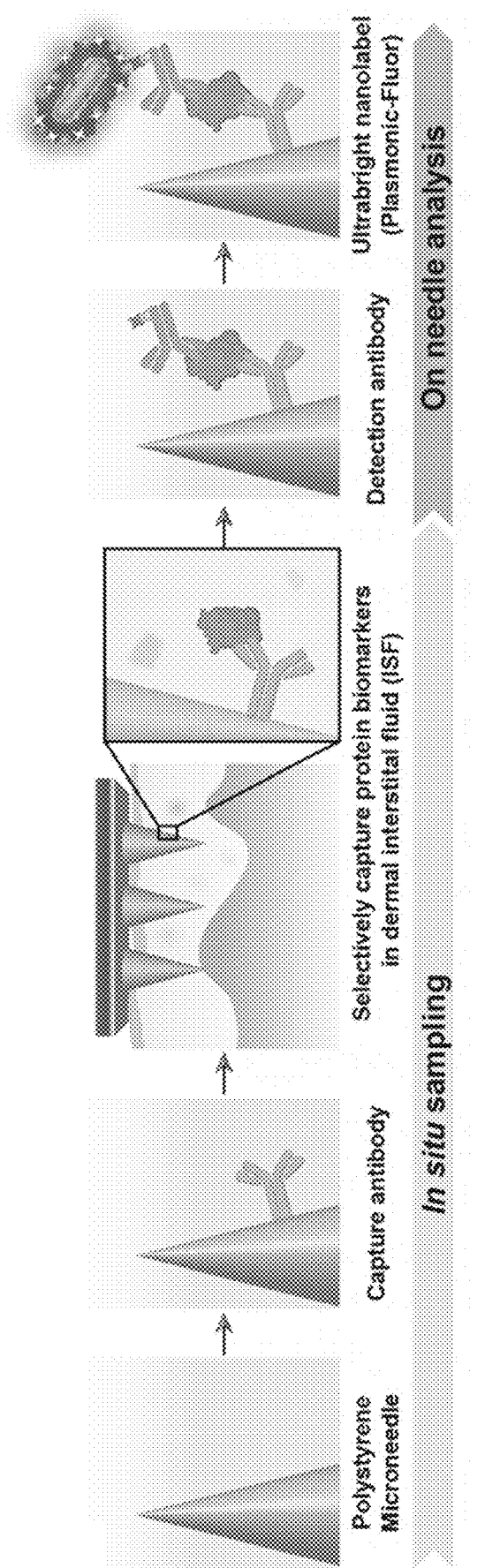
FIG. 4 is an exemplary embodiment of a schematic illustration showing work flow of microneedle-based biodetection involving in situ sampling and on-needle detection of protein biomarkers in interstitial fluid (ISF) in accordance with the present disclosure.

The novel biodetection platform introduced in this study relies on microneedles functionalized with biorecognition elements (e.g. antibodies) that penetrate the stratum corneum (or periosteum; see FIG. 2) and selectively capture protein biomarkers in the local ISF in a concentration-dependent manner. Subsequently, the microneedle patch was peeled off from the skin and the protein biomarkers bound on the microneedles were quantified by an ultrasensitive fluoroimmunoassay implemented ex vivo (FIGS. 3 and 4). For efficient capture of target biomarkers in vivo, microneedles are required to exhibit high protein/antibody binding ability, high mechanical strength, and biocompatibility. Owing to its low cost, facile processability, and hydrophobic nature, polystyrene is widely utilized for microtiter plates in biomedical research and clinical diagnostics. Affinity reagents such as capture biorecognition elements, including capture antibodies and blocking proteins, are efficiently immobilized on the polystyrene surface owing to the hydrophobic interactions between polystyrene and non-polar residues of the proteins. Thus, in some embodiments, polystyrene was employed for the fabrication of the microneedles, which were subsequently coated with capture biorecognition elements (e.g., capture antibodies) to enable specific binding of the target biomarkers.

Figure 5:
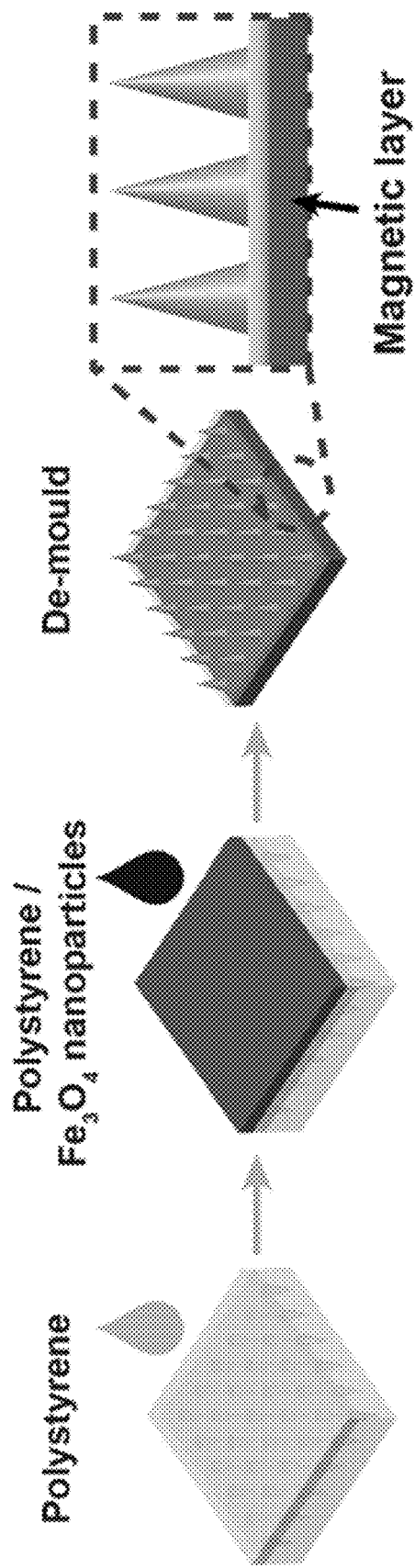
FIG. 5 is an exemplary embodiment of a schematic illustration of the fabrication steps of a bilayered microneedle patch in accordance with the present disclosure.
Figure 6:
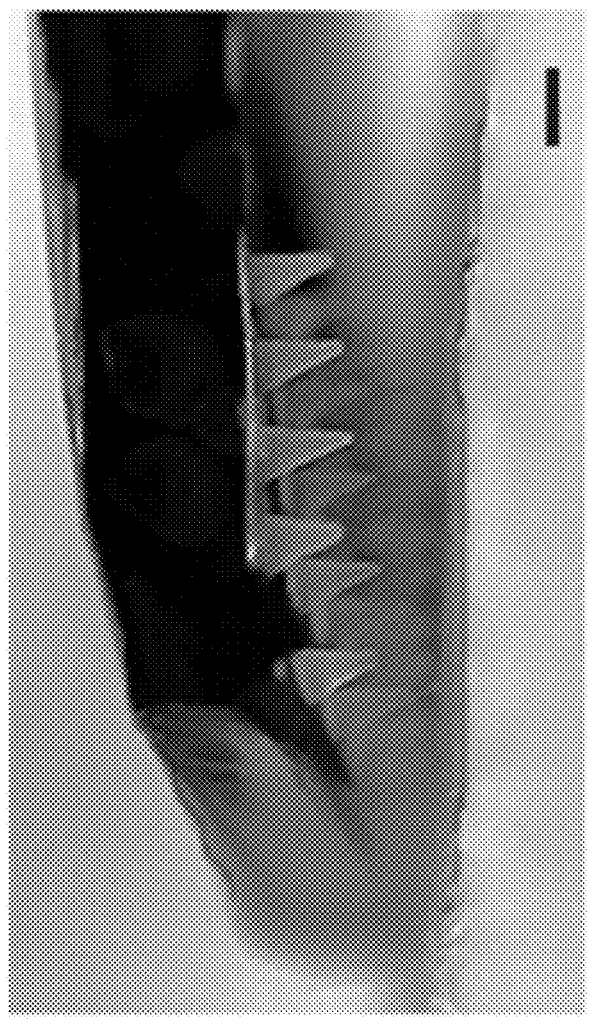
FIG. 6 is an exemplary embodiment of a representative optical image of a microneedle patch with a magnetic backing layer (black) and pristine polystyrene needles (hazy), scale bar 500 mm, in accordance with the present disclosure.
Figure 7A:
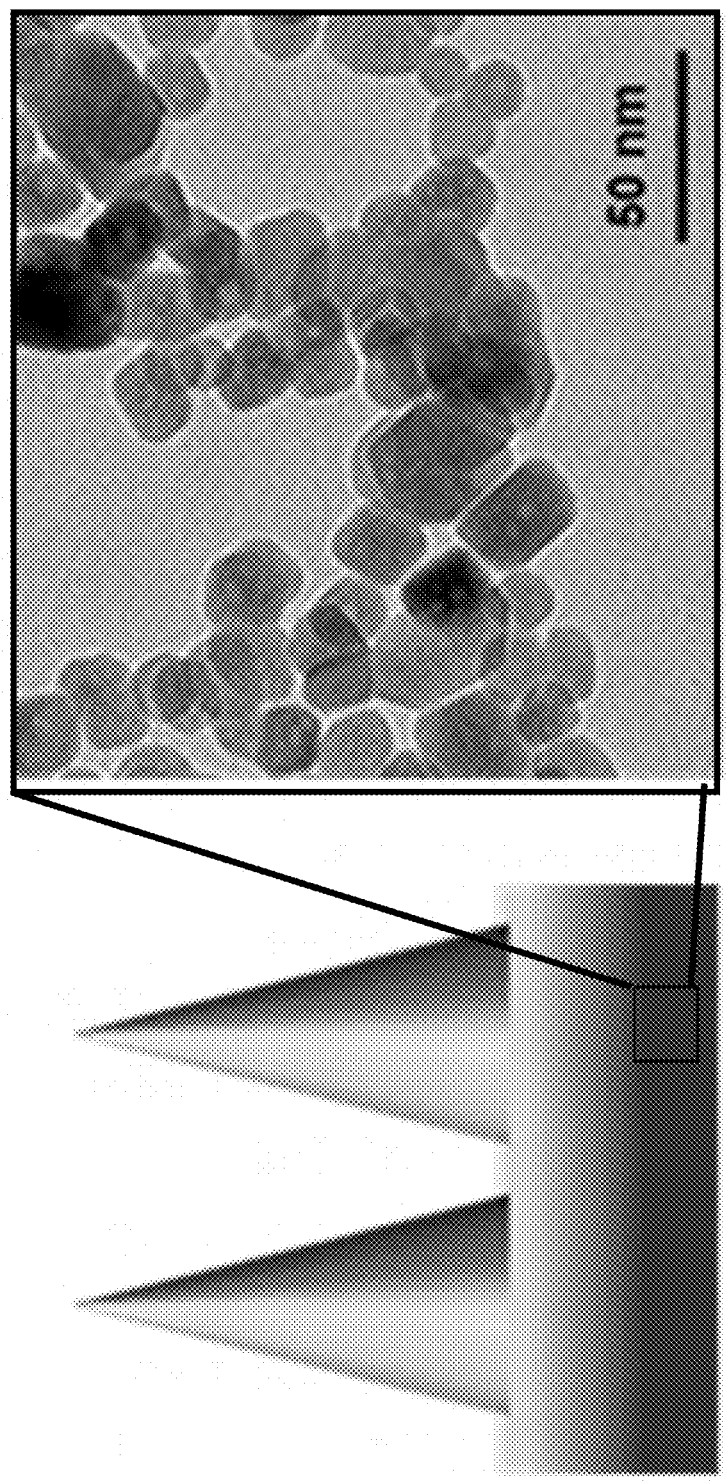
FIG. 7A is an exemplary embodiment of a TEM image of $Fe_3O_4$ magnetic nanoparticles embedded in the bottom layer of the microneedle patch in accordance with the present disclosure.
Figure 7B:
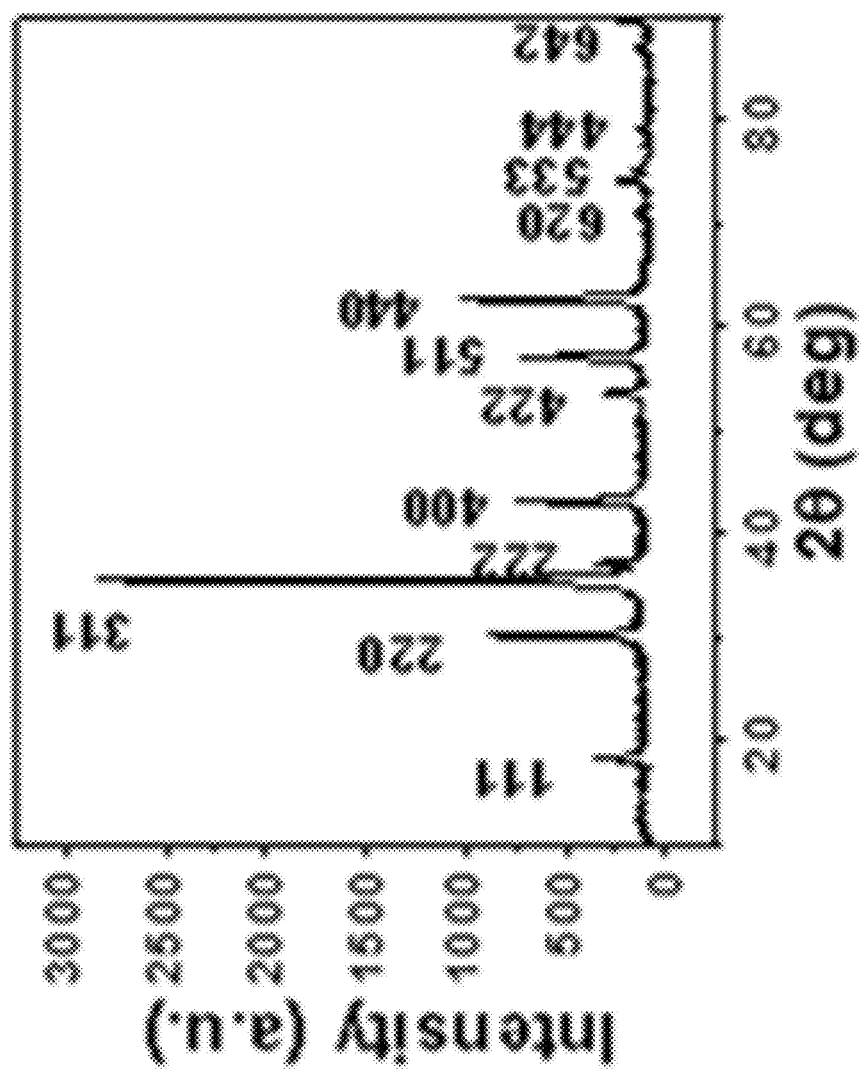
FIG. 7B is an exemplary embodiment of an XRD spectrum of $Fe_3O_4$ magnetic nanoparticles embedded in the bottom layer of a microneedle patch in accordance with the present disclosure.
Figure 8:
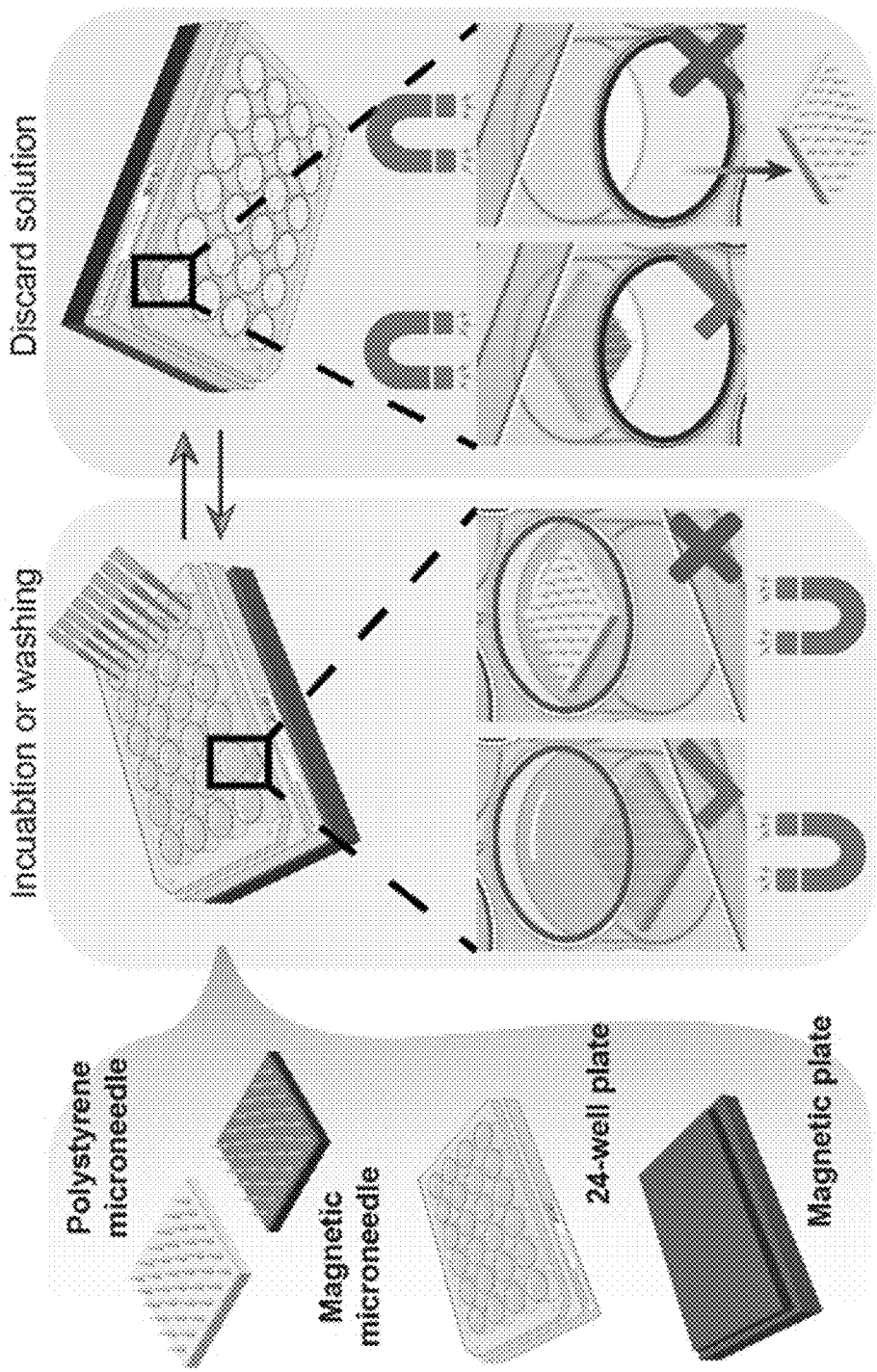
FIG. 8 is an exemplary embodiment of a schematic illustration depicting the importance of employing a microneedle patch with embedded magnetic nanoparticles, which facilitates various standard immunoassay procedures such as incubation and washing steps, and overcomes low-efficient patch-by-patch handling in accordance with the present disclosure.
Figure 9:
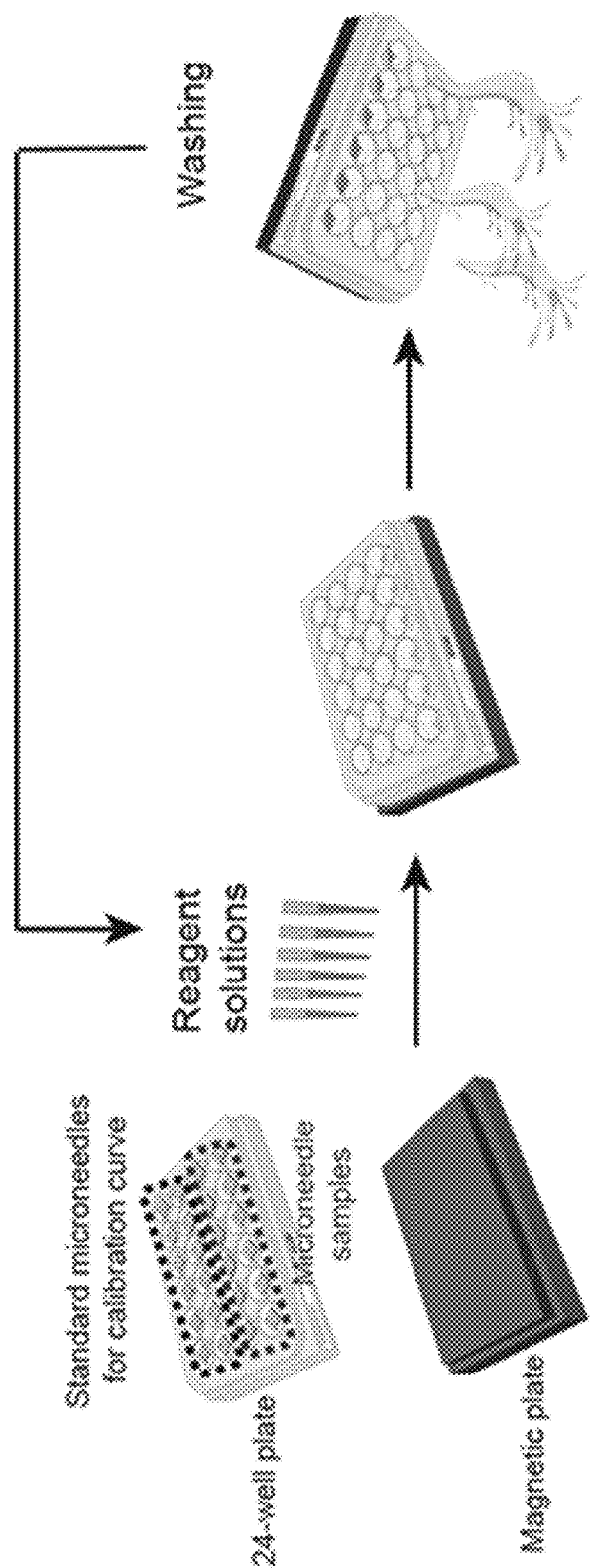
FIG. 9 is an exemplary embodiment of a workflow of quantitative immunoassay implemented on a bilayered microneedle patch comprised of magnetic nanoparticles in the bottom layer in accordance with the present disclosure.
Figure 10:
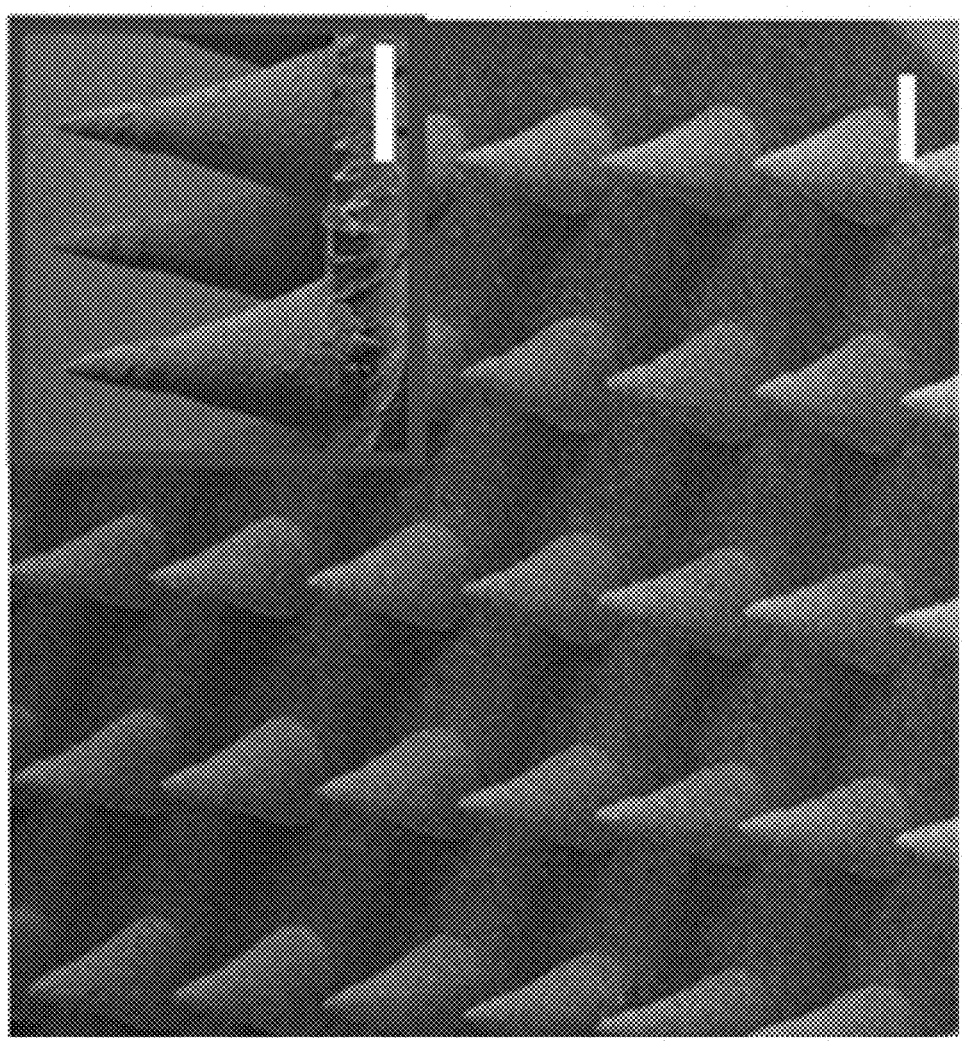
FIG. 10 is an exemplary embodiment of a representative SEM image of an as-fabricated microneedle patch, scale bar 100 mm, in accordance with the present disclosure. Inset image shows side view of microneedle, scale bar 200 mm.
Figure 11:
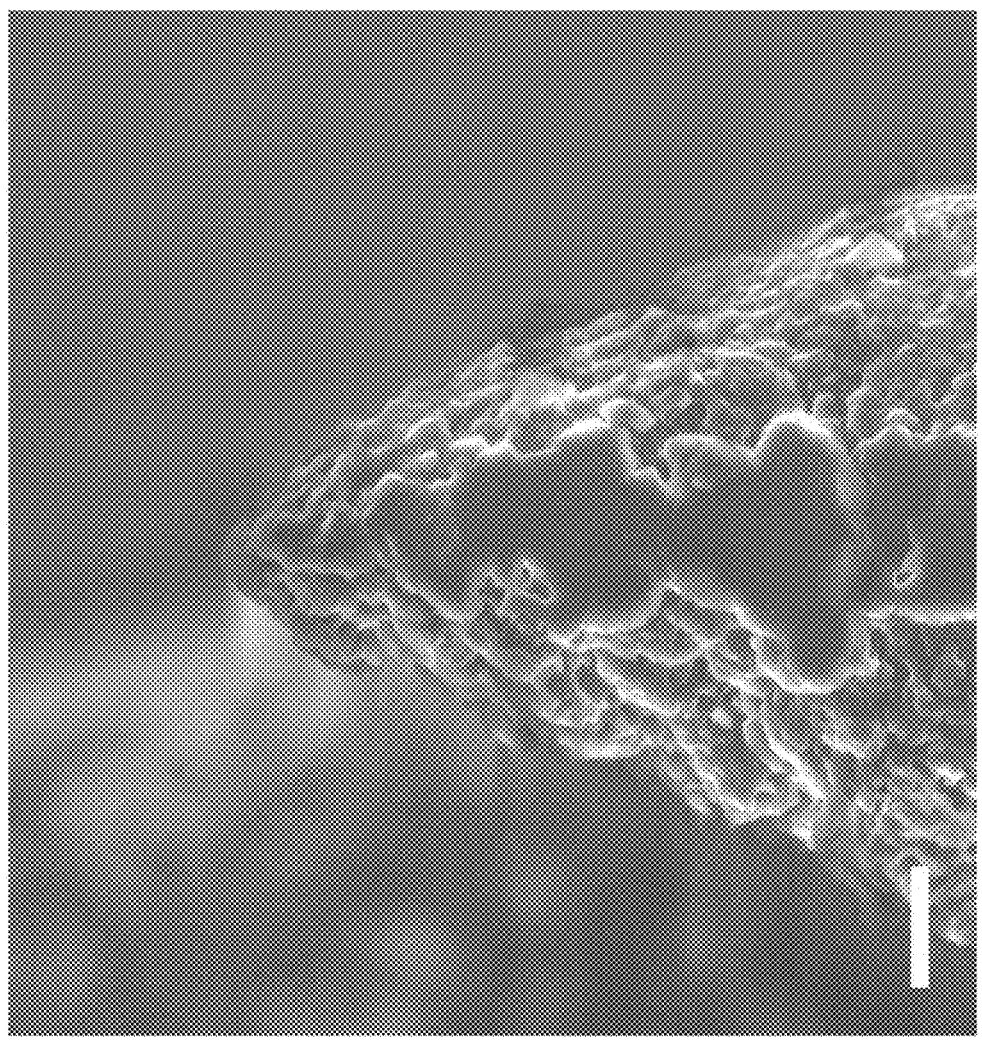
FIG. 11 is an exemplary embodiment of a representative SEM image of microneedle tip, radius of curvature 4 µm, in accordance with the present disclosure. Scale bar 10 µm.
Figure 12:
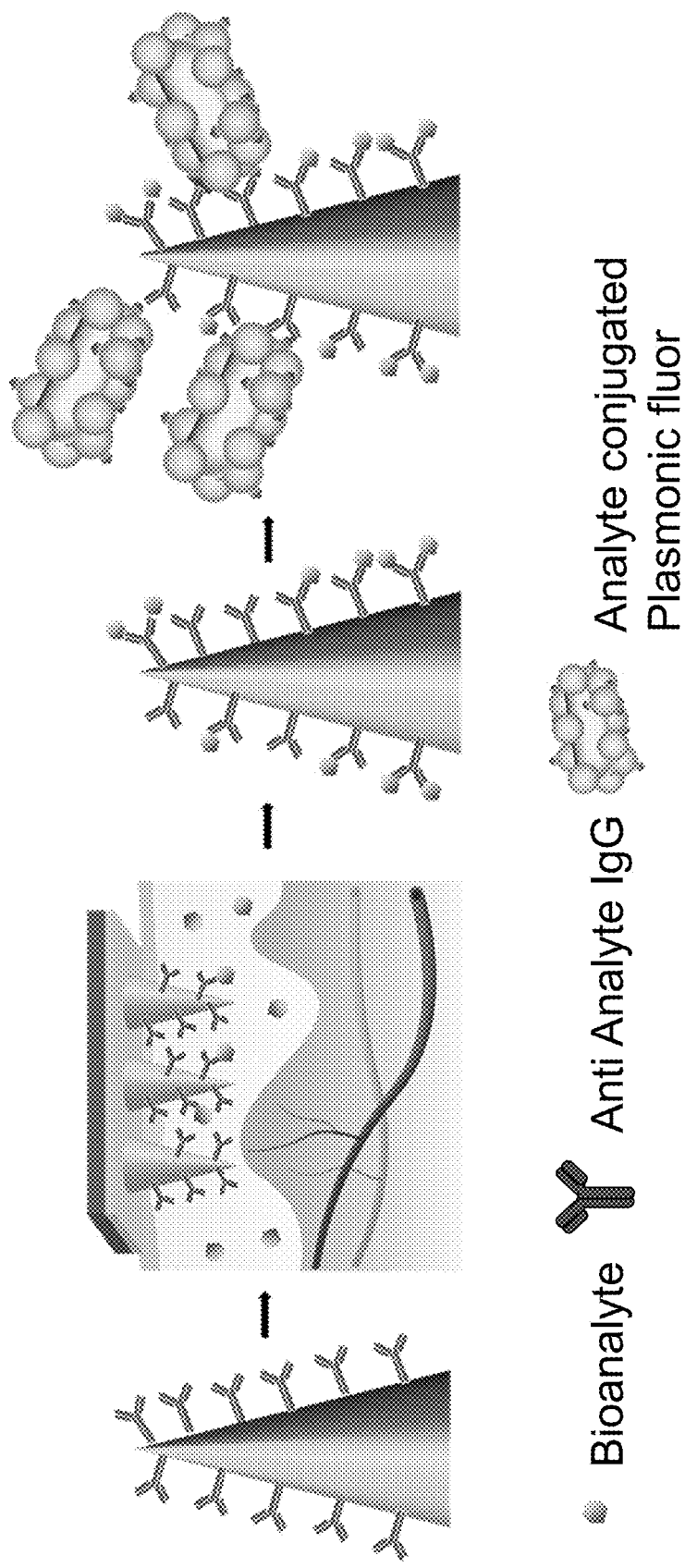
FIG. 12 is an exemplary embodiment of a plasmonic-fluor competitive assay on a microneedle for small molecule detection in ISF in accordance with the present disclosure.
Figure 13:
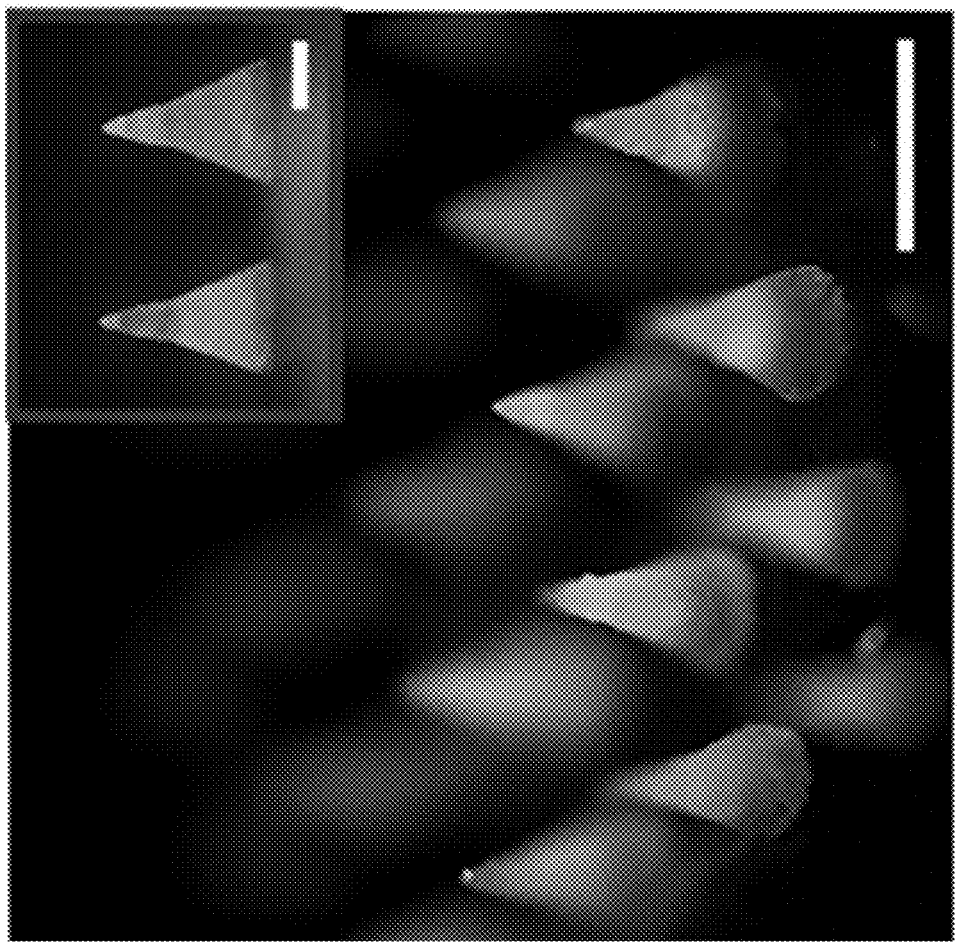
FIG. 13 is an exemplary embodiment of a representative fluorescence microscopy images demonstrating efficient and uniform adsorption of antibodies on polystyrene microneedles, scale bar 500 mm, in accordance with the present disclosure. Inset image shows side view of fluorescence signal on microneedle, scale bar 200 mm.
Figure 14A:
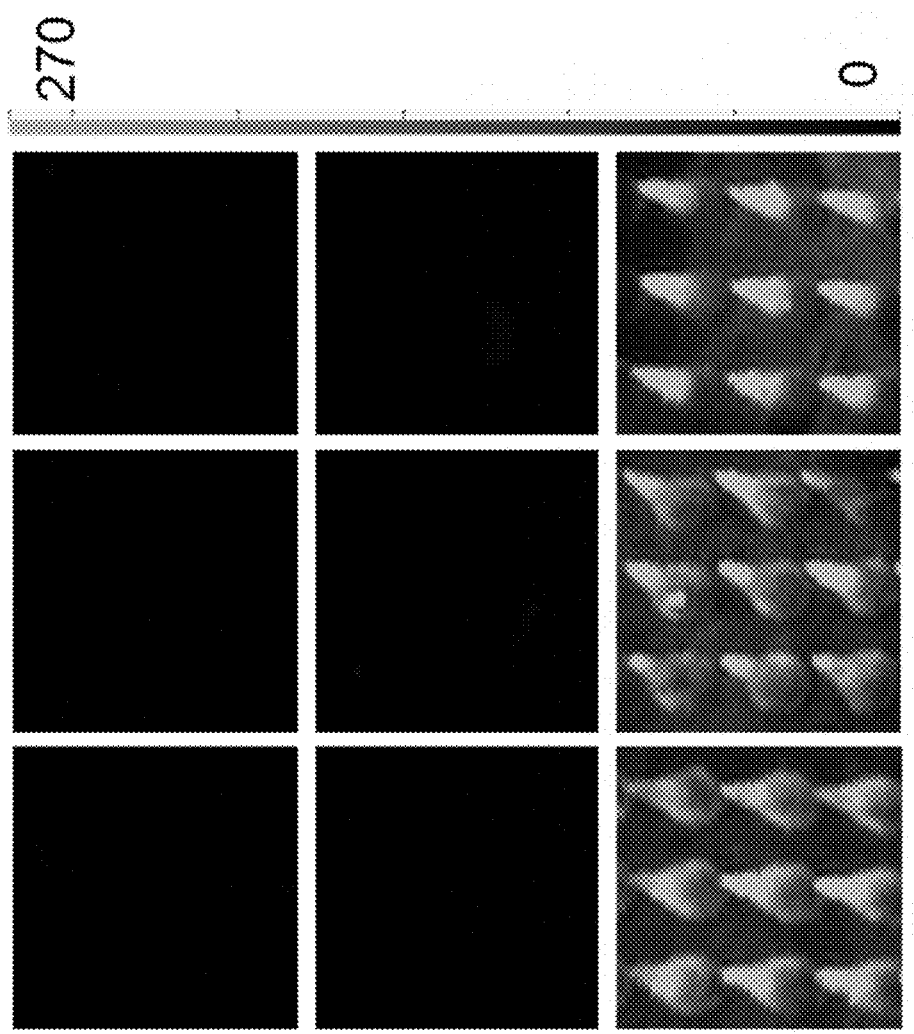
FIG. 14A is an exemplary embodiment of fluorescence images corresponding to pristine microneedles, BSA coated microneedles exposed to LT680-streptavidin, and biotinylated IgG coated microneedles exposed to LT680-streptavidin in accordance with the present disclosure.
Figure 14B:
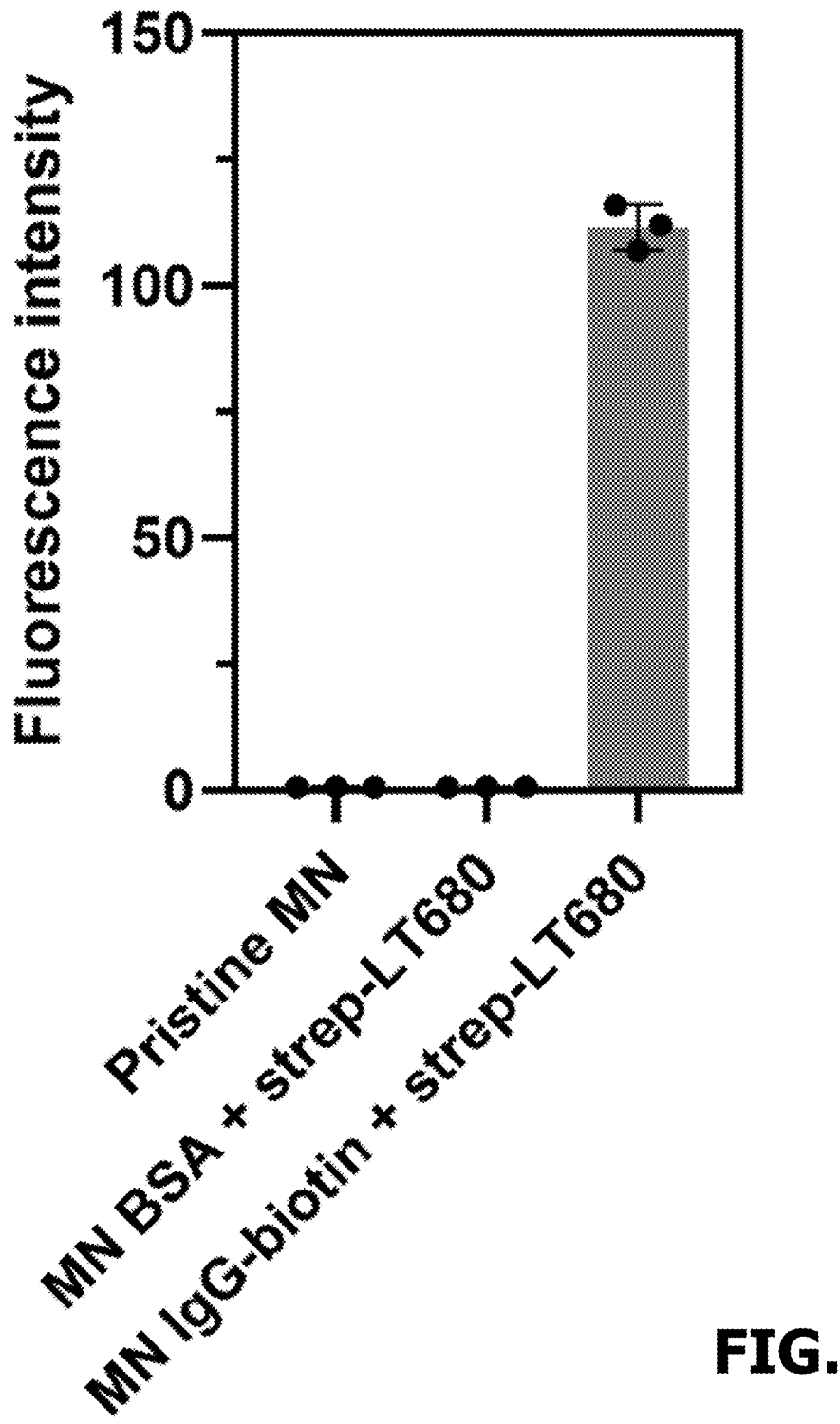
FIG. 14B is an exemplary embodiment of a plot showing that BSA coated microneedles exhibit extremely weak fluorescence intensity (155-fold lower compared to biotinylated IgG coated microneedles, close to the instrument background), indicating the successful coating of the antibodies (IgG) on the polystyrene microneedle surface, in accordance with the present disclosure. Error bar represents standard deviation, N=3 repeated tests.

The microneedle patch was fabricated using a silicone mold via two successive drop-casting steps (FIG. 5). Polystyrene solution (25% w/v in dichloromethane) was first cast on a silicone mold and the solvent was allowed to evaporate slowly under ambient conditions. Subsequently, a backing layer comprised of the mixture of polystyrene and magnetic nanoparticles ($Fe_3O_4$ nanoparticles) was formed on top of the pristine polystyrene layer. Incorporation of the magnetic nanoparticles in the backing layer is important to ensure that the microneedle patches stay at the bottom of a microtiter plate in the presence of a magnet underneath during subsequent immunoassay procedures (FIGS. 5, 6, and 7A-B). This bilayered design overcomes the low throughput and poor reproducibility of patch-by-patch handling (i.e. incubation and wash steps performed manually one patch at a time), making the microneedle-based assay highly consistent, fast and reproducible (FIG. 8, 9). Incorporation of magnetic layer facilitates the use of standard immunoassay procedures including washing and incubation steps. The patch is comprised of an array of microneedles with a center-to-center distance of 600 μm (FIG. 10). Each microneedle is conical in shape with a 4 μm radius of curvature at the tip, a diameter of 300 μm at the base, and around 600 μm in height (FIG. 10, 11). To assess the density and uniformity of antibody coating on polystyrene microneedles (FIG. 12), the microneedles were coated with biotinylated anti-mouse IgG followed by blocking with bovine serum albumin (BSA). Subsequently, the microneedle patches were exposed to dye (LT680)-labeled streptavidin, resulting in a strong and uniform fluorescence signal along the entire length of the microneedle suggesting the uniform coating of the antibodies and BSA (as blocking layer) on the polystyrene microneedle surface (FIG. 13). In contrast, microneedles coated with BSA which subsequently exposed to LT680-streptavidin exhibited extremely weak fluorescence intensity (155-fold lower, signal close to pristine microneedle) (FIG. 14A-B), suggesting low auto-fluorescence of the BSA and polystyrene microneedle surface.

Figure 15A:
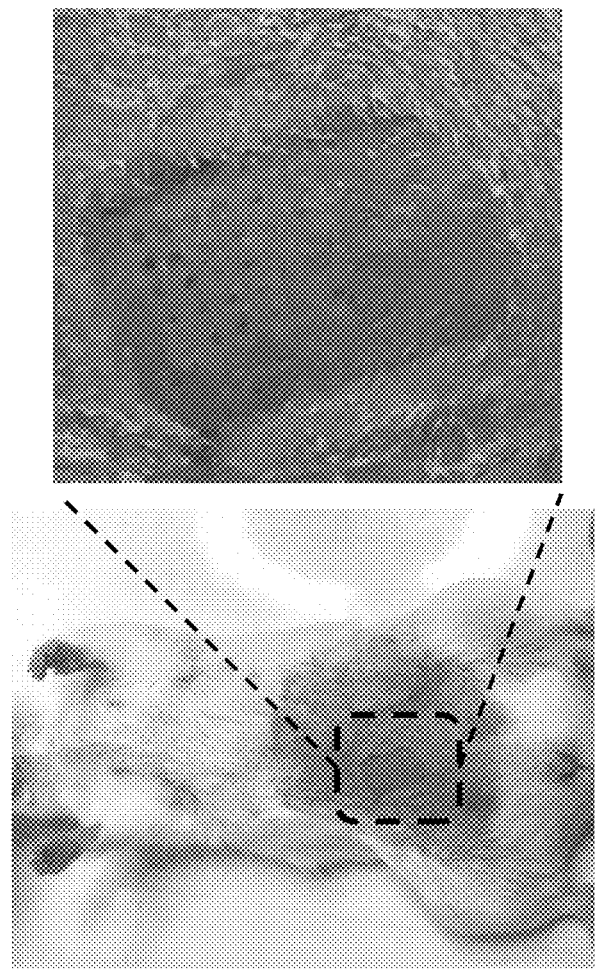
FIG. 15A is an exemplary embodiment of optical images demonstrating abdominal position of a microneedle patch administration site in accordance with the present disclosure.
Figure 15B:
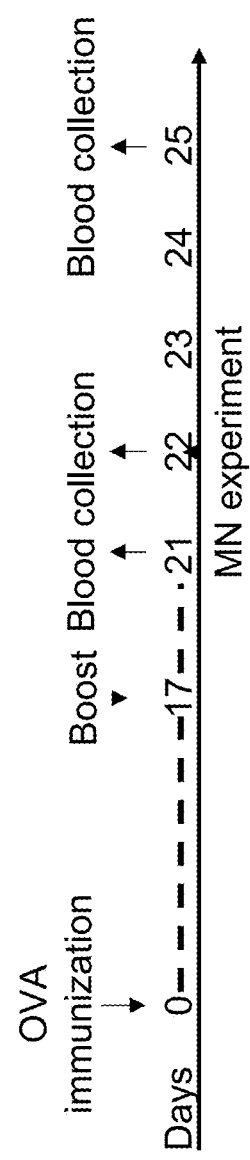
FIG. 15B is an exemplary embodiment of a timeline of OVA immunization and blood collection on mice in accordance with the present disclosure.
Figure 16A:
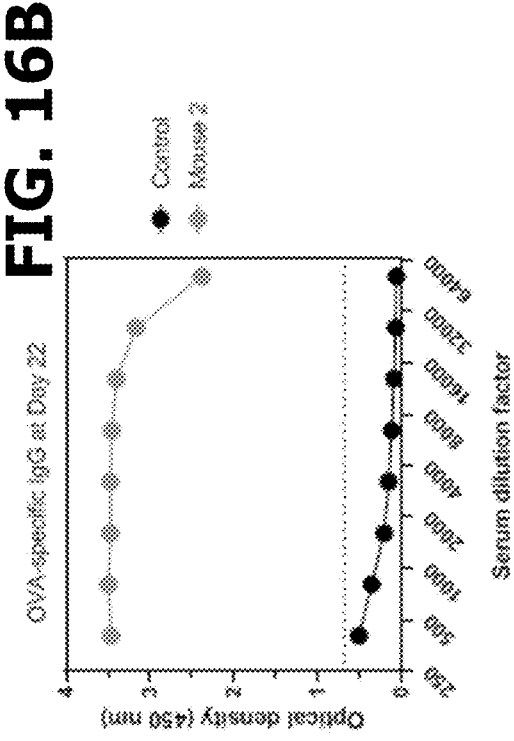
FIG. 16A is an exemplary embodiment of IgG titer inside serum at Day 21 in accordance with the present disclosure.
Figure 16B:
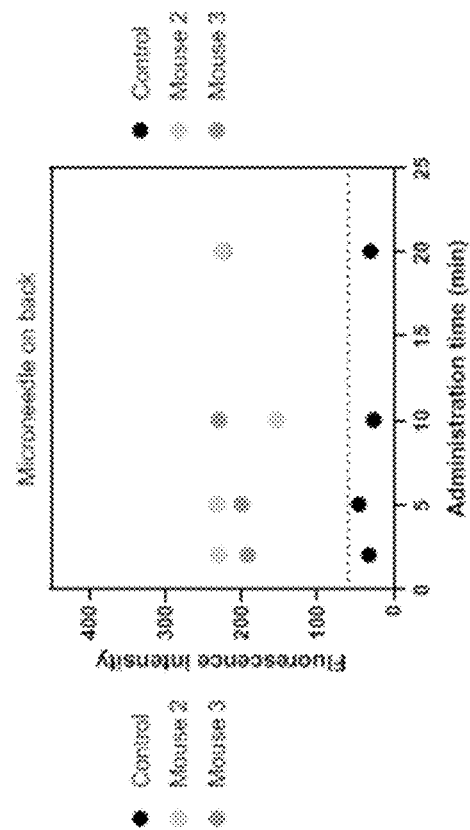
FIG. 16B is an exemplary embodiment of IgG titer inside serum at Day 22 in accordance with the present disclosure.
Figure 16C:
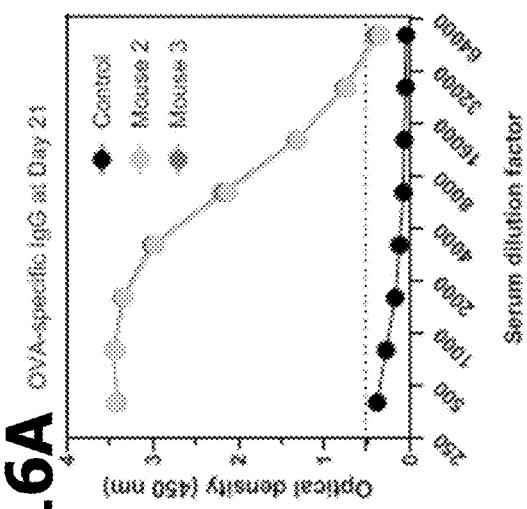
FIG. 16C is an exemplary embodiment of microneedle signal after being administered on the abdomen for different times in accordance with the present disclosure.
Figure 16D:
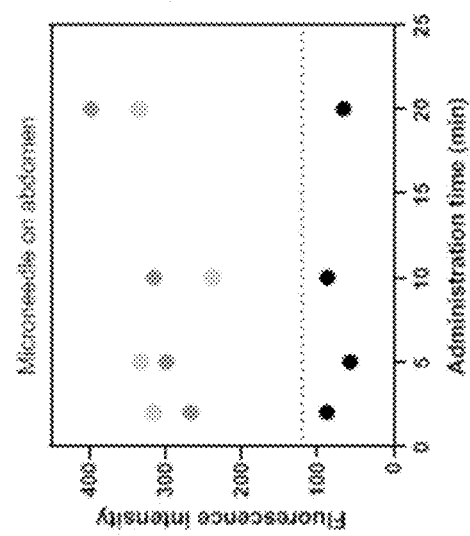
FIG. 16D is an exemplary embodiment of microneedle signal after being administered on the back for different times in accordance with the present disclosure.
Figure 17:
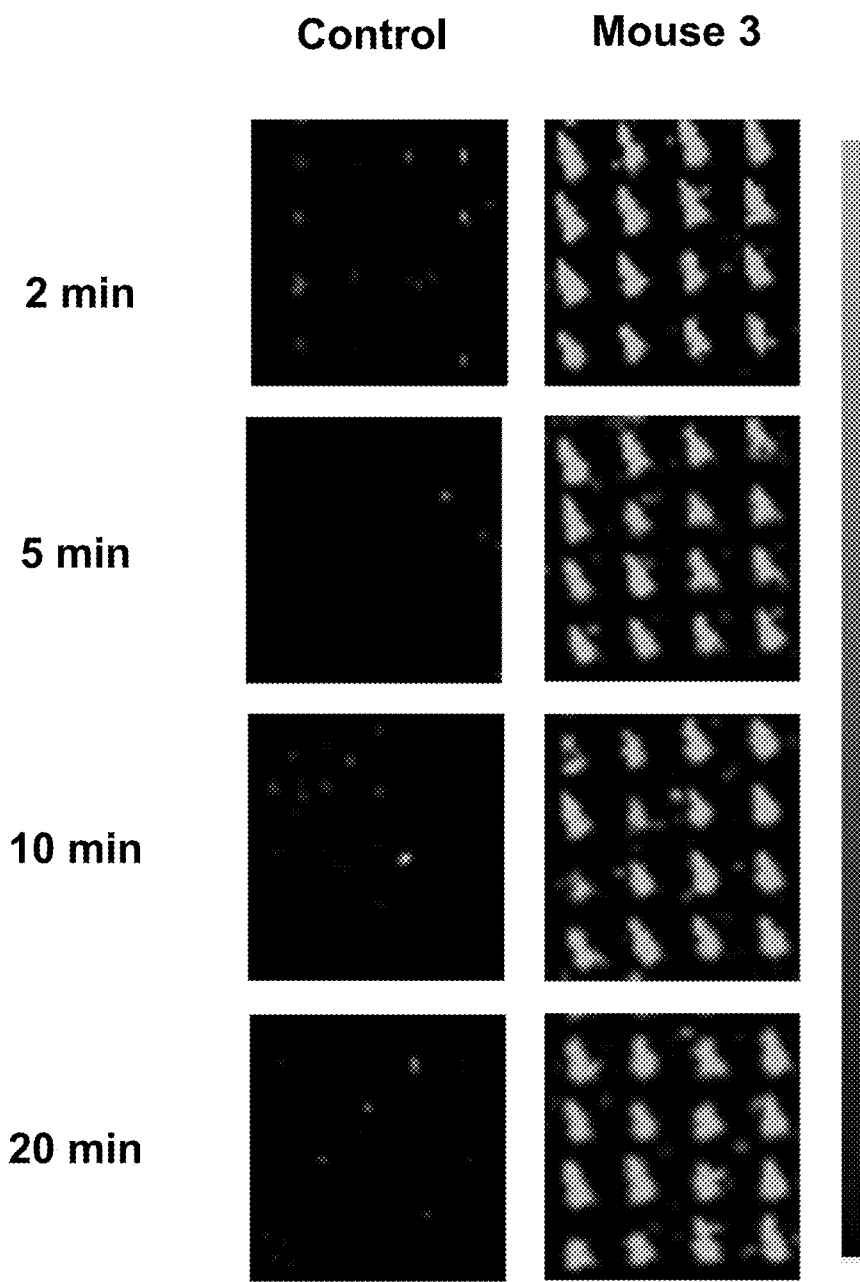
FIG. 17 is an exemplary embodiment of control versus mouse fluorescence signal over time in accordance with the present disclosure.

Antigen specific IgG detection in dermal ISF was demonstrated through microneedle detection of OVA specific IgG detection (FIG. 15A), using ELISA/PF-FLISA to determine OVA-specific IgG titer with OVA as capture antibody, mouse serum/ISF as sample, and (biotinylated) donkey anti-mouse IgG as detection antibody. OVA specific IgG concentrations were around mg/ml level in serum and maintained similar levels from day 20 to day 25 (FIG. 15B and FIG. 16A-D). Even a 2-minute-administration effectively tells the difference between control mouse and immunized mice (FIG. 17). The signal intensity did not show a significant difference between 2 min and 20 min data points, indicating that the microneedle was saturated in about the first 2-5 mins. FIG. 17 demonstrates the fluorescence signal from control mouse and immunized mouse where the intensities are very different.

Figure 18:
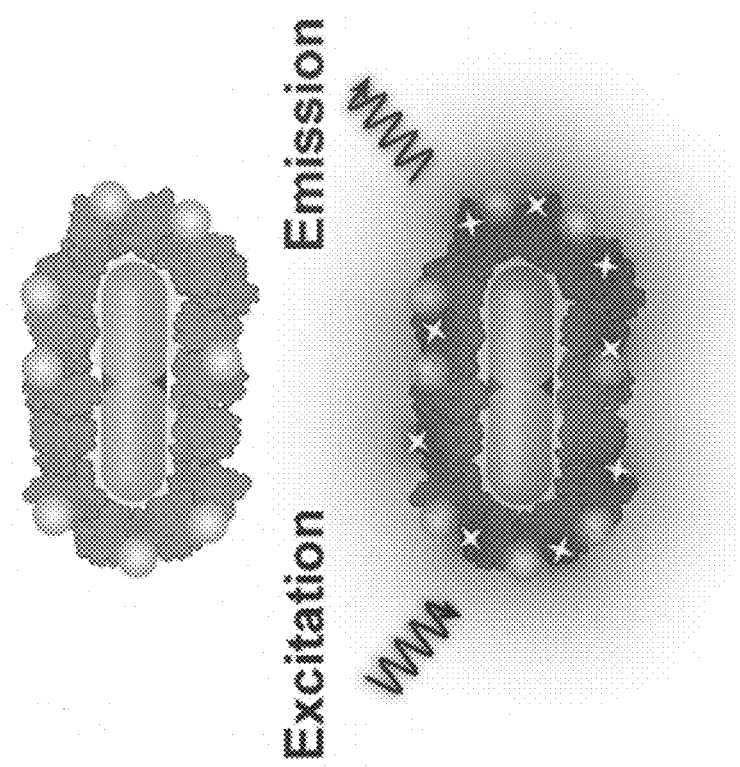
FIG. 18 is an exemplary embodiment of a schematic illustration of plasmonic-fluor as ultrabright fluorescence nanolabel in accordance with the present disclosure.
Figure 20:
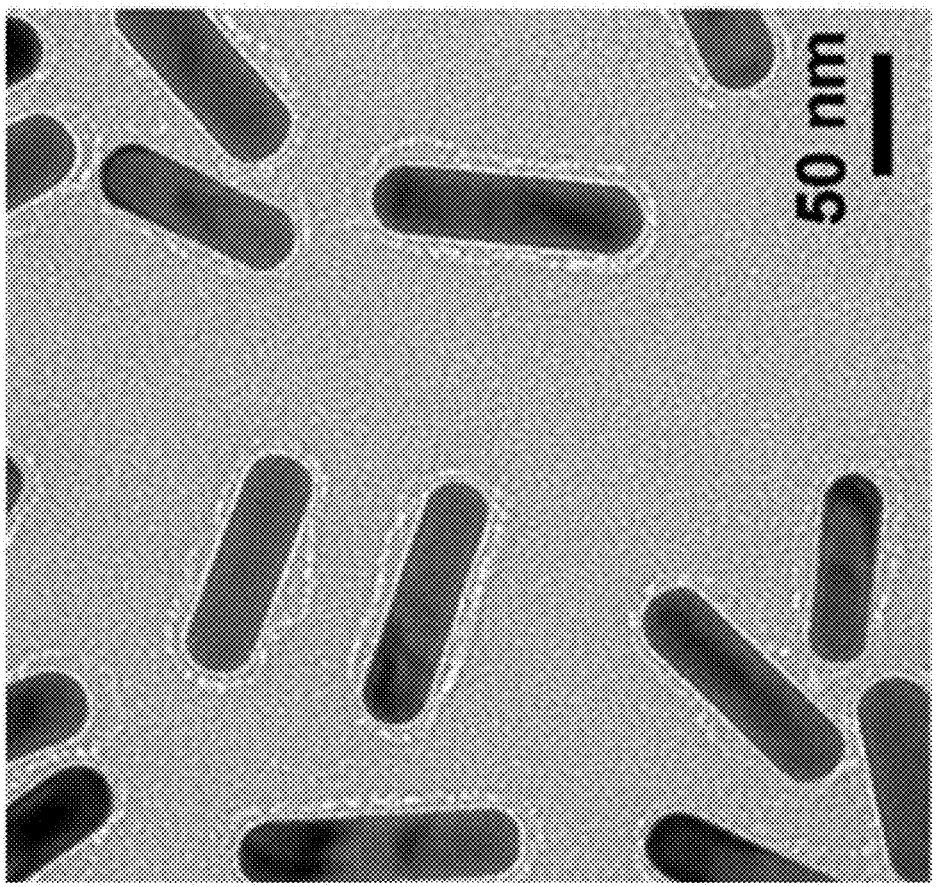
FIG. 20 is an exemplary embodiment of a representative TEM image of plasmonic-fluors in accordance with the present disclosure.
Figure 21B:
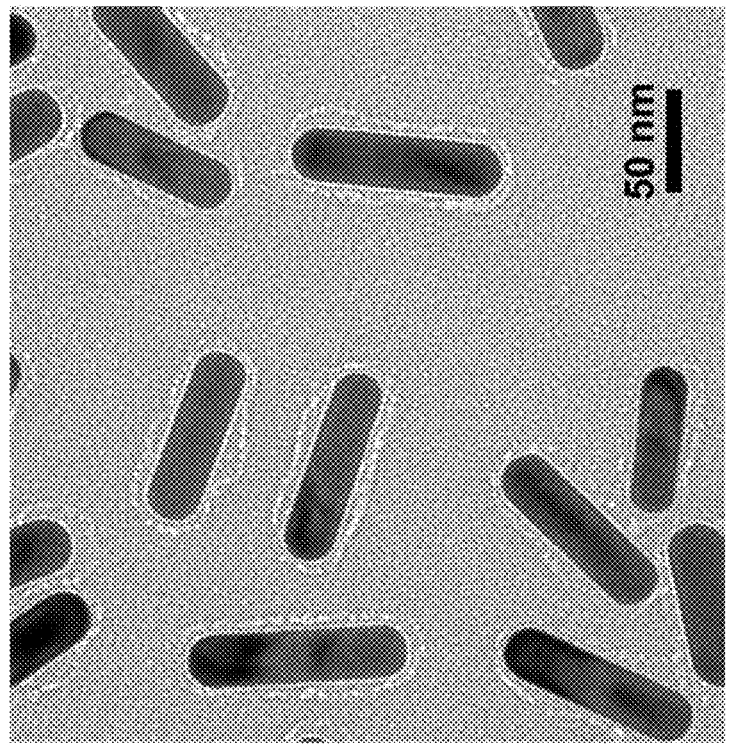
FIG. 21B is an exemplary embodiment of a representative TEM image of plasmonic-fluor in accordance with the present disclosure.
Figure 21A:
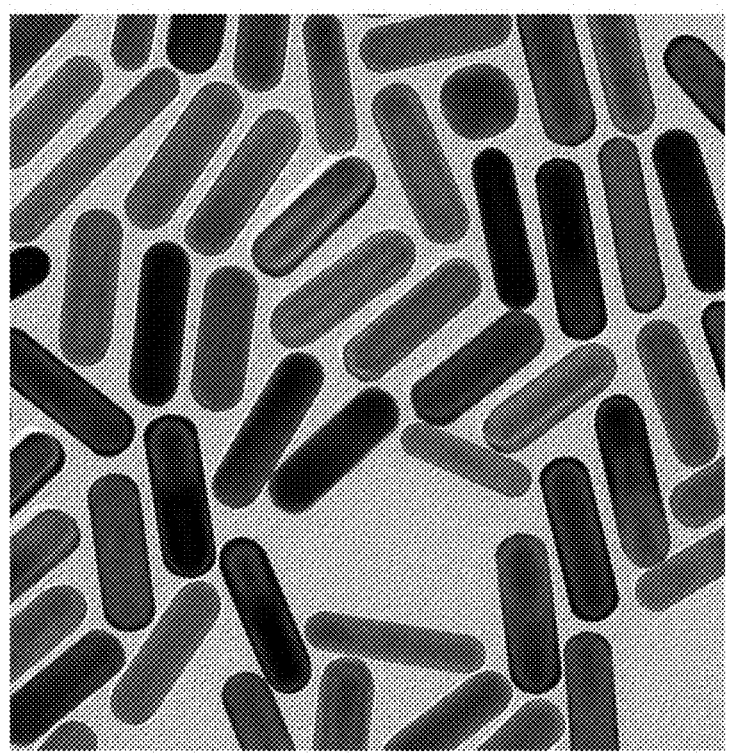
FIG. 21A is an exemplary embodiment of a representative TEM image of gold nanorods (AuNRs) employed as the plasmonic nanoantenna in accordance with the present disclosure.
Figure 22:
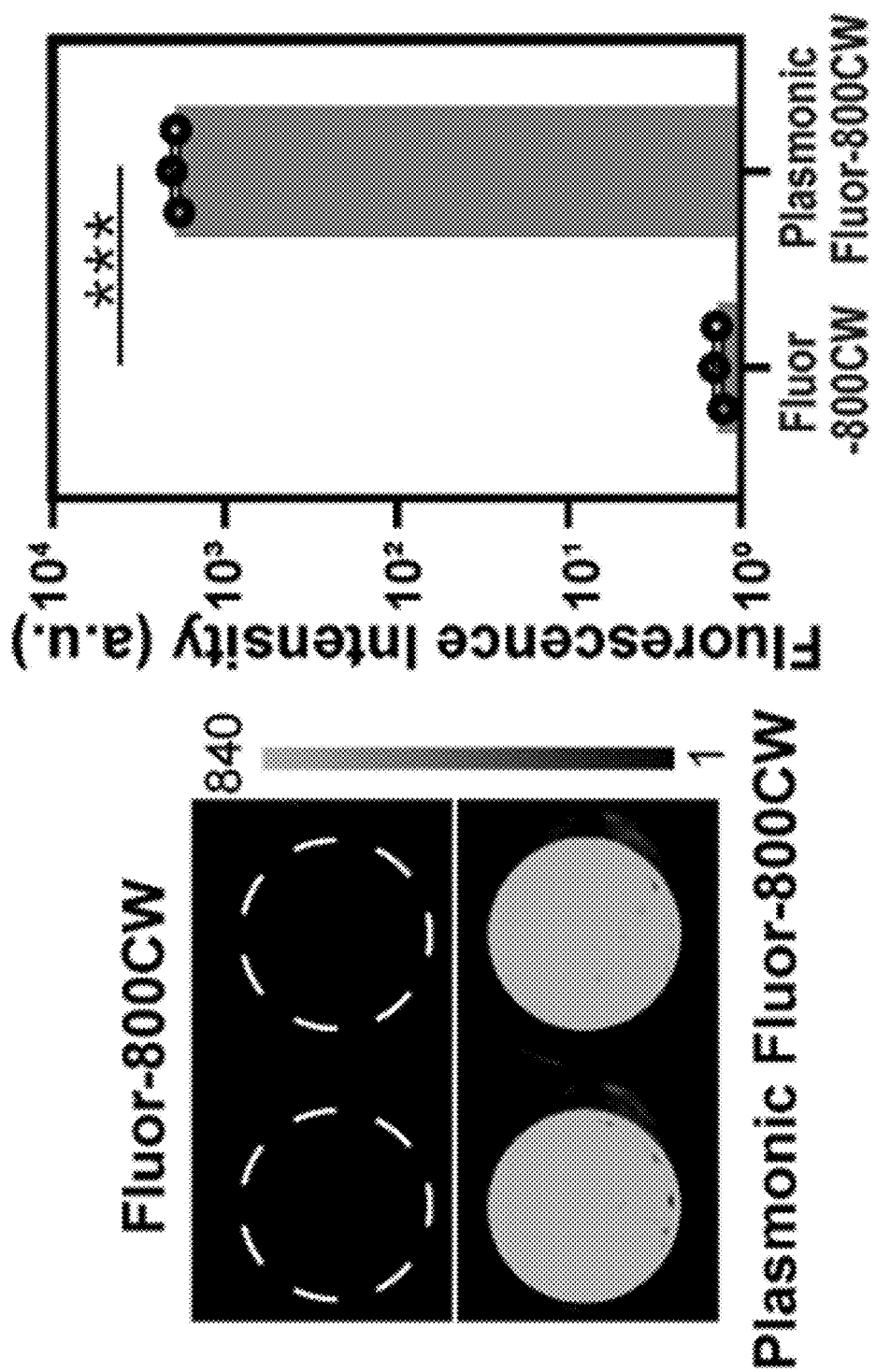
FIG. 22 is an exemplary embodiment of fluorescence images and corresponding intensity of 800CW-streptavidin followed by the specific binding of plasmonic-fluor through biotin-streptavidin interaction, showing 1424-fold increase in fluorescence intensity in accordance with the present disclosure. Error bars, s.d. data statistically significant P value=0.0004, *** P<0.001 by one-tailed unpaired t-test with Welch's correction, fluorescence intensity maps of mouse IL-6.

Example 2: Plasmonic-Fluor Linked Immunosorbent Assay (p-FLISA) on the Microneedle Patch Conventional sandwich enzyme linked immunosorbent assay (ELISA) involves an enzymatic reaction that results in the formation of a soluble colored product in an analyte concentration-dependent manner. While highly standardized and routinely implemented in microtiter plates comprised of identical sampling wells, this approach is unsuitable for the microneedle patches due to (i) the relatively low sensitivity stemming from the limited sampling surface area (analyte present only on the micro-sized needles in real sampling situation), making the quantification of low-abundant analytes challenging; and (ii) the soluble nature of the colored product, which masks spatial variations in the amount of analyte bound across the patch, eliminating the possible spatial multiplexing capability. Hence, existing approaches are limited to pseudo mouse models involving high amounts of target analytes, which do not represent their true pathological and physiological concentrations. To overcome these challenges, a novel fluorophore-linked immunosorbent assay (FLISA) is described herein that relies on a "plasmonic-fluor" as an ultrabright and highly specific fluorescent nanolabel. Plasmonic-fluor is comprised of a gold nanorod coated with fluorophores (800CW) and a universal biological recognition element (e.g. biotin). BSA is employed as a scaffold to assemble all of these functional elements as well as to resist non-specific binding (FIG. 18, 19A-B, see Material and Methods below for detailed description of plasmonic-fluor). Plasmonic-fluor is comprised of a plasmonic core (gold nanorod (AuNR)), a polymer spacer layer, fluorophores, and a universal biorecognition element (biotin), which are assembled using BSA. Siloxane copolymer is employed as a spacer layer between the gold nanorod and the fluorophores to avoid metal-induced fluorescence quenching. TEM images of the plasmonic-fluor confirmed the presence of a thin organic layer around the AuNRs (polymer and BSA conjugate) with an overall thickness of ~6.3±1.1 nm (FIG. 20, 21A-B). Binding of plasmonic-fluor-800CW to strepdavidin-800CW coated at the bottom of a microtiter well resulted in a 1424-fold enhancement in the ensemble fluorescence intensity (FIG. 22, 23).

Figure 24:
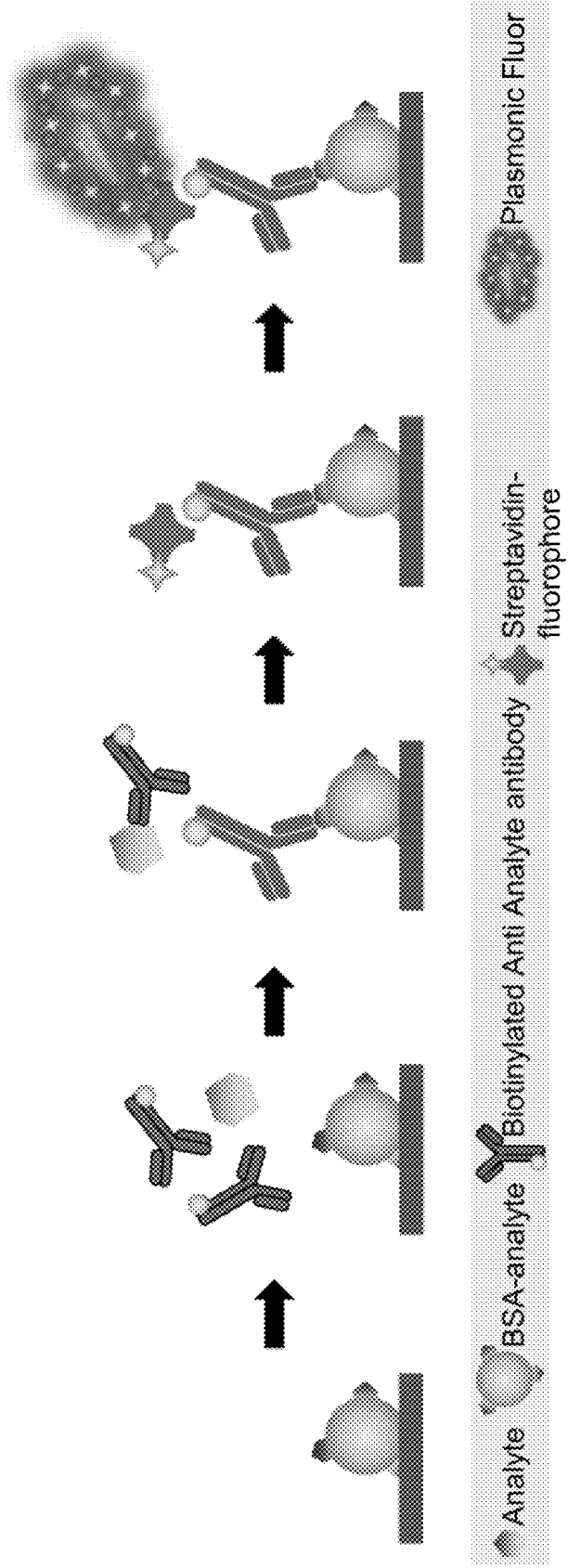
FIG. 24 is an exemplary embodiment of plasmonic-fluor for a conventional competitive assay in accordance with the present disclosure.
Figure 27B:
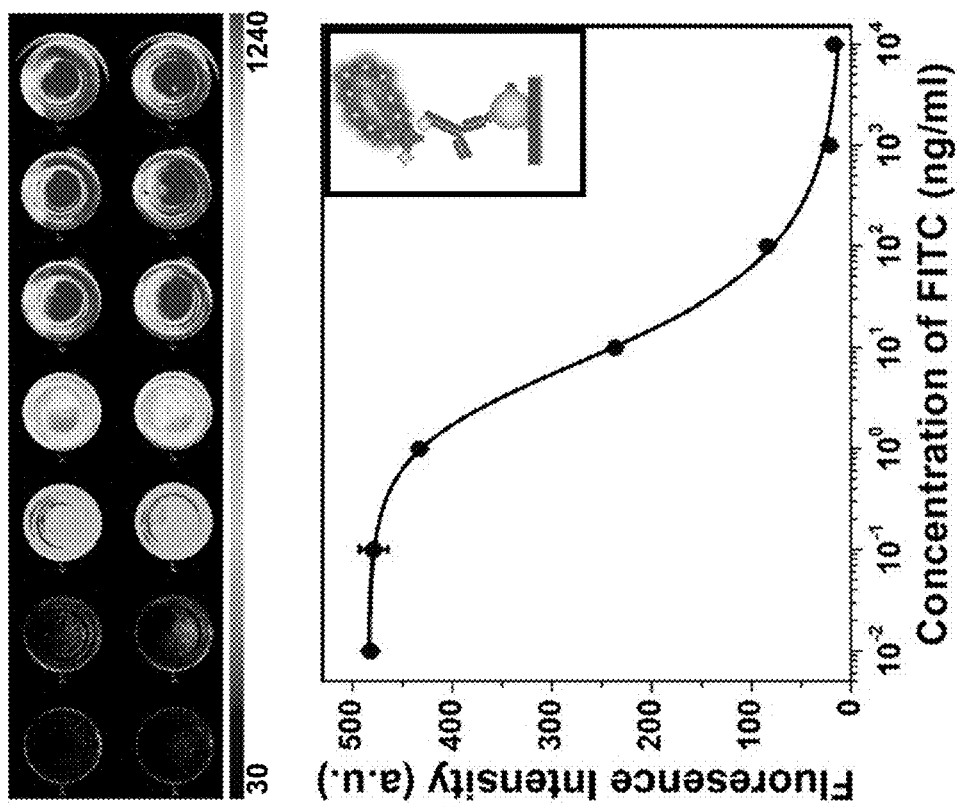
FIG. 27B is an exemplary embodiment of FITC detection with plasmonic-fluor-CW800 (PFLISA) in accordance with the present disclosure.
Figure 27A:
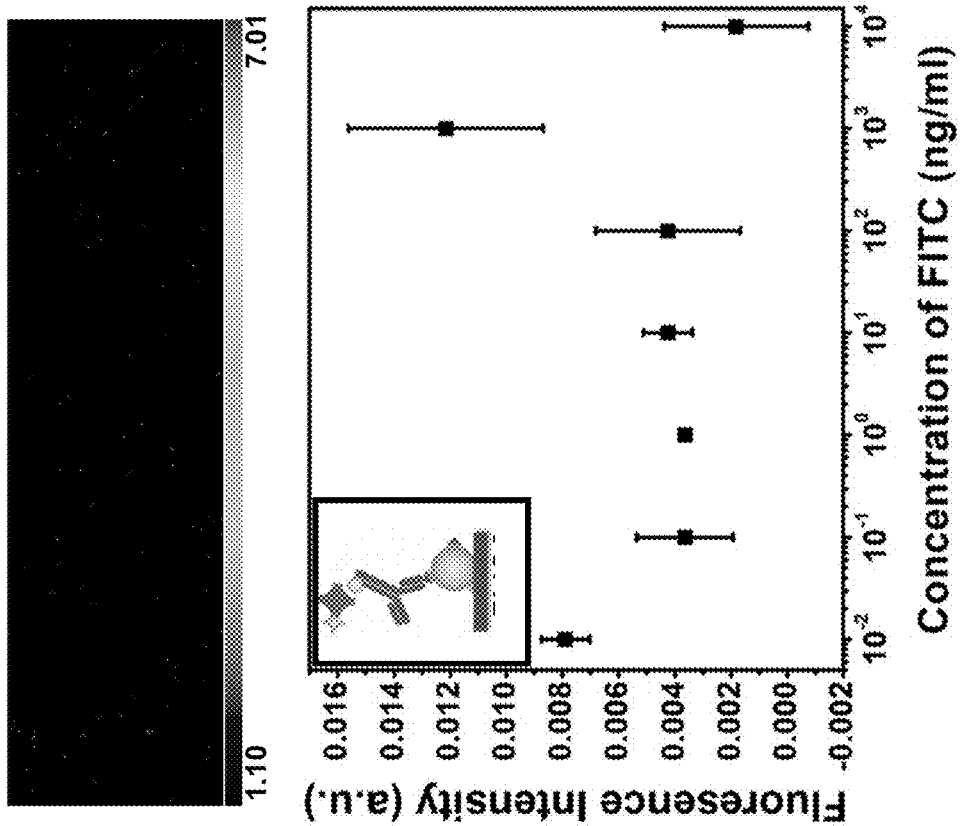
FIG. 27A is an exemplary embodiment of FITC (fluorescein isothiocyanate) detection with fluor-CW800 (FLISA) in accordance with the present disclosure.
Figure 28:
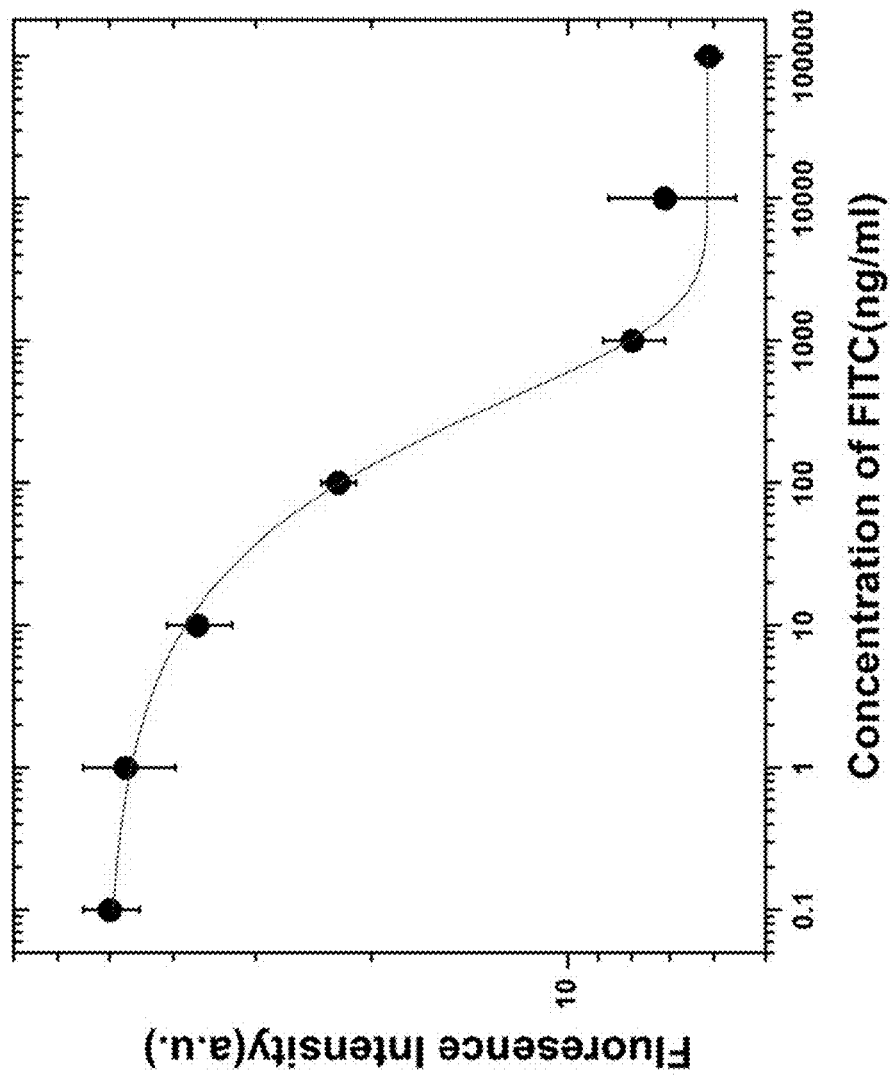
FIG. 28 is an exemplary embodiment of a 30 minute quick assay for FITC detection in accordance with the present disclosure.
Figure 29B:
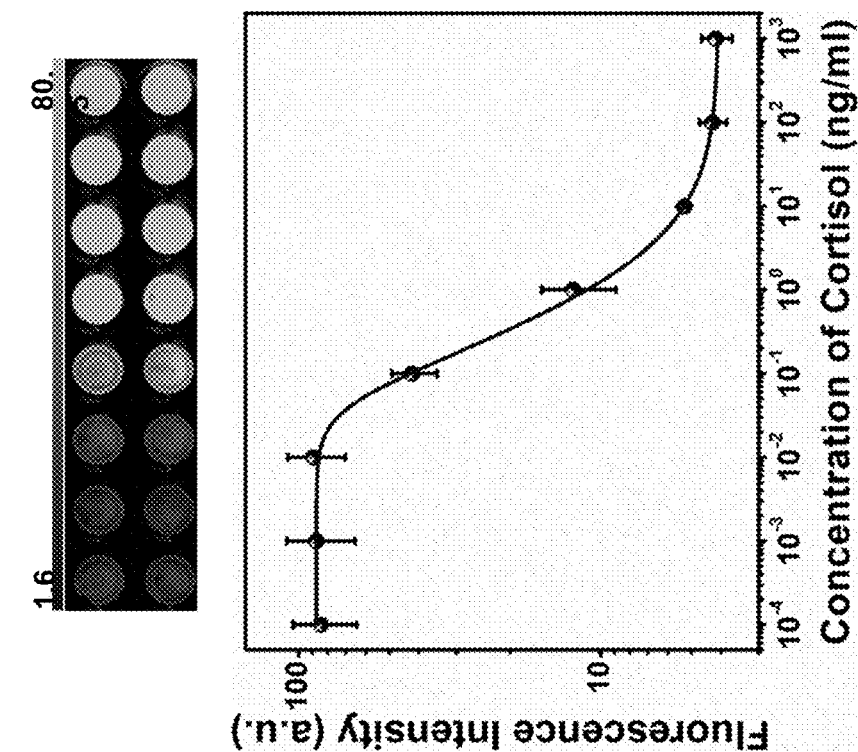
FIG. 29B is an exemplary embodiment of PFLISA detection of cortisol in accordance with the present disclosure.
Figure 29A:
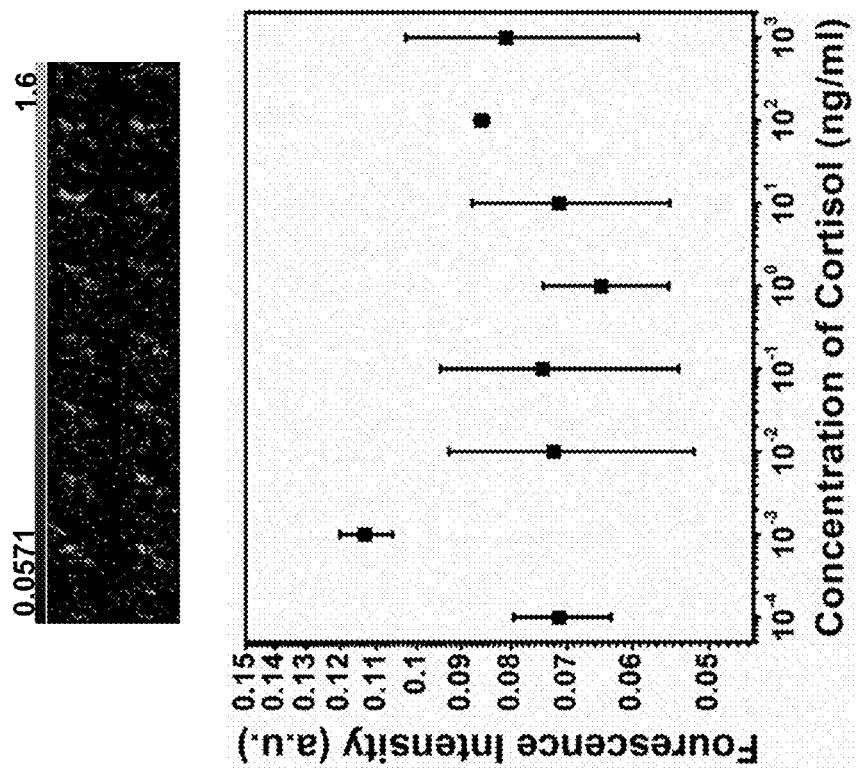
FIG. 29A is an exemplary embodiment of FLISA detection of cortisol in accordance with the present disclosure.
Figure 30:
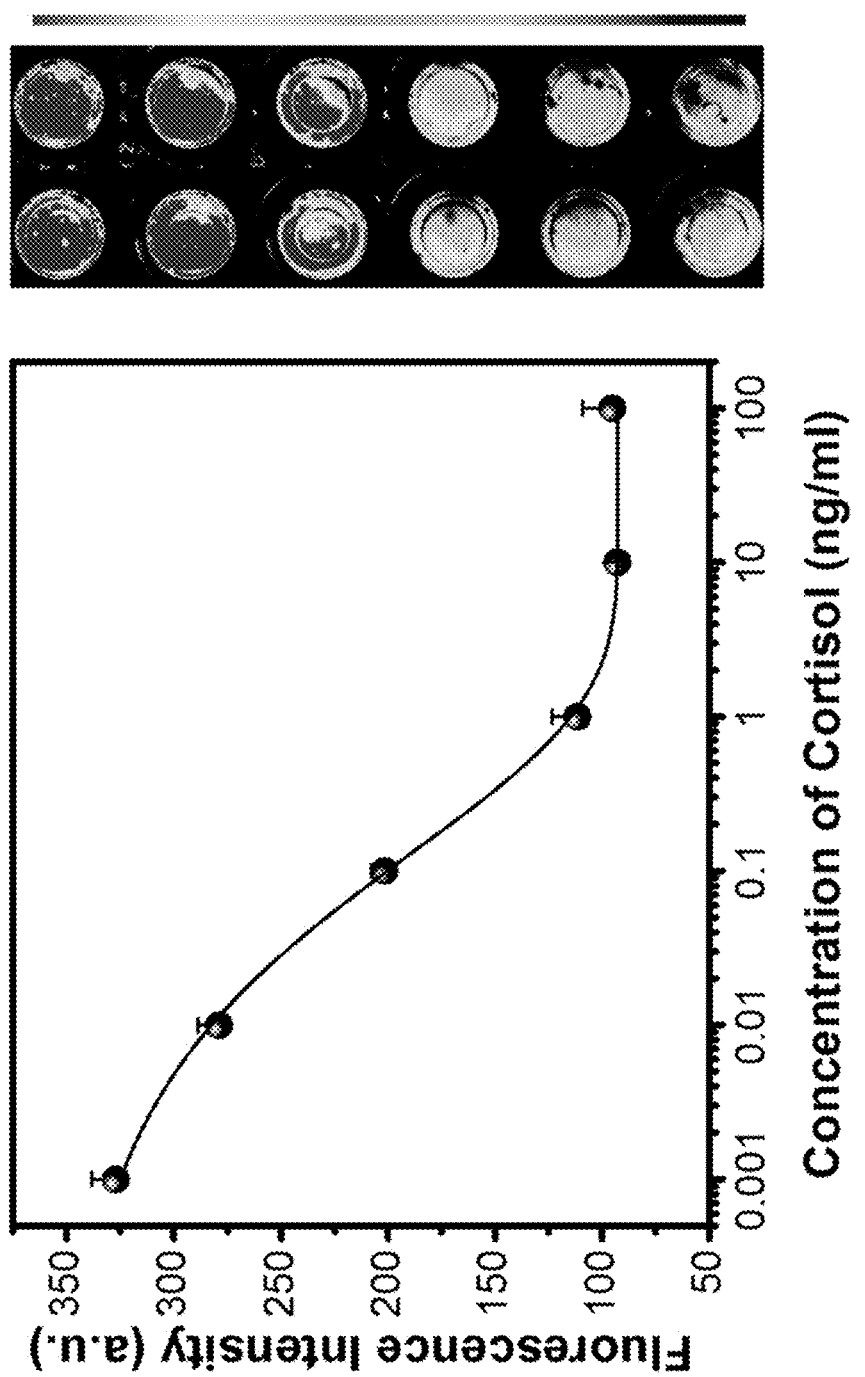
FIG. 30 is an exemplary embodiment of cortisol detection in accordance with the present disclosure.
Figure 31:
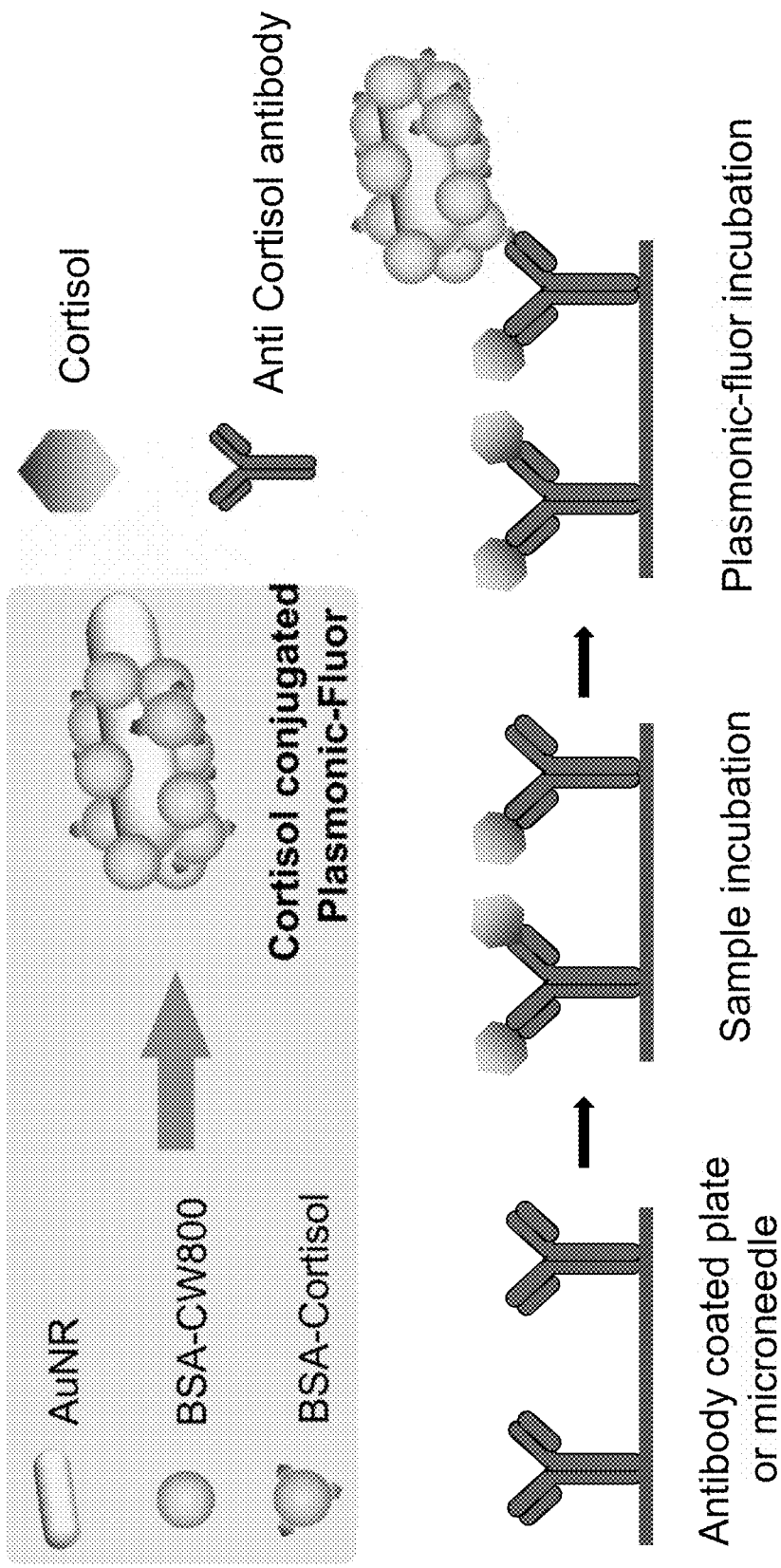
FIG. 31 is an exemplary embodiment of a plasmonic-fluor for a novel competitive assay in accordance with the present disclosure.
Figure 33:
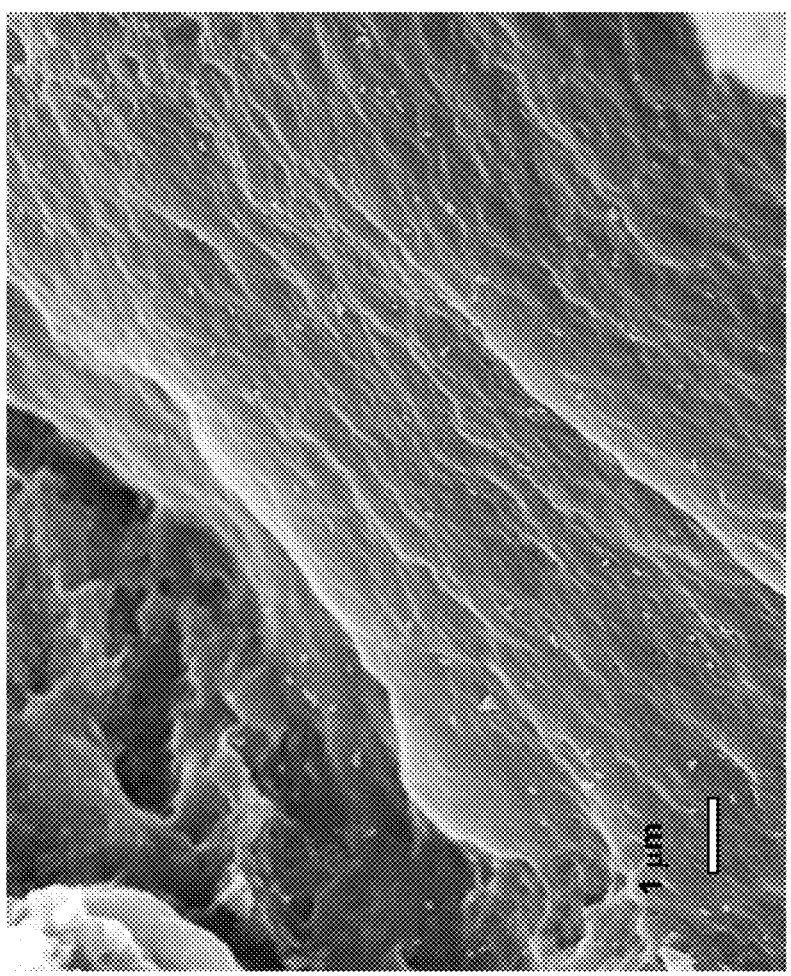
FIG. 33 is an exemplary embodiment of a zoomed-out SEM image showing the polystyrene surface of a microneedle after being probed by plasmonic-fluor in accordance with the present disclosure.
Figure 34:
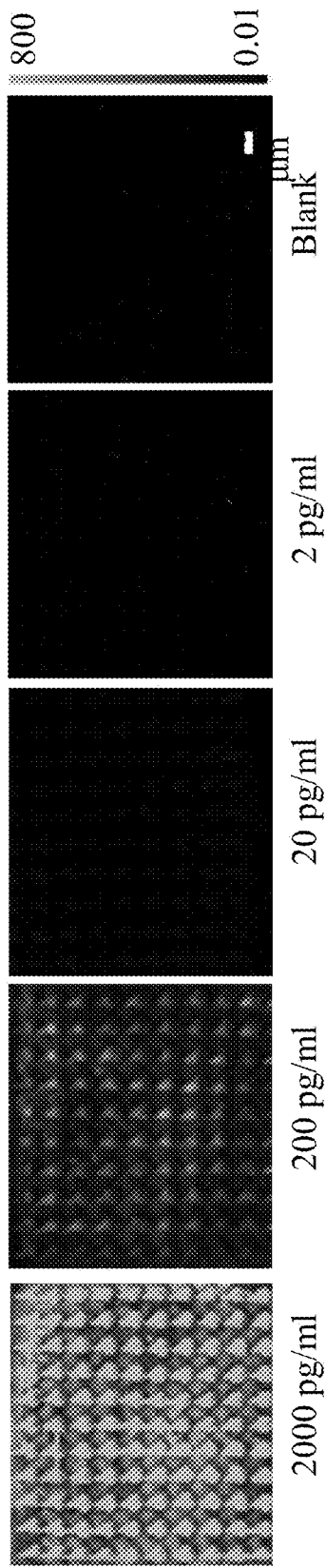
FIG. 34 is an exemplary embodiment of representative fluorescence microscopy images of plasmonic-fluor enhanced FLISA implemented on microneedle patch in accordance with the present disclosure.
Figure 35:
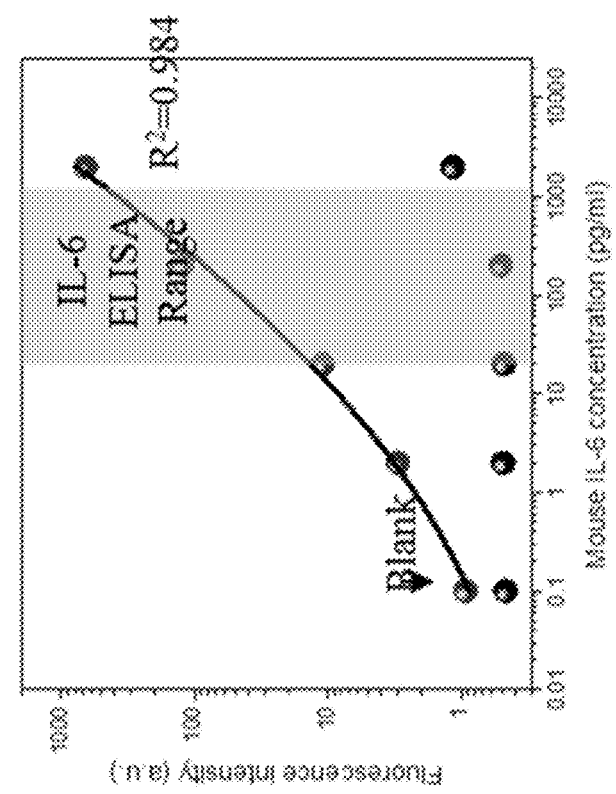
FIG. 35 is an exemplary embodiment of a plot showing IL-6 does dependent fluorescence intensity of ELISA implemented on microneedle patch from conventional and plasmonic-fluor enhanced ELISA in accordance with the present disclosure.

To test the applicability of plasmonic-fluor as an ultrabright biolabel for use on a microneedle patch, mouse interleukin 6 (IL-6), a pro-inflammatory cytokine, was employed as a representative protein biomarker. Conventional FLISA involves a standard sandwich immunoassay format of immobilizing the capture antibody on the surface of the microneedle, recognition and capture of analyte (IL-6), binding of biotinylated detection antibody to the captured analyte, exposure to streptavidin-fluorophore (800CW in this study), which binds to the biotin on the detection antibody with very high affinity. In contrast to conventional FLISA, plasmonic-fluor linked immunosorbent assay (p-FLISA) involves the use of plasmonic-fluor instead of a conventional fluorophore as the fluorescent label (FIG. 24). To determine the improvement in sensitivity and limit-of-detection (LOD, defined as mean+3σ of the blank) of p-FLISA compared to FLISA, serial dilutions of IL-6 of known concentration (2.5 ng/ml to 2.5 pg/ml) were employed as standards. Fluorescence signals obtained after applying the plasmonic-fluor-800CW revealed nearly 530-fold enhancement in the ensemble fluorescence intensity compared to the conventional FLISA at the highest IL-6 concentration tested (2.5 ng/ml) (FIG. 25, 26). FIGS. 27(A-B) and 28 show fluorescence intensity with varying concentrations of FITC. FIGS. 29(A-B) and 30 show fluorescence intensity with varying concentrations of cortisol, according to the novel assay illustrated in FIG. 31. Scanning electron microscopy (SEM) images revealed the presence of plasmonic-fluors on the surface of the microneedle (FIGS. 32 and 33, showing plasmonic-fluors highlighted by arrows in FIG. 32). FIGS. 34 and 35 demonstrate that plasmonic-fluor enhanced immunoassay was performed on microneedle patches, exhibiting broader dynamic range and lower detection limit compared to traditional ELISA.

Figures 36, 37, 38:
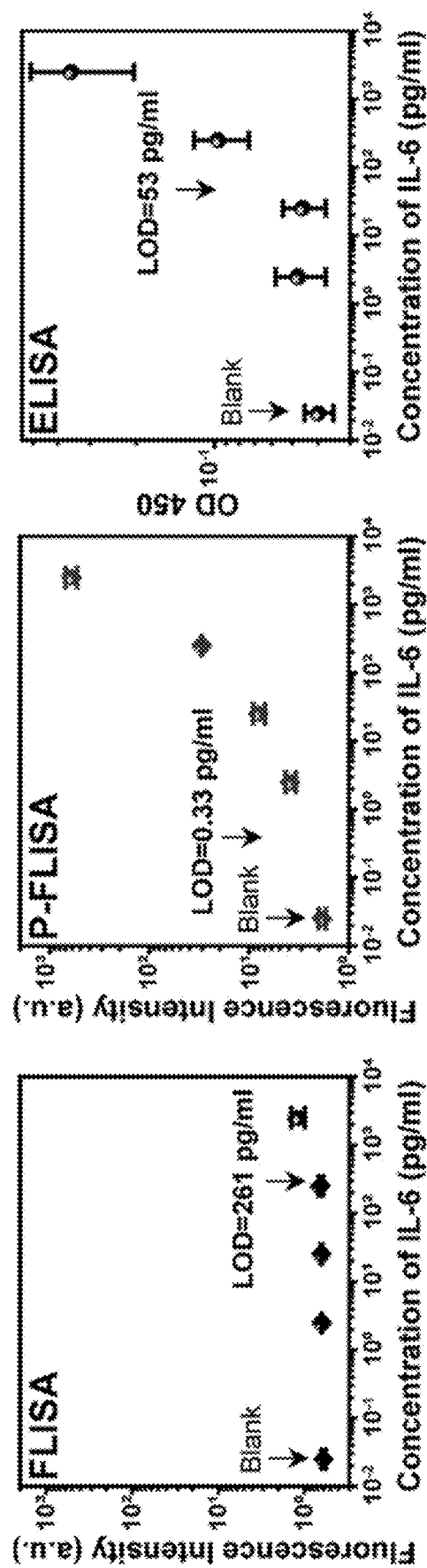
FIG. 36 is an exemplary embodiment of plots showing the IL-6 dose-dependent fluorescence intensity on microneedle from conventional FLISA in accordance with the present disclosure. Error bars represent standard deviation. N=3 repeated tests.
FIG. 37 is an exemplary embodiment of plots showing the IL-6 dose-dependent fluorescence intensity on microneedle from p-FLISA in accordance with the present disclosure. Error bars represent standard deviation. N=3 repeated tests.
FIG. 38 is an exemplary embodiment of a plot showing IL-6 dose-dependent optical intensity of ELISA implemented on microneedle in accordance with the present disclosure. Error bars represent standard deviation, N=3 repeated tests.
Figures 39A, 39B:
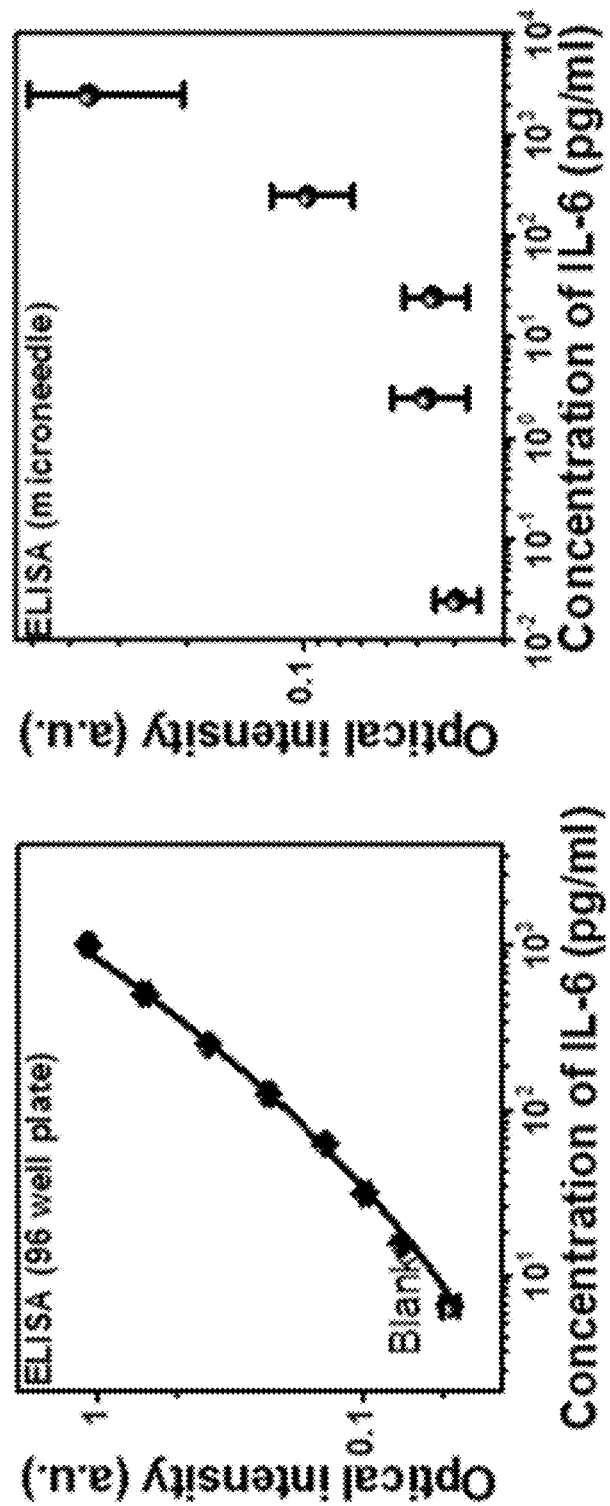
FIG. 39A is an exemplary embodiment of mouse IL-6 ELISA implemented on a standard 96-well plate in accordance with the present disclosure.
FIG. 39B is an exemplary embodiment of mouse IL-6 ELISA implemented on microneedle patch in accordance with the present disclosure.

Remarkably, the LOD of the IL-6 p-FLISA was found to be around 0.33 pg/ml, which is 790-fold lower compared to conventional FLISA (261 pg/ml) (FIG. 36, 37). On the other hand, ELISA performed on the microneedle exhibited weak colorimetric signal and large standard deviation (FIG. 38). The optical density corresponding to the highest IL-6 concentration of ELISA on microneedle patch is nearly 10-fold lower than the standard ELISA implemented on a microtiter plate, approaching the background noise level (FIG. 38, 39A-B). In other words, the optical intensity in standard ELISA is around 10-fold higher than that implemented on the microneedle patch. The LOD of ELISA on the microneedle patch was measured to be around 53 pg/ml, which is 160-fold higher than that of p-FLISA (0.33 pg/ml) (FIG. 37, 38).

Example 3: Biophysicochemical Properties of Microneedle Patches

Figure 41:
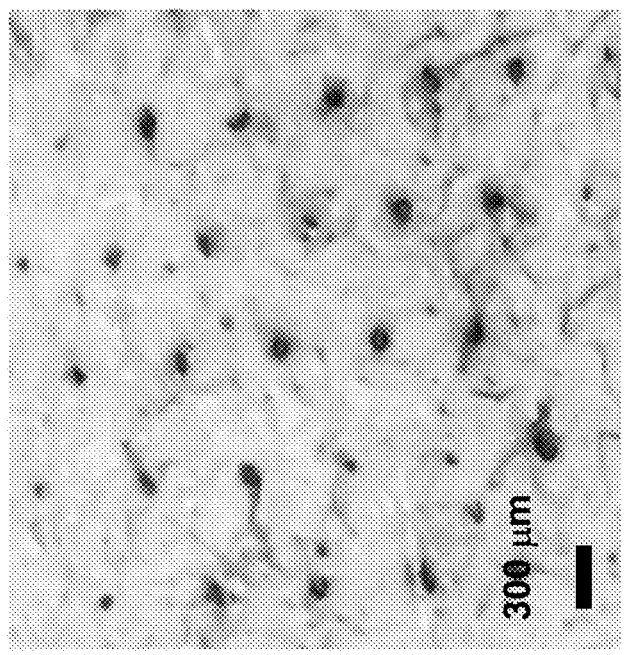
FIG. 41 is an exemplary embodiment of polystyrene microneedle penetration of mouse skin in accordance with the present disclosure.
Figure 40:
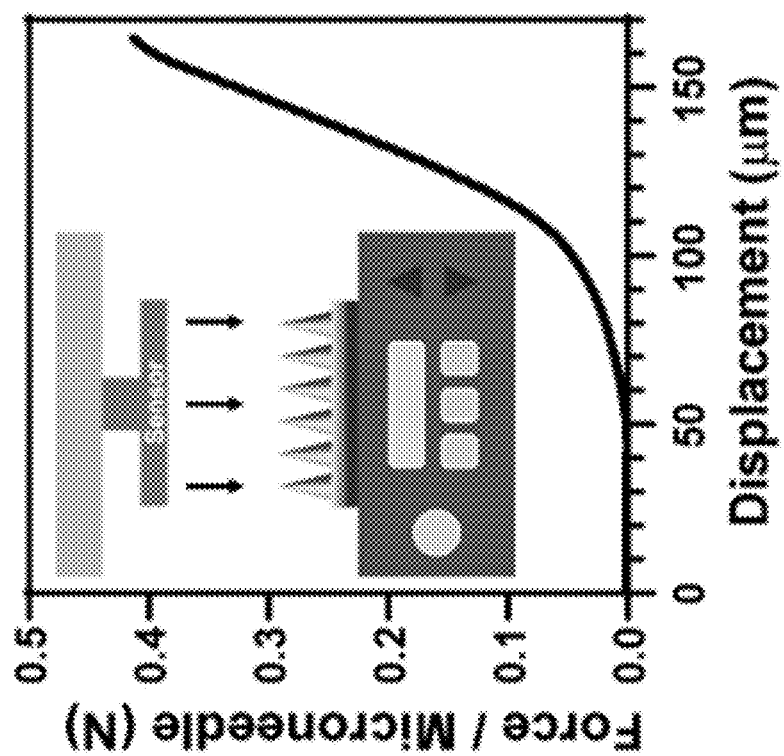
FIG. 40 is an exemplary embodiment of mechanical behavior for the microneedle patches under normal compressive load and schematic illustration of experimental setup (inset) in accordance with the present disclosure.
Figure 42:
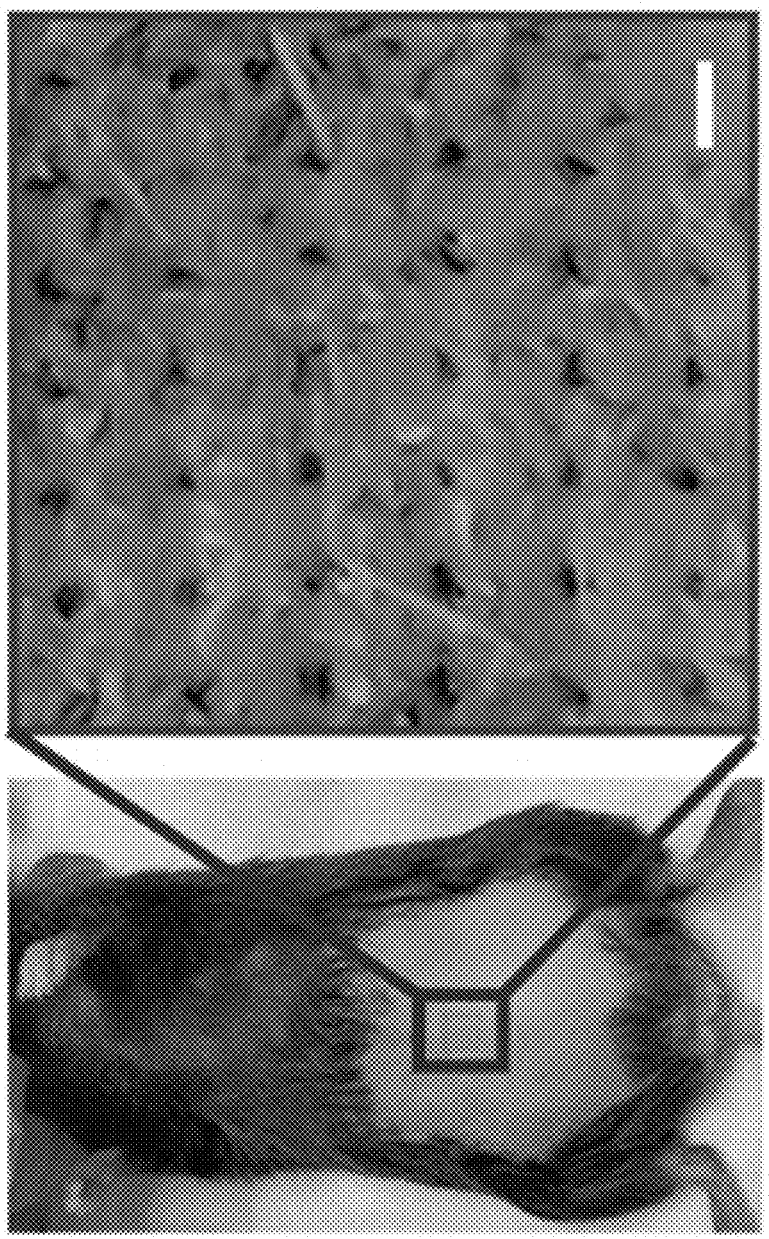
FIG. 42 is an exemplary embodiment of mouse ventral skin administered with microneedle patch (left) and optical image of trypan blue staining showing the indents caused by the penetration of microneedle on mouse skin (right) in accordance with the present disclosure. Scale bar 500 mm.

Before deploying the microneedle patches for in vivo transdermal biodetection, their biophysicochemical properties were investigated, such as (i) mechanical strength for successful penetration of dermal tissue; (ii) biocompatibility; and (iii) biosafety and potential side effects. To determine if the polystyrene microneedles possess sufficient mechanical strength to penetrate the skin under compression, a micro-compression test was performed on a microneedle patch comprised of an 11×11 array of microneedles. The microneedle patch tolerated compression force >0.4 N/microneedle, which is sufficiently high to puncture the skin without causing the microneedles to mechanically yield (FIGS. 40 and 41). The microneedles successfully penetrated the mouse skin, as evidenced by Trypan blue staining (FIG. 42).

Figure 43:
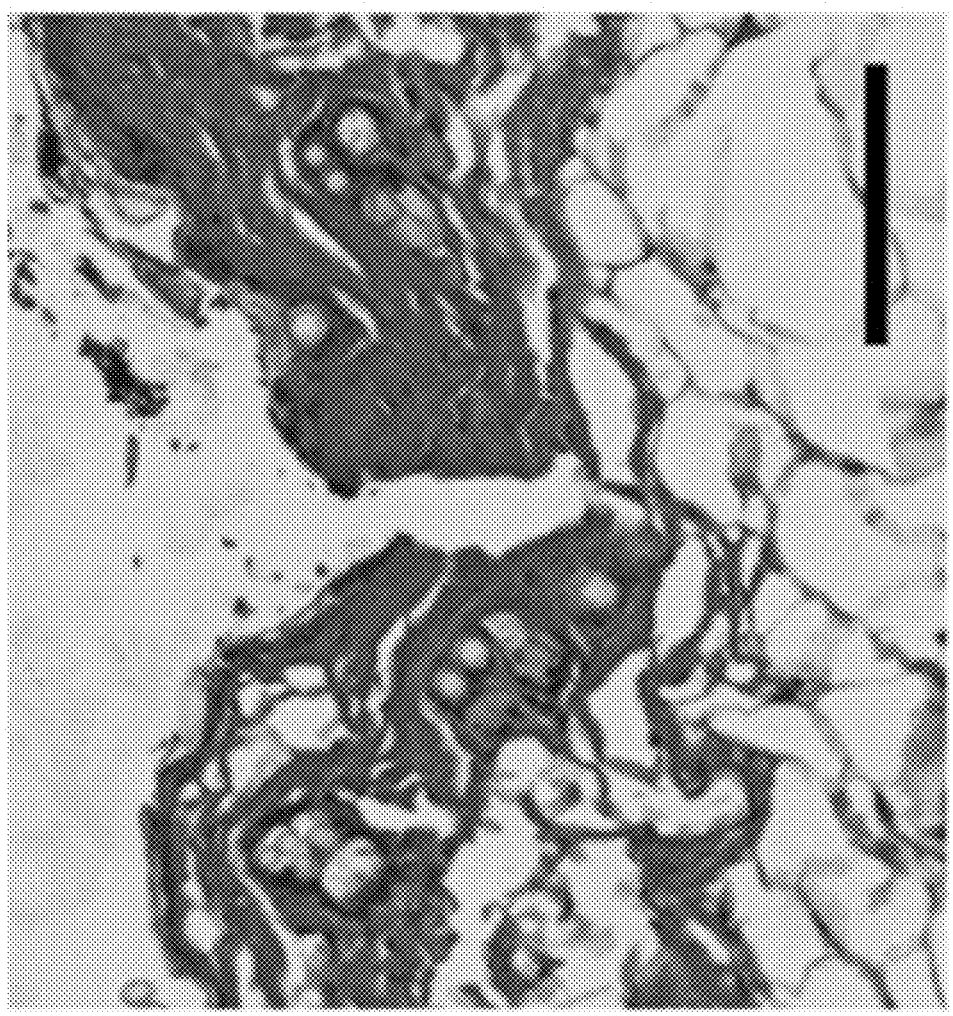
FIG. 43 is an exemplary embodiment of H&E stained section of mouse skin showing the successful penetration of a single microneedle in accordance with the present disclosure. Scale bar 100 mm.
Figure 44B:
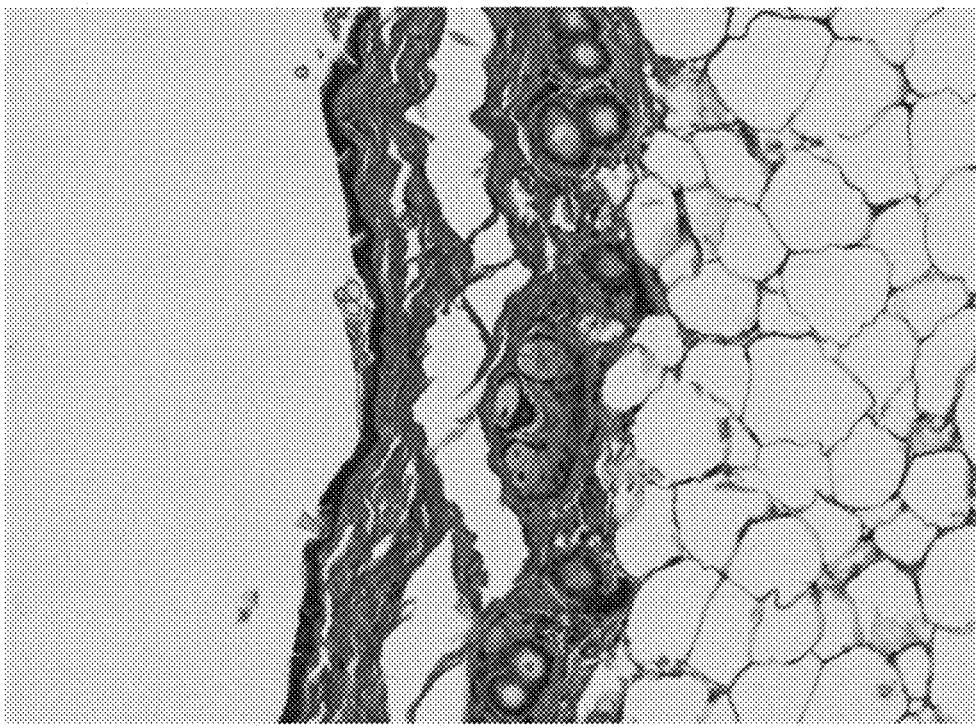
FIG. 44B is an exemplary embodiment of H&E staining of mouse dermis and epidermis layer with microneedle administration in accordance with the present disclosure. Scale bar 100 μm.
Figure 44A:
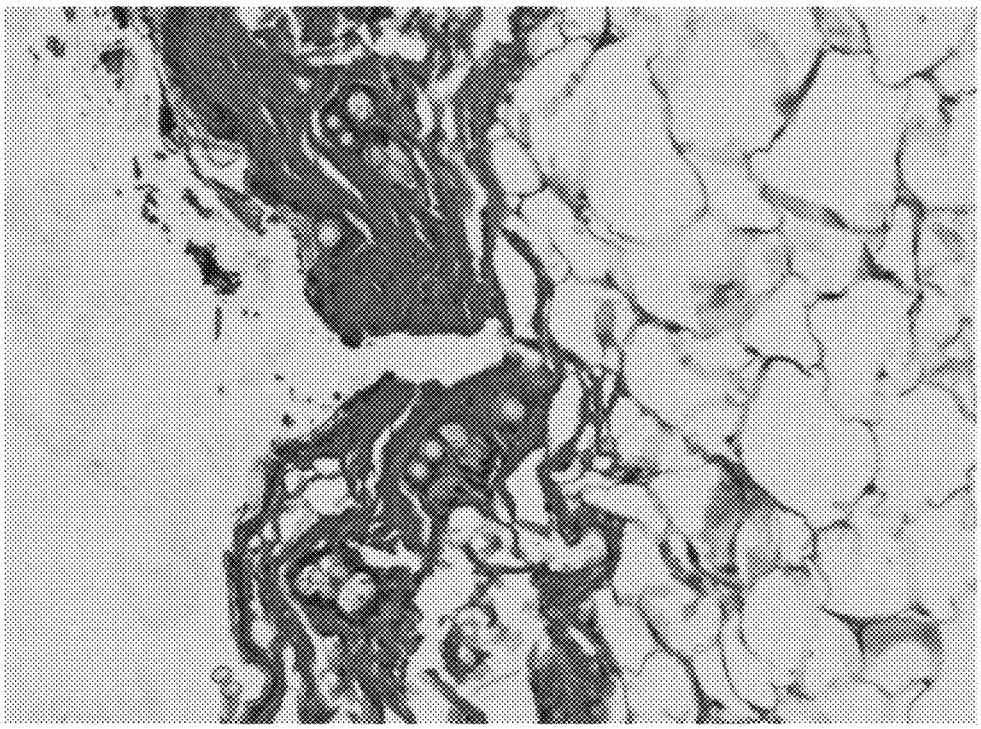
FIG. 44A is an exemplary embodiment of H&E staining of mouse dermis and epidermis layer without microneedle administration in accordance with the present disclosure.
Figure 46:
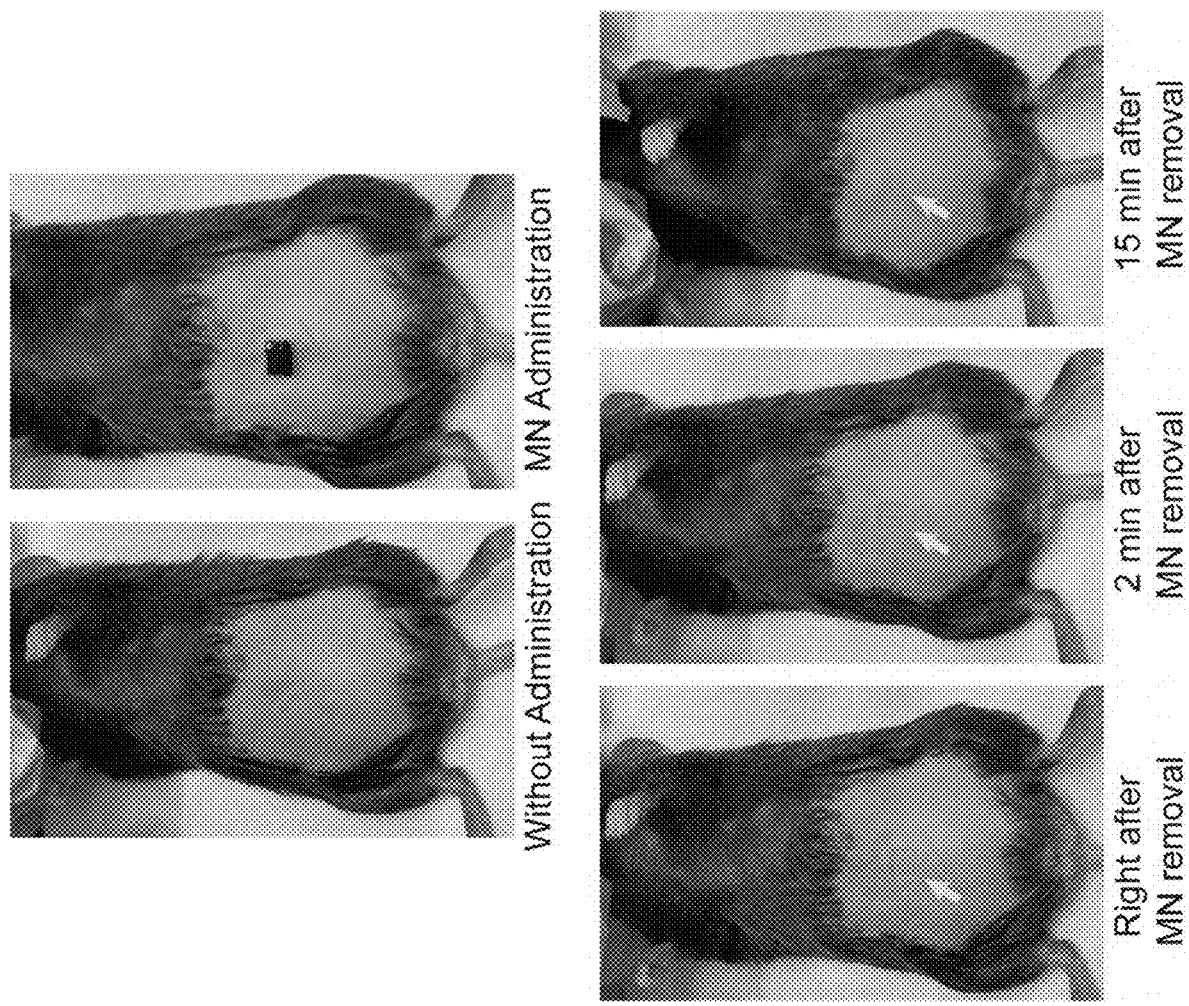
FIG. 46 is an exemplary embodiment of optical images showing that micro-indents on mouse skin caused by the administration of the microneedle patch quickly recovered in 15 minutes (administration site is indicated by arrow) in accordance with the present disclosure.

Hematoxylin and eosin (H&E) staining of the extracted mouse skin tissue further confirmed that the microneedles have successfully penetrated the stratum corneum and perforated into the epidermal layer (FIG. 43, 44A-B). SEM images indicated that the microneedles maintained their conical shape and sharp tips after removal from the mouse skin, which further confirms their mechanical integrity during administration (FIG. 45A-D). Furthermore, micro-indents on skin caused by the application of the microneedle patch quickly became invisible as the skin recovered to the normal state within 15 minutes (FIG. 46). The rapid recovery of the skin re-affirms the minimally-invasive nature of the procedure compared to conventional techniques such as blood collection.

Figure 47:
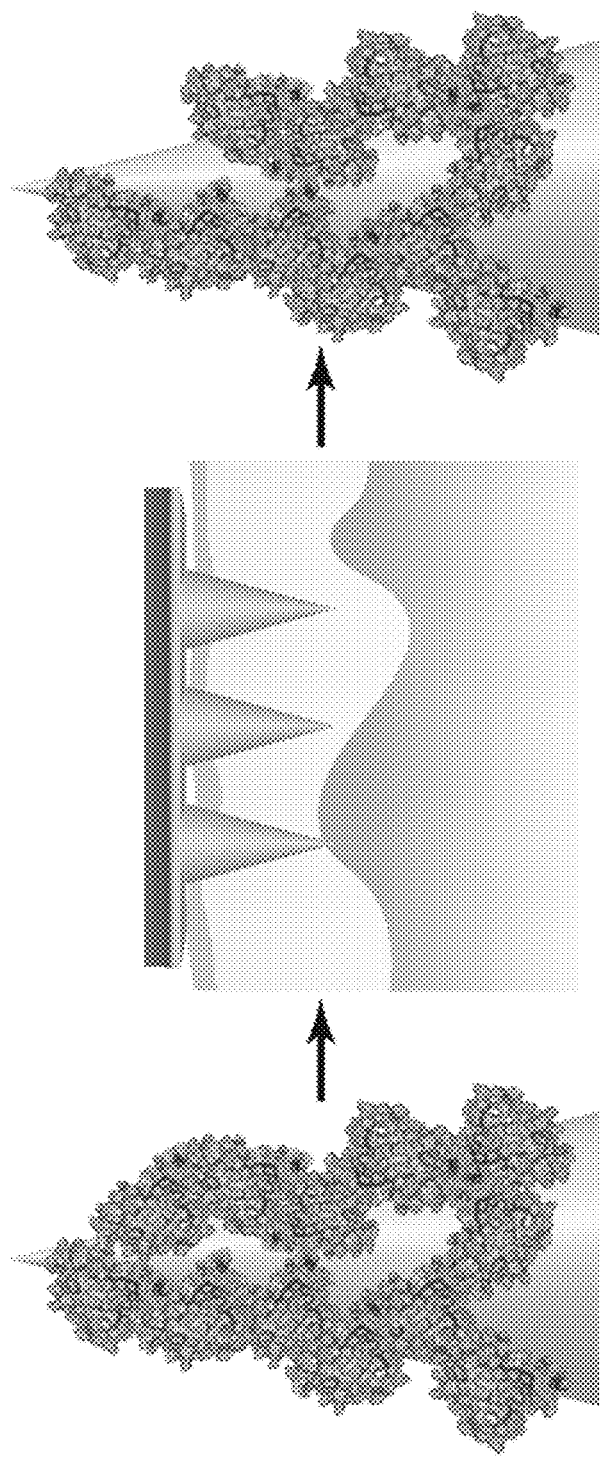
FIG. 47 is an exemplary embodiment of a schematic illustration demonstrating small loss of protein after the administration of microneedles on mouse skin in accordance with the present disclosure.
Figure 48:
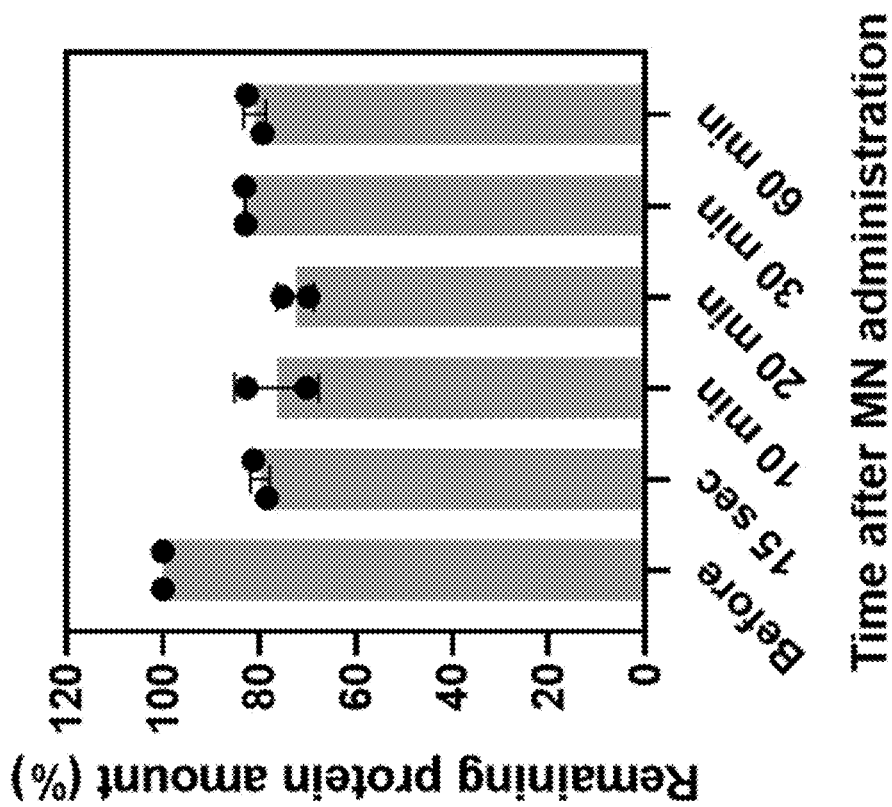
FIG. 48 is an exemplary embodiment of normalized amounts of protein left on the microneedles after different durations of administration of the patches in mice skin in accordance with the present disclosure.

Considering that the antibodies are immobilized on the microneedles, it is important to understand the stability of these proteins during the sampling process, i.e., during the penetration of the microneedles into the dermal tissue, residence in the dermal tissue, and subsequent withdrawal (FIG. 47). To test this, microneedles were coated with fluorescently labelled BSA (employed as a model protein) prior to application onto mouse skin for different durations (15 sec, 10, 20, 30 and 60 mins). Upon withdrawal, microneedles exhibited a ~20% loss in fluorescence intensity, indicating that a small fraction of proteins desorbed from the microneedles, possibly due to the shear forces between the microneedle surface and the epidermis (FIG. 48). Considerably, the decrease in the fluorescence intensity (representing the amount of protein lost) did not depend on the residence time of the microneedles in the dermal tissue, indicating minimal loss from desorption or proteolytic degradation of these proteins in the dermal tissue, even for a residence time of 60 minutes. That is, no significant difference in loss was observed between 15 sec after and 60 min after administration time, showing that post administration degradation was very limited. Major loss of protein occurred at the moment of administration.

Figure 49:
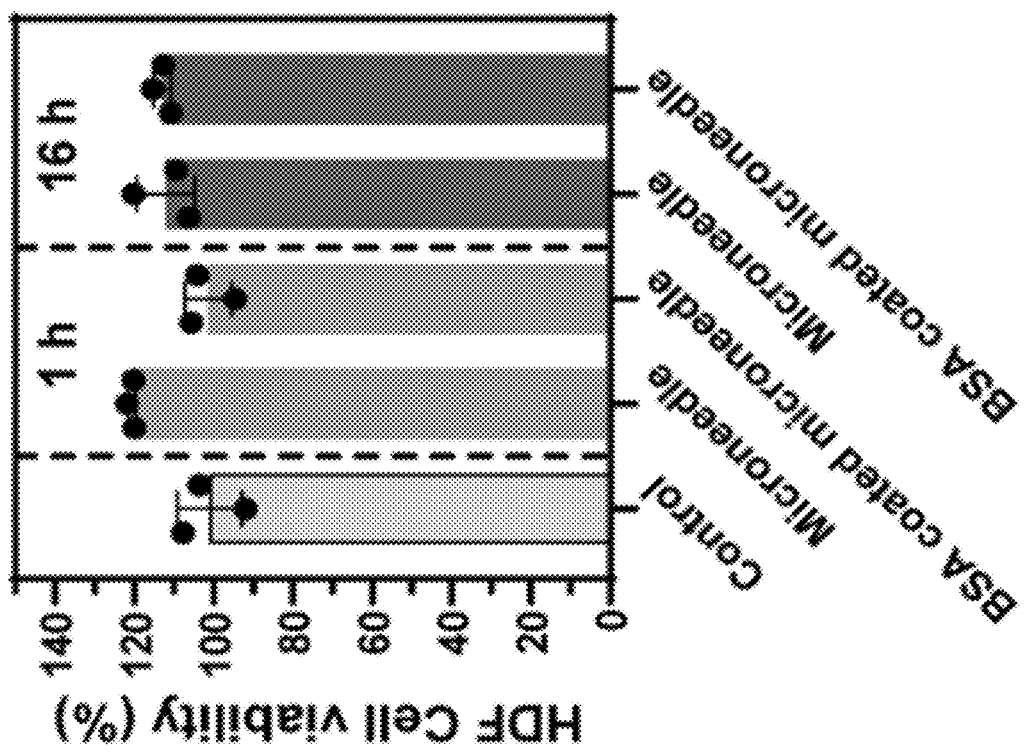
FIG. 49 is an exemplary embodiment of cell viability of human dermal fibroblast cells (HDF cells) co-cultured with pristine and BSA coated microneedle patch for 1 hour and 16 hours in accordance with the present disclosure. Error bar represents standard deviation, N=3 repeated tests.
Figure 50:
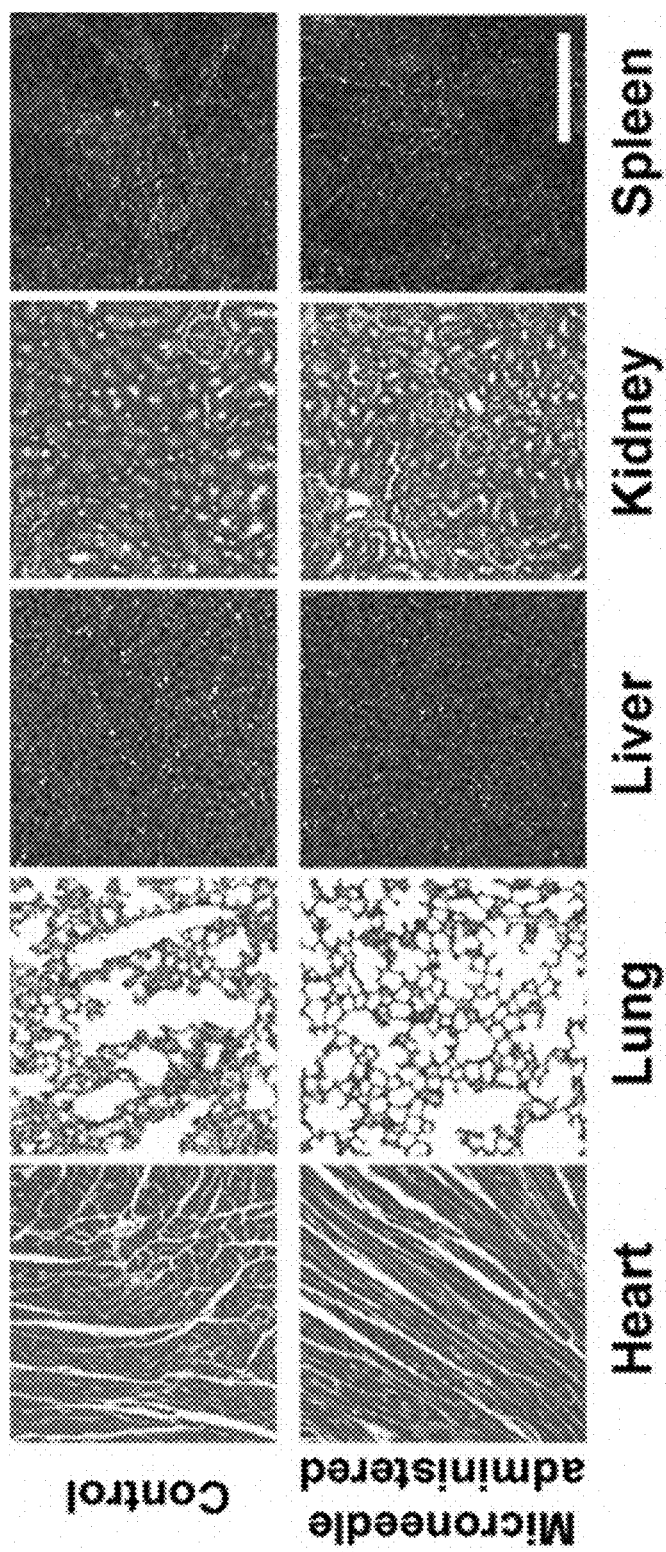
FIG. 50 is an exemplary embodiment of H&E stained section of mouse organs with and without administration of microneedle patch, indicating excellent biocompatibility of microneedle patch, scale bar 200 mm, in accordance with the present disclosure.
Figure 51:
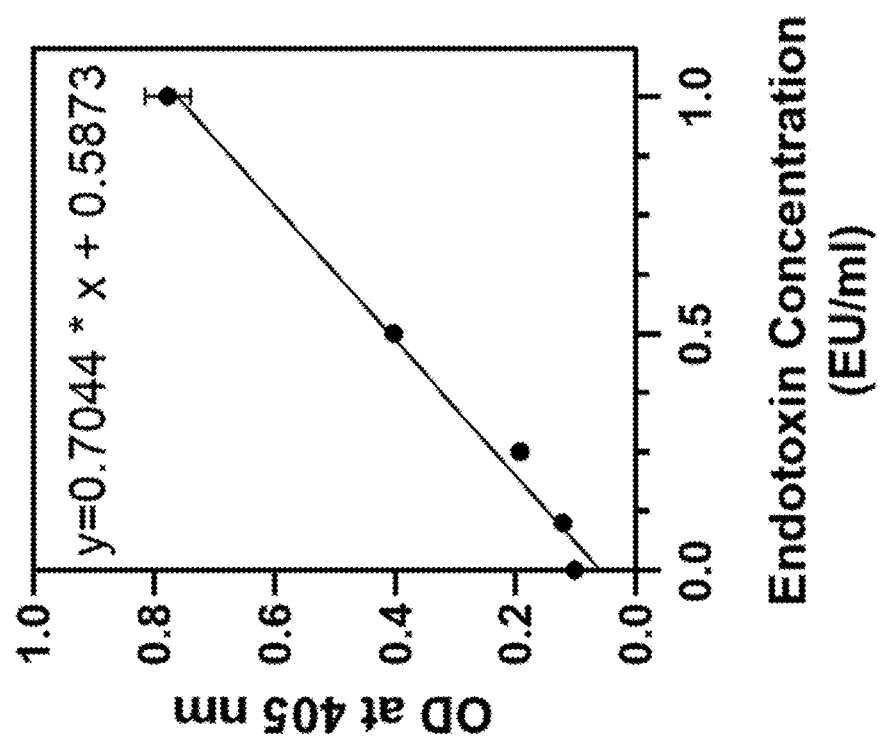
FIG. 51 is an exemplary embodiment of a standard curve of LAL Chromogenic Endotoxin Quantitation Kit in accordance with the present disclosure.

To evaluate the biocompatibility of the polystyrene microneedle patches, human dermal fibroblasts (HDF), one of the major cell types in the dermis layer, were cultured in the presence of microneedles and BSA coated microneedles (since the in vivo sampling involves microneedles blocked with a dense layer of BSA). Notably, no change in cell viability was observed after either 1- or 16-hours of in situ culture with the microneedle patches (FIG. 49). Systemic toxicity of the microneedle patch was also investigated by H&E staining. Negligible changes in cell states between the control group and the microneedle administered group demonstrated the excellent biocompatibility of the microneedle (FIG. 50). In addition, the endotoxin level of the microneedle patch was measured to investigate the possibility of an unwanted immune response after administration. Microneedles coated with BSA exhibited negligible endotoxin levels compared to the limit set by the US Food & Drug Administration (20 EU/device) (FIG. 51, Tables 1 and 2).

TABLE 1

Endotoxin level of BSA coated microneedle versus FDA requirement.

| | Endotoxin level |
|---|---|
| MN-BSA | 0.06 ± 0.002 EU/ml |
| FDA Non-pyrogeic medical device | <20 EU/ml |

TABLE 2

Individual data point of endotoxin test for BSA coated microneedle.

| | OD 405 | Concentration (EU/ml) |
|---|---|---|
| Sample 1 | 0.1017 | 0.061 |
| Sample 2 | 0.0993 | 0.058 |
| Average | | 0.059 |

Taken together, these findings demonstrate that the biofunctionalized microneedle patch represents a safe material platform for in vivo biodetection.

Example 4: Detection of Cocaine-Specific Antibody (IgG) in an Immunized Mouse Model Cocaine overdose and cocaine use disorder (CUD), which currently do not have FDA-approved medications, remain a global medical and social problem. While a vaccine is a unique approach that does not directly address the underlying neurobiological mechanism behind CUD, cocaine vaccines that produce antibodies reduce the rate and quantity of drug entry into the brain and inhibit the psychoactive effects of the drug. Unlike other vaccines that confer prolonged protection, currently designed antidrug vaccines require frequent boosting to maintain the effective antibody levels. A recent study revealed that lack of pre-vaccination screening assays that predict the most effective vaccines or subjects amenable to vaccination is the major obstacle for clinical translation. Therefore, technologies that enable rapid and reliable testing of hapten-specific antibody titers in vaccinated subjects may aid rational vaccine design and provide screening tools to predict vaccine clinical efficacy against drugs of abuse. As disclosed herein, a simple, rapid, and non-invasive method is demonstrated for evaluating the efficacy of the cocaine vaccine using a microneedle patch.

Figure 52:
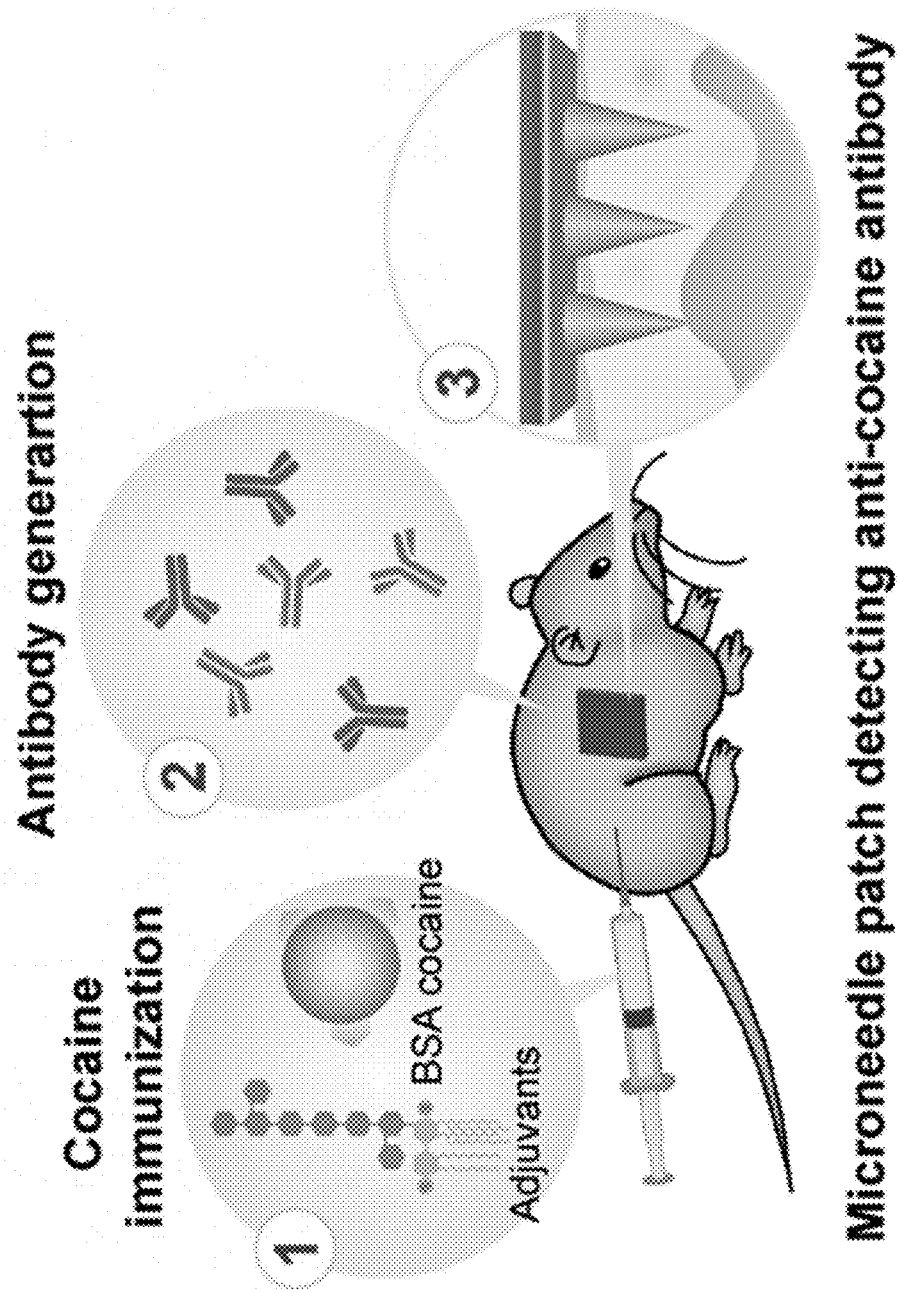
FIG. 52 is an exemplary embodiment of a schematic illustration showing the working principle of cocaine immunization, generation of BSA and cocaine-specific antibodies, and administration of the microneedle patch for the detection of specific antibodies in ISF in accordance with the present disclosure.
Figure 53:
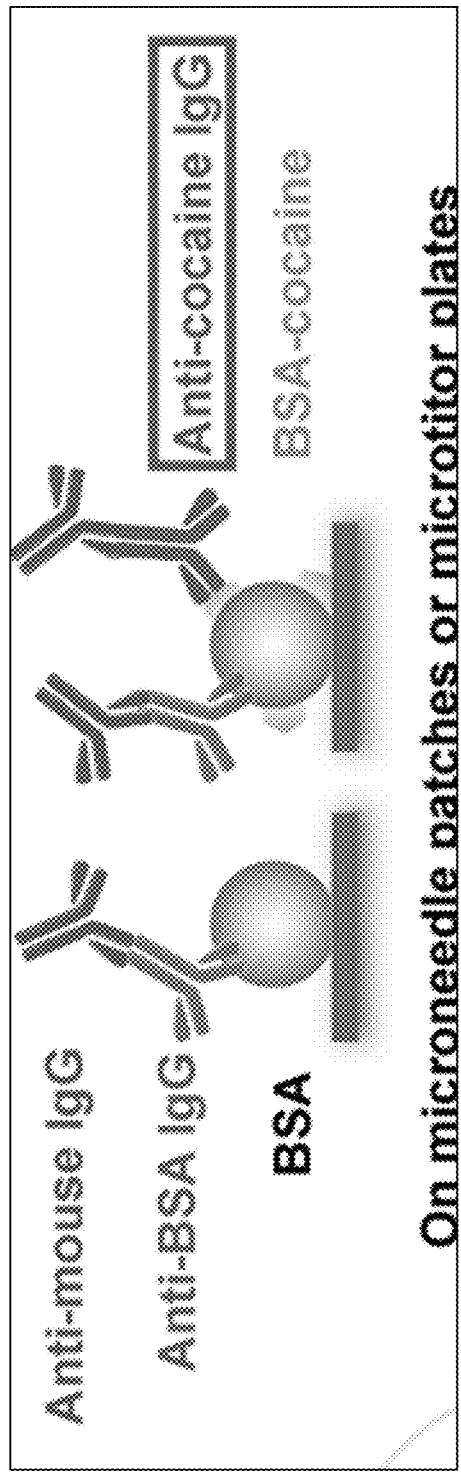
FIG. 53 is an exemplary embodiment of a schematic illustration demonstrating principle of anti-cocaine detection in accordance with the present disclosure.
Figure 54:
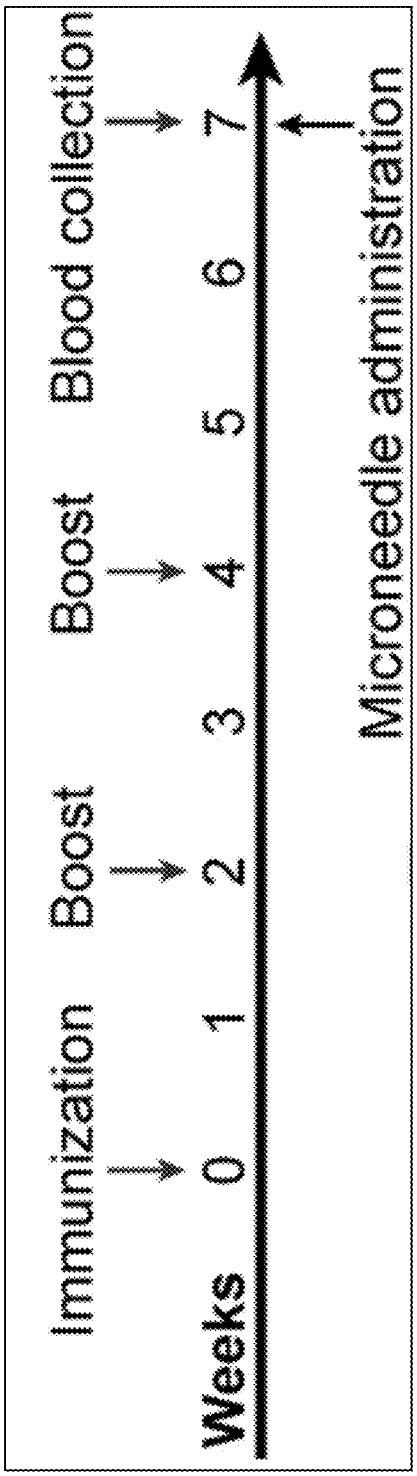
FIG. 54 is an exemplary embodiment of a workflow of immunization, blood draw and microneedle administration on mice in accordance with the present disclosure.
Figure 55:
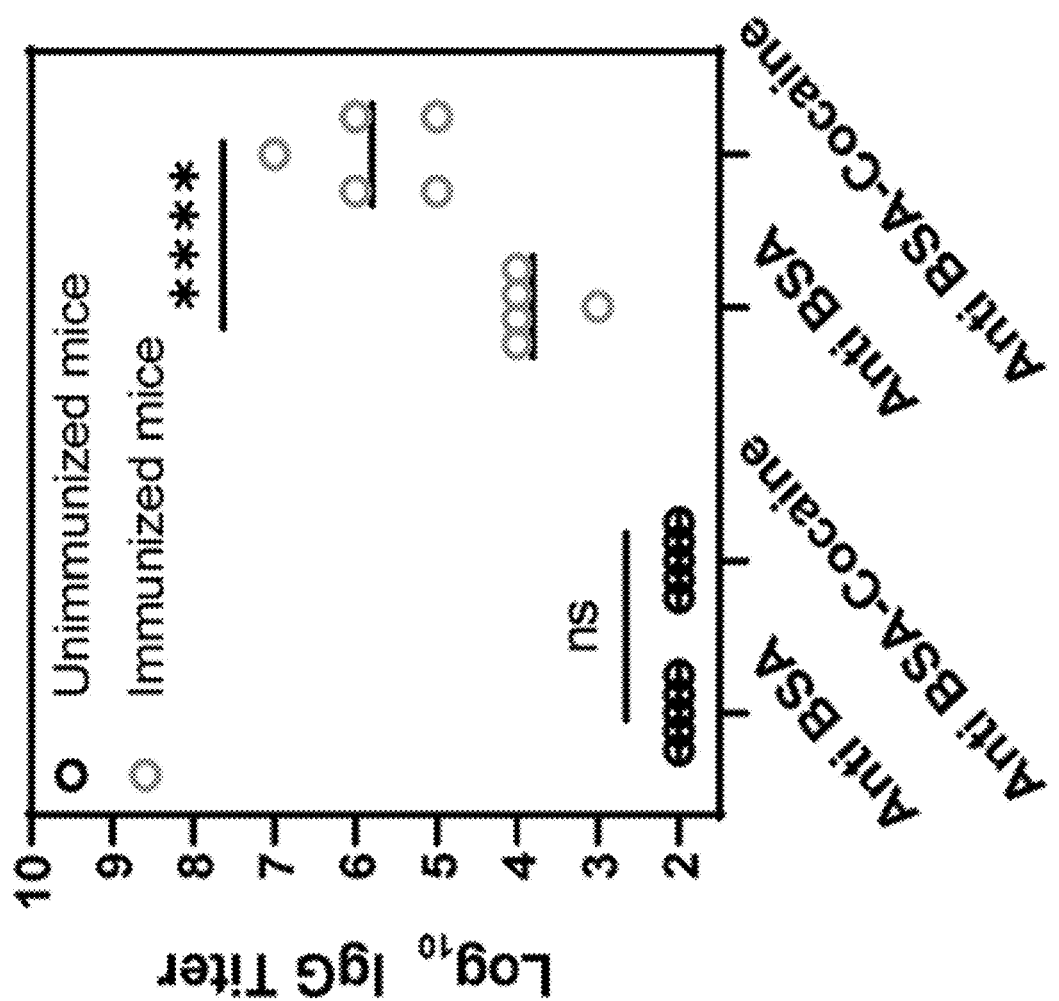
FIG. 55 is an exemplary embodiment of a plot depicting $log_{10}$ titer of anti-BSA and anti BSA-cocaine in mice serum from both immunized and unimmunized group, tested by "gold standard" ELISA in accordance with the present disclosure. N=5 mice in each group. Within unimmunized group, data statistically not significant (NS), P value >0.9999 by one-way ANOVA with Tukey's multiple-comparison test. Within immunized group, data statistically significant, **** P<0.0001 by one-way ANOVA with Tukey's multiple-comparison test.
Figure 56A:
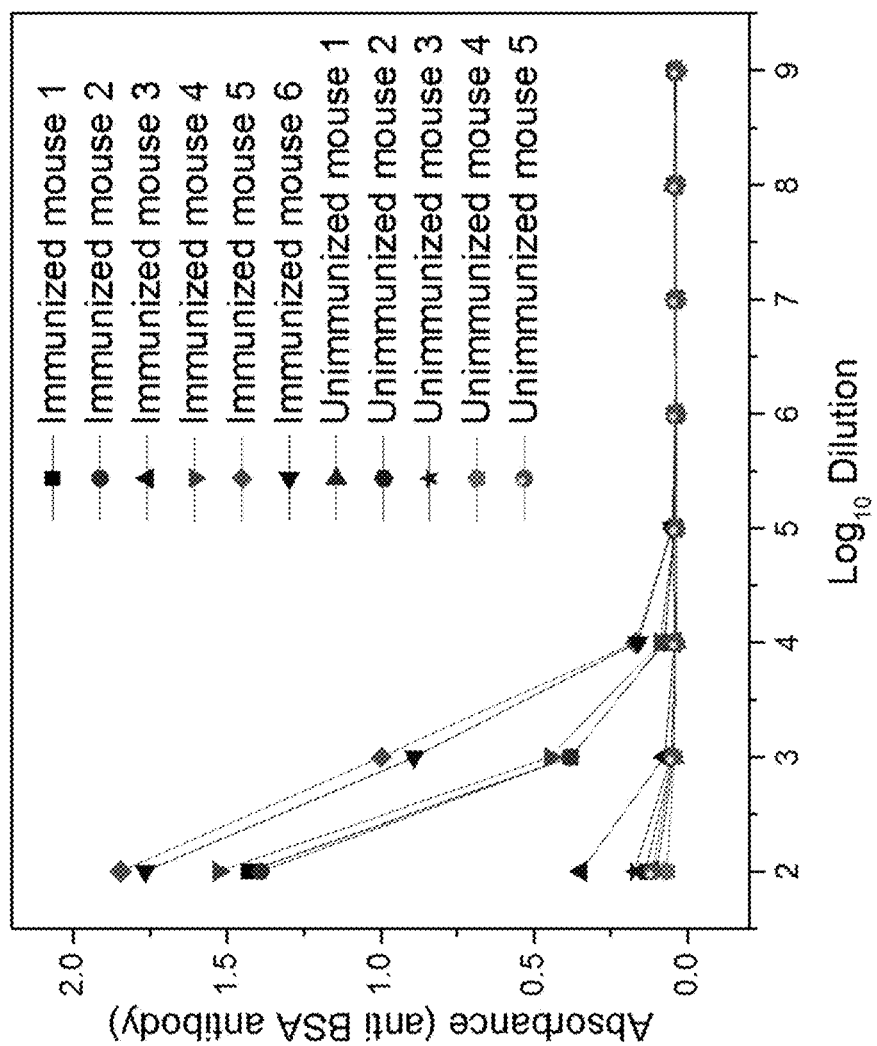
FIG. 56A is an exemplary embodiment of ELISA titer of (A) anti-BSA antibody in mice serum which have or have not been immunized with cocaine-BSA conjugate (tested with BSA coated plates) in accordance with the present disclosure.
Figure 56B:
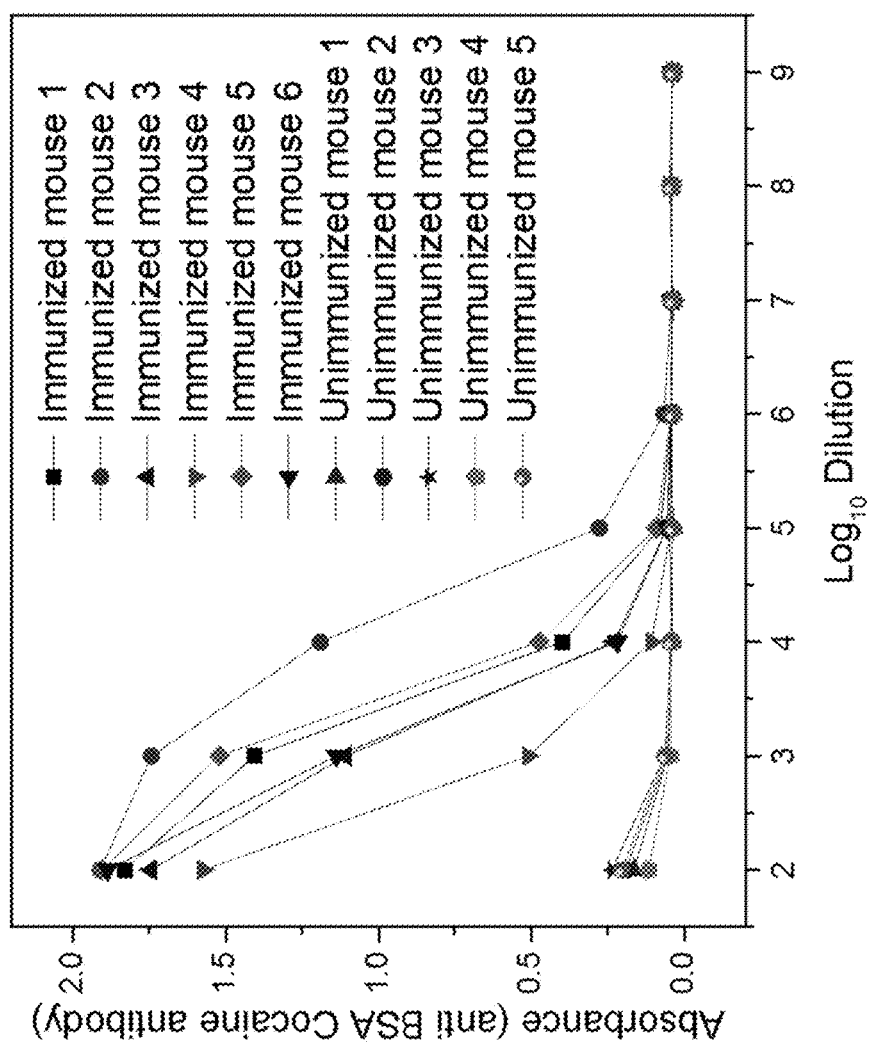
FIG. 56B is an exemplary embodiment of ELISA titer of anti-BSA-cocaine antibody in mice serum which have or have not been immunized with cocaine-BSA conjugate (tested with cocaine-BSA coated plates) in accordance with the present disclosure.

Mice were subcutaneously immunized and boosted with BSA-cocaine combined with adjuvants, lipopolysaccharide (LPS) and Alum, as depicted in FIG. 52. This vaccine was expected to result in the generation of two types of antibodies: anti-BSA and anti-cocaine. As a standard way to determine antibody titer and immunization efficacy, serum collected on the $7^{th}$ week was serially diluted and the concentrations of two types of antibodies (anti-BSA and anti-cocaine) were tested by the ELISA using BSA and BSA-cocaine as recognition elements, respectively (FIG. 53, 54). There are two types of antibodies generated after cocaine immunization: anti-BSA and anti-cocaine. Since BSA-cocaine simultaneously bind to both types of antibodies, the difference in the antibody concentrations determined using BSA-cocaine and BSA coated plates represents the concentration of anti-cocaine antibody. Since BSA-cocaine is expected to bind with both types of antibodies simultaneously, the difference in the antibody concentrations obtained using BSA-cocaine and BSA represents the concentration of anti-cocaine antibody. Mice with higher anti-BSA-cocaine titer than the anti-BSA titer are considered as "vaccine responders" (FIG. 55, FIG. 56A-B). These responder mice were subjected to microneedle administration to test the ability of this novel method to detect the presence of anti-cocaine antibody in ISF. Immunized mice 1, 2, 3, 5 and 6 had higher anti-BSA-cocaine titer than the anti-BSA titer, which were therefore categorized as vaccine responders. Immunized mouse 4 was termed non-responder since it exhibited similar titers of anti-BSA antibody and anti-BSA-cocaine antibody.

Figure 57:
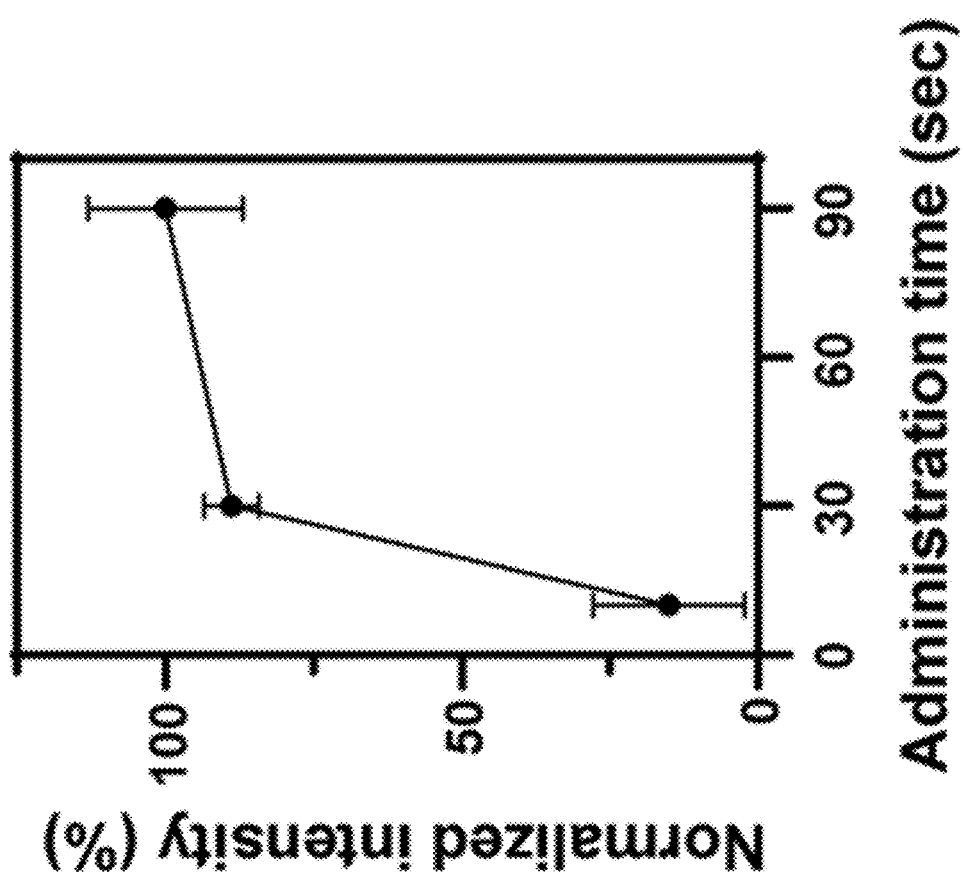
FIG. 57 is an exemplary embodiment of a plot showing normalized fluorescence intensity (with respect to highest intensity) on microneedle patches, which have been administered on ventral mouse skin and left for 15, 30 and 90 seconds in accordance with the present disclosure. Error bar represents standard deviation, N=3 repeated tests.
Figure 58:
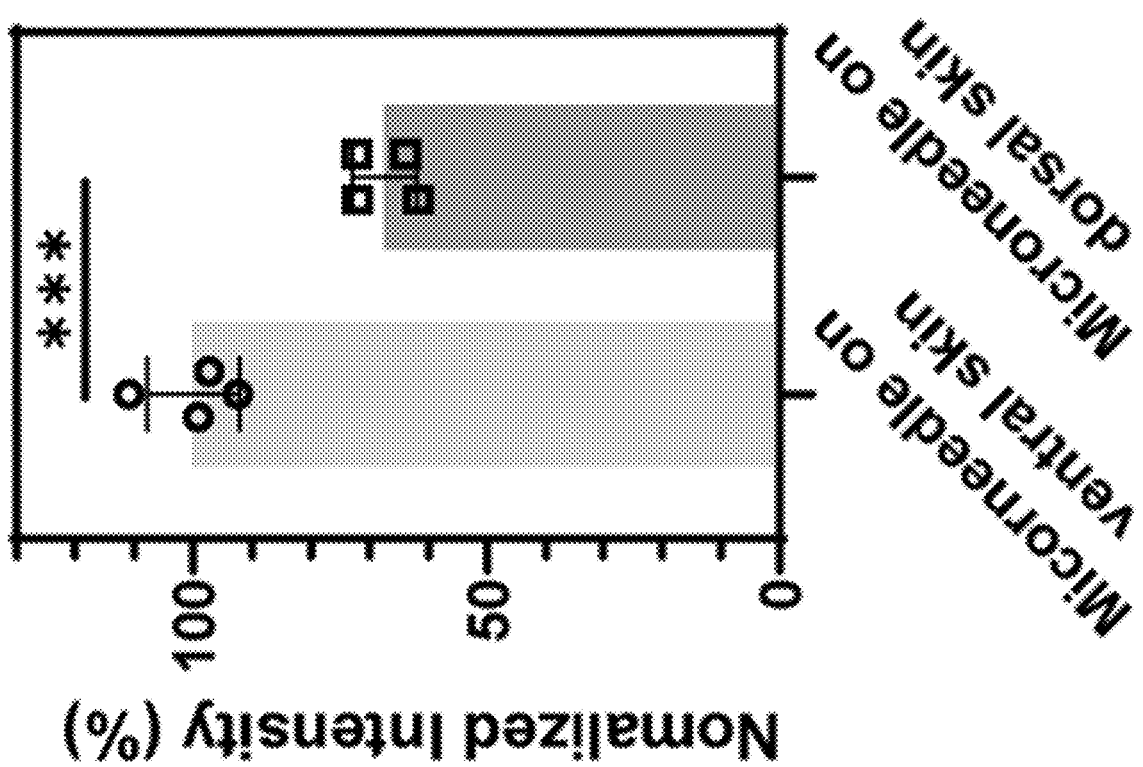
FIG. 58 is an exemplary embodiment of a plot depicting normalized fluorescence intensity on microneedle patches administered on ventral and dorsal skin of mouse in accordance with the present disclosure. Error bar represents standard deviation, N=4 repeated tests, data statistically significant P value=0.0004, *** P<0.001 by one-tailed unpaired t-test with Welch's correction.

To determine the shortest time scale for effective capture of antibodies, the BSA-coated microneedle patch was administered on the mouse dorsal skin for different durations. 30 seconds of microneedle patch administration was found to be sufficient to capture BSA-specific antibodies (FIG. 57). Longer administration of the microneedle patch did not significantly alter the fluorescence signals corresponding to the antibodies. To assess the site-to-site variations in the measured concentrations, four microneedle patches coated with BSA were administered on the ventral and on the dorsal skin of a responder mouse. The microneedle patches were subsequently probed by anti-mouse IgG and plasmonic-fluor ex vivo. Very small differences (relative standard deviation <8%) were noted in the fluorescence intensity among the four microneedle patches administered on the same side of the mouse. However, the four microneedle patches administered on the ventral side exhibited nearly 30-40% higher fluorescence intensity compared to those on the dorsal side (FIG. 58). This observation underscores the importance of accounting for site-to-site variation and consistent administration of the microneedle patches to ensure reliable comparison across different subjects and experiments.

Figure 59:
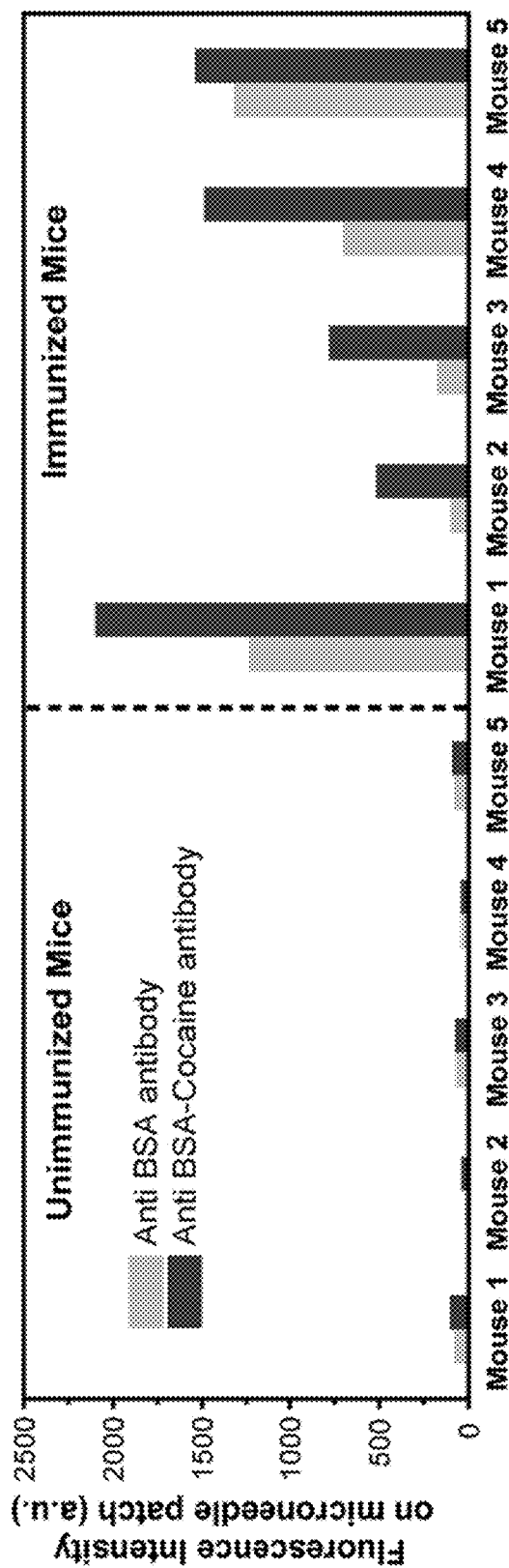
FIG. 59 is an exemplary embodiment of a plot showing fluorescence intensity obtained from microneedle patch with BSA or BSA-cocaine coating from both immunized and unimmunized group in accordance with the present disclosure.

To validate the applicability of the plasmonic-fluor enhanced microneedle patch in detecting cocaine-specific antibodies in a minimally-invasive manner, five unimmunized mice and five responder-mice were employed. Each mouse was administered with two microneedle patches coated with BSA and BSA-cocaine, and the patches were left on the skin for only 30 seconds. In the five responder-mice, high fluorescence signal was observed and there was significant difference in the fluorescence intensity between the BSA and BSA-cocaine microneedle patches. On the other hand, in the case of the microneedle patches from five unimmunized mice, a much lower fluorescence signal was noted and there was negligible difference between the BSA and BSA-cocaine microneedle patches (FIG. 59). Taken together, these results indicate that the plasmonic-fluor enhanced microneedle patch is a promising tool to determine and evaluate the vaccine response efficiency in a simple and non-invasive manner. In contrast to conventional blood-drawing, the microneedle method enables constant and easy monitoring of vaccine efficiency in individuals and accelerates vaccine development.

Figure 60:
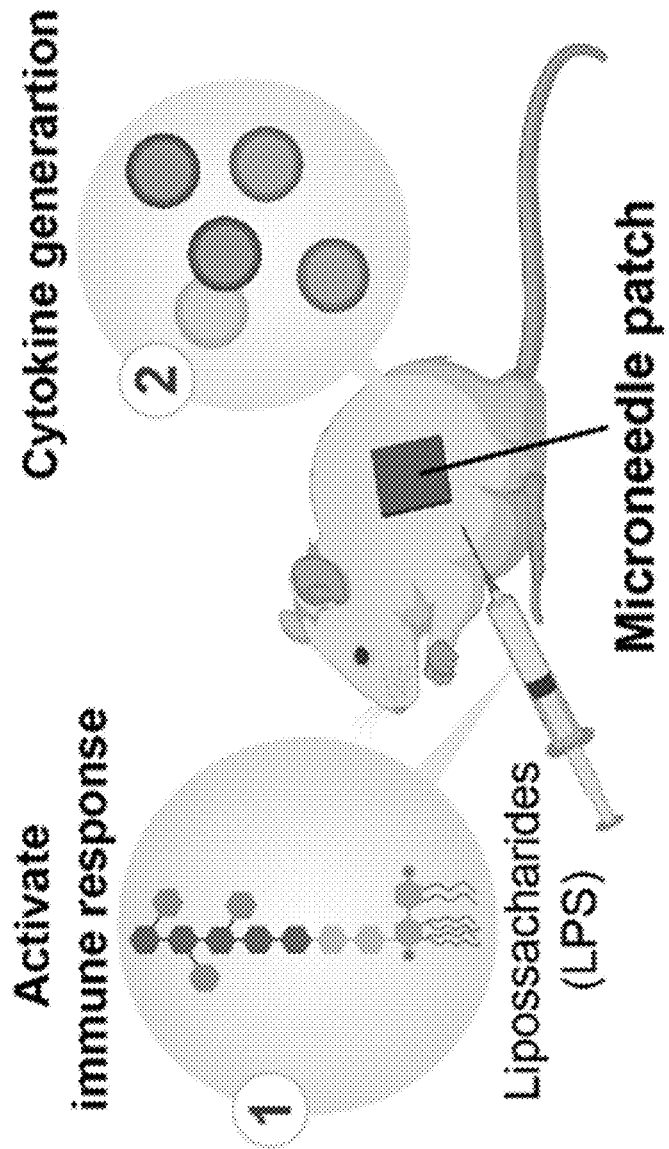
FIG. 60 is an exemplary embodiment of a schematic illustration showing the working principle of immune response induced by LPS administration, cytokine generation, and administration of the microneedle patch for longitudinal detection in accordance with the present disclosure.

Example 5: Detection and Quantification of Cytokines in an Endotoxin-Induced Shock Mouse Model Next, the detection of cytokines in dermal ISF of an LPS-induced endotoxin shock mouse model was demonstrated using the microneedle patch. LPS, a pathogen-associated molecular pattern (PAMP), triggers innate immunity and induces secretion of multiple pro-inflammatory cytokines (FIG. 60). Measurement and monitoring of these pro-inflammatory cytokines in blood has been an established method for evaluating the ability of immune system to mount an innate inflammatory immune response.

Figure 61:
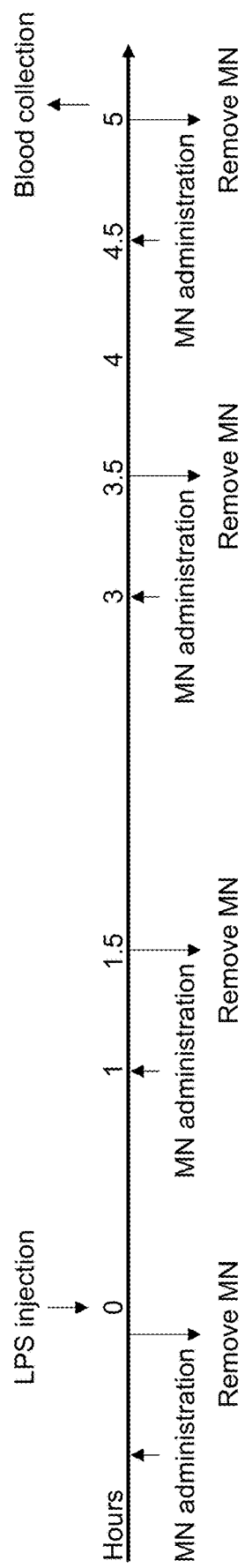
FIG. 61 is an exemplary embodiment of a timeline of endotoxic shock (LPS injection), longitudinal microneedle administration on mice, and blood collection (for validation of the microneedle test) in accordance with the present disclosure.
Figure 62:
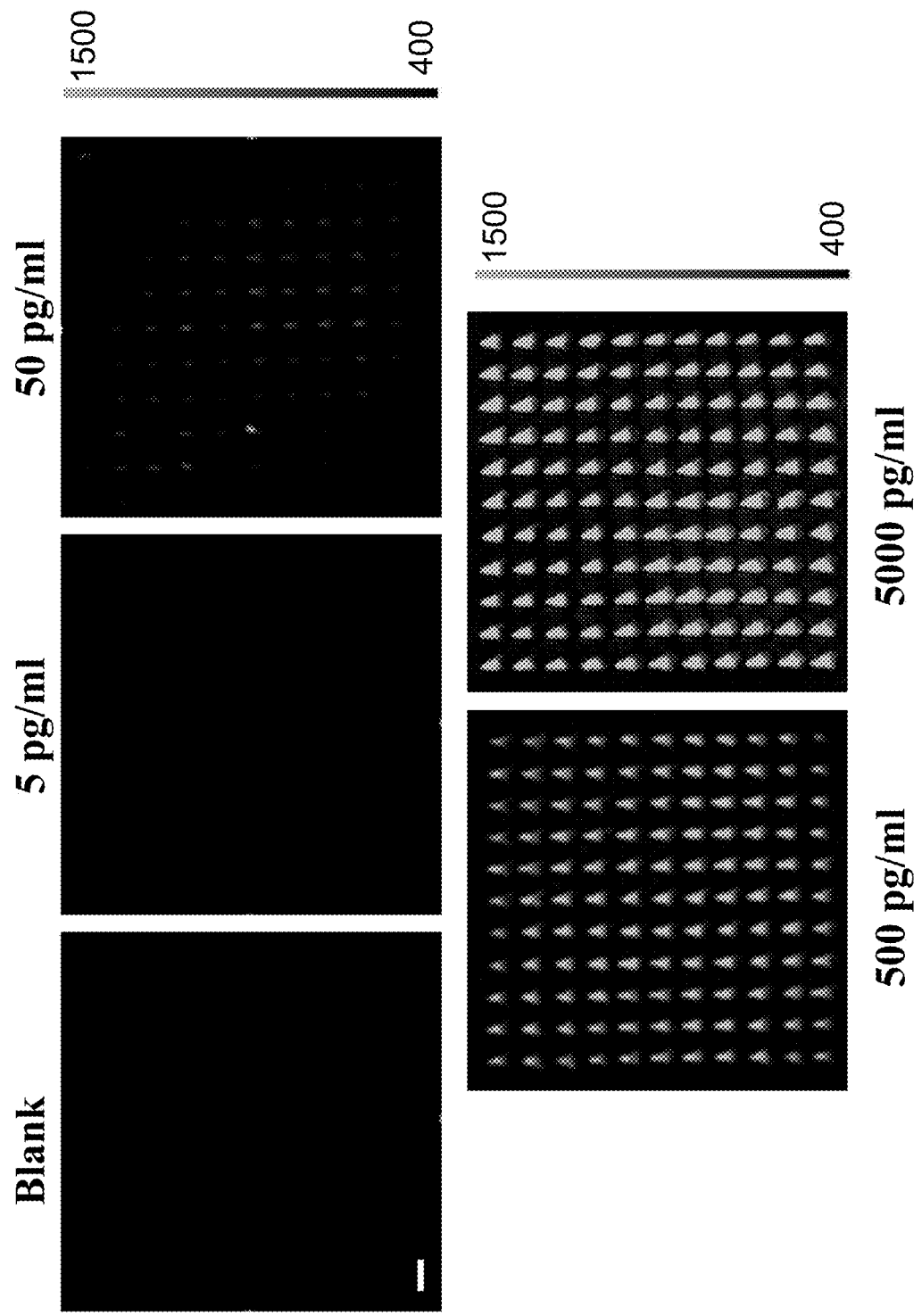
FIG. 62 is an exemplary embodiment of a representative fluorescence map of mouse IL-6 captured microneedles at varying concentrations in accordance with the present disclosure. Scale bar 500 μm.
Figure 63:
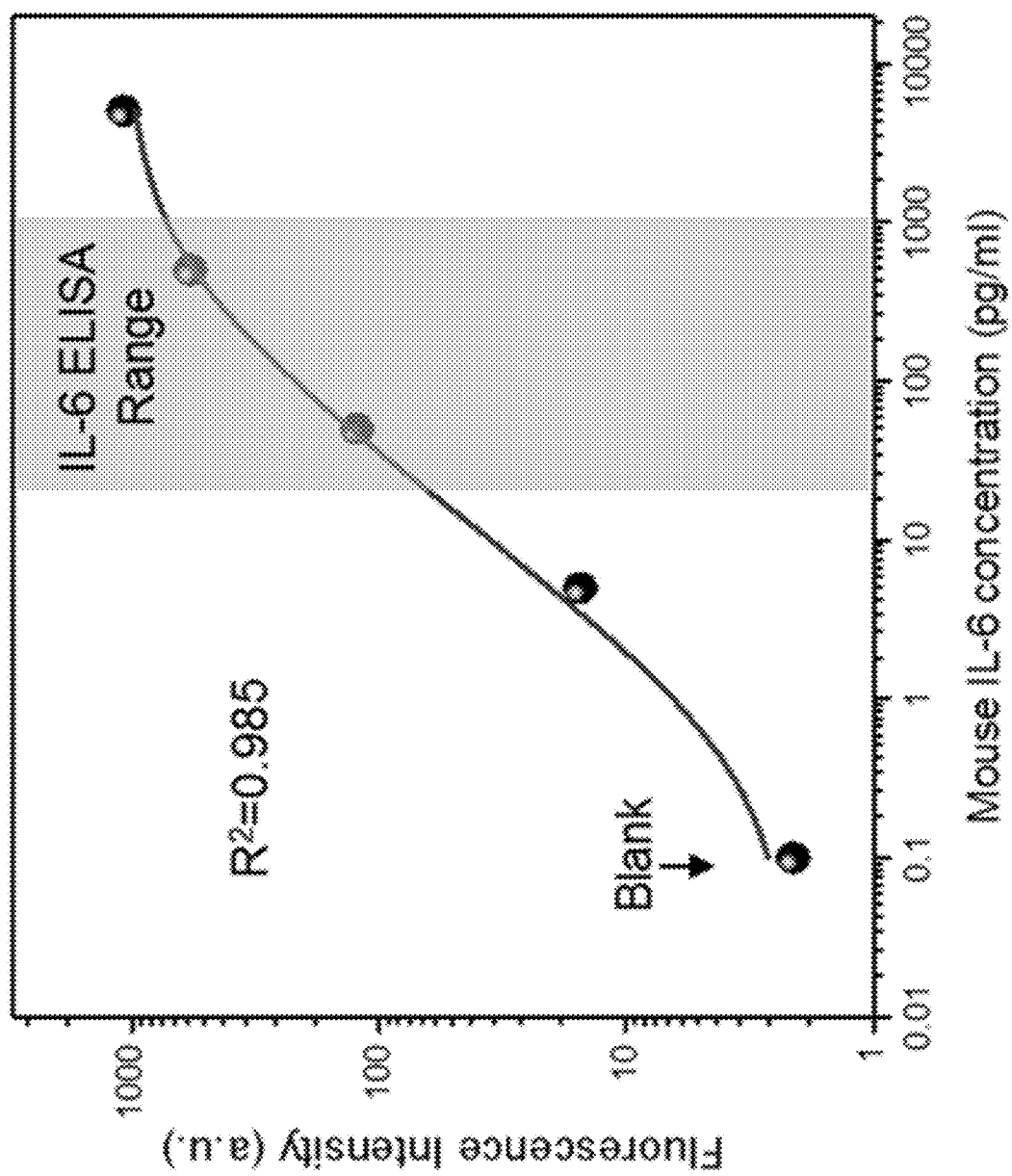
FIG. 63 is an exemplary embodiment of a standard curve of IL-6 on a microneedle in accordance with the present disclosure.
Figure 64:
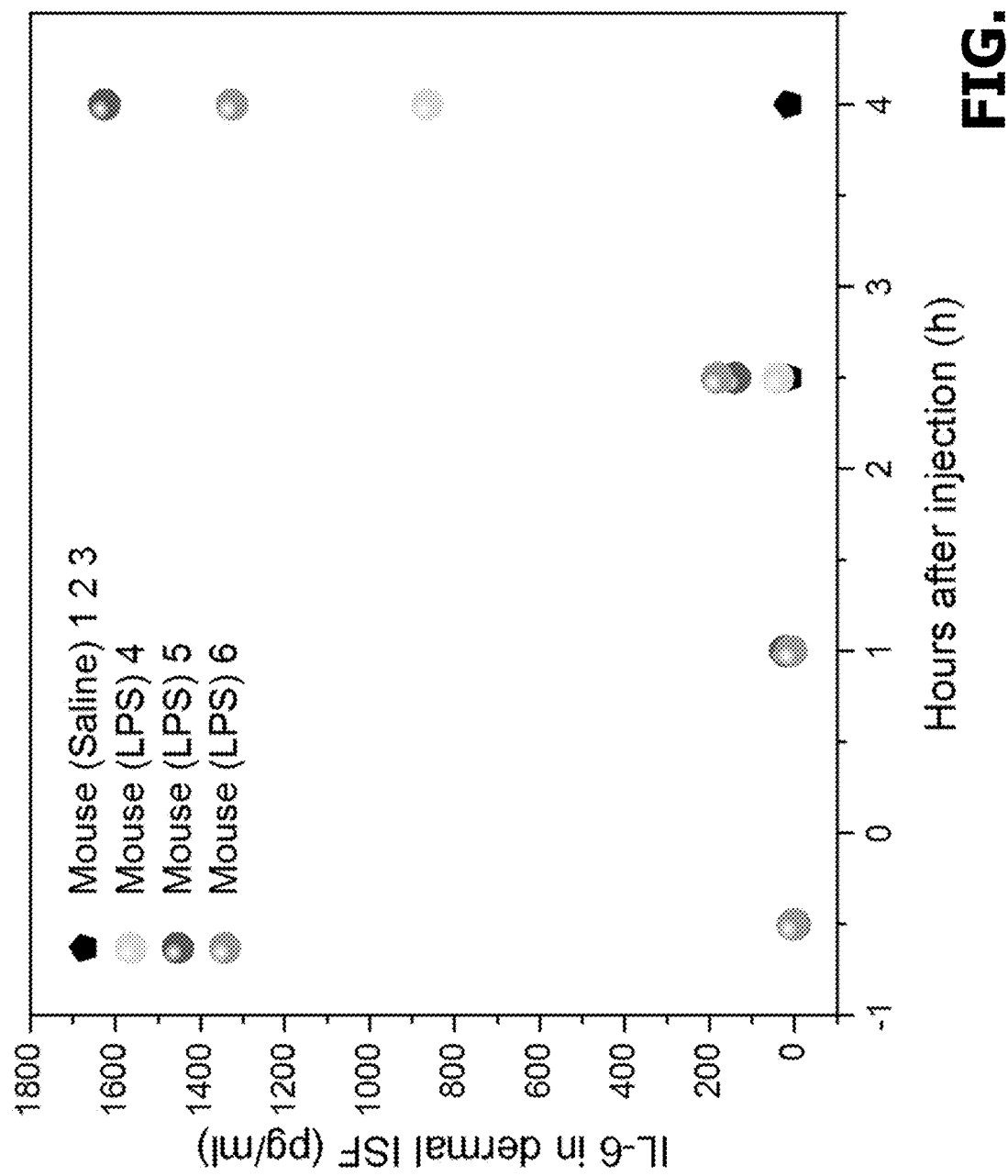
FIG. 64 is an exemplary embodiment of IL-6 in dermal ISF in accordance with the present disclosure.
Figure 65:
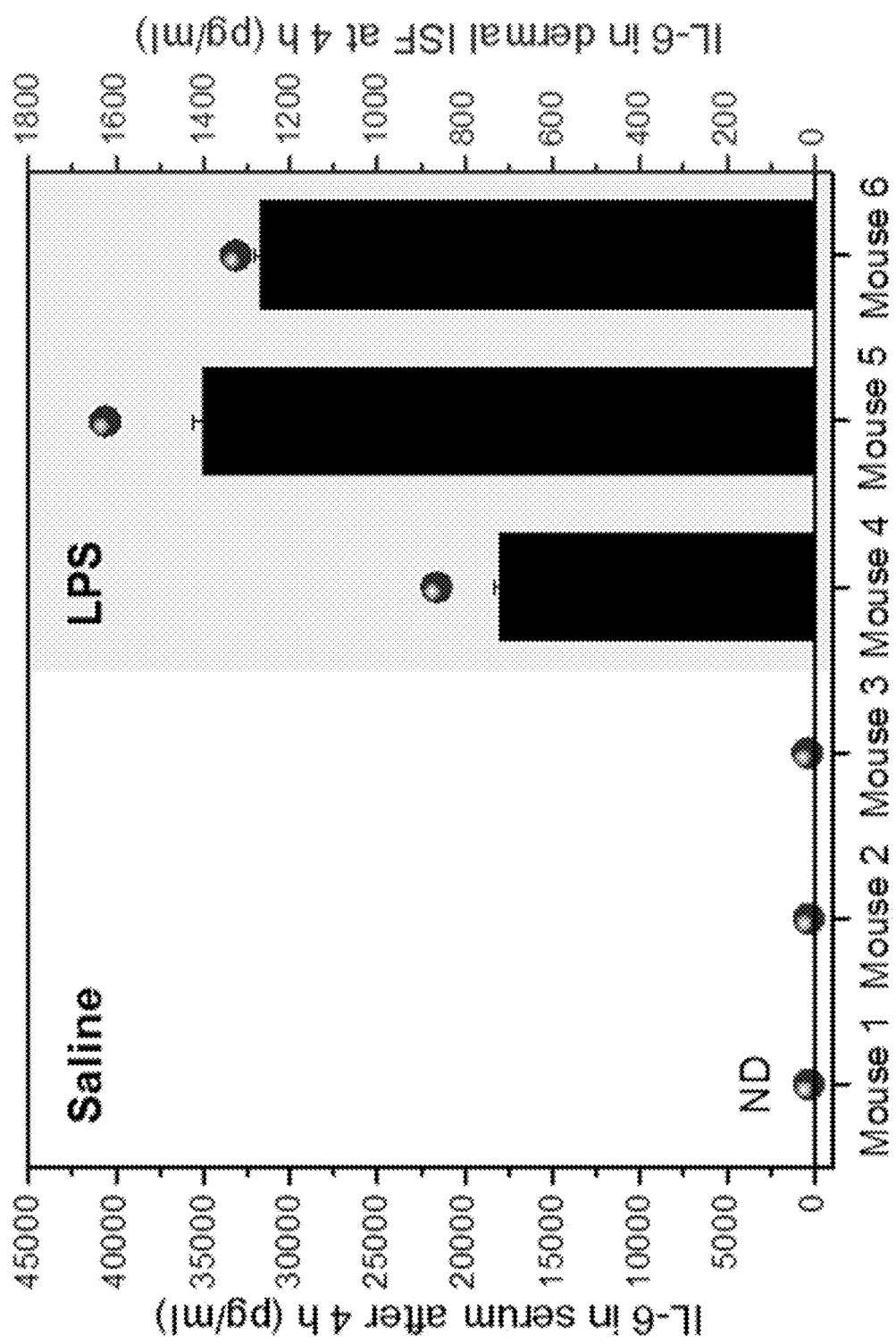
FIG. 65 is an exemplary embodiment of IL-6 in serum in accordance with the present disclosure.
Figure 66:
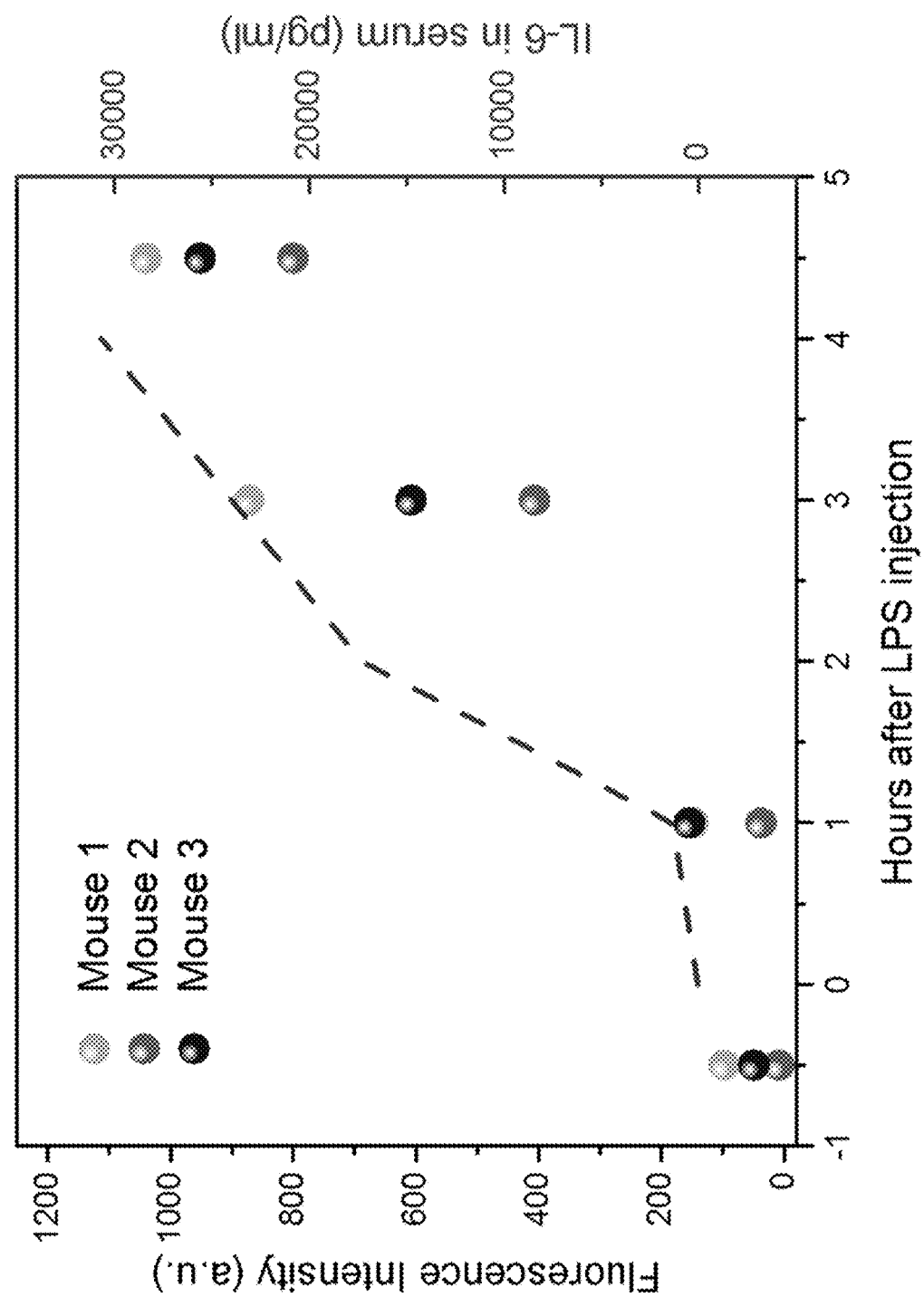
FIG. 66 is an exemplary embodiment of cytokine detection in dermal ISF through a microneedle patch over time in accordance with the present disclosure.
Figure 67:
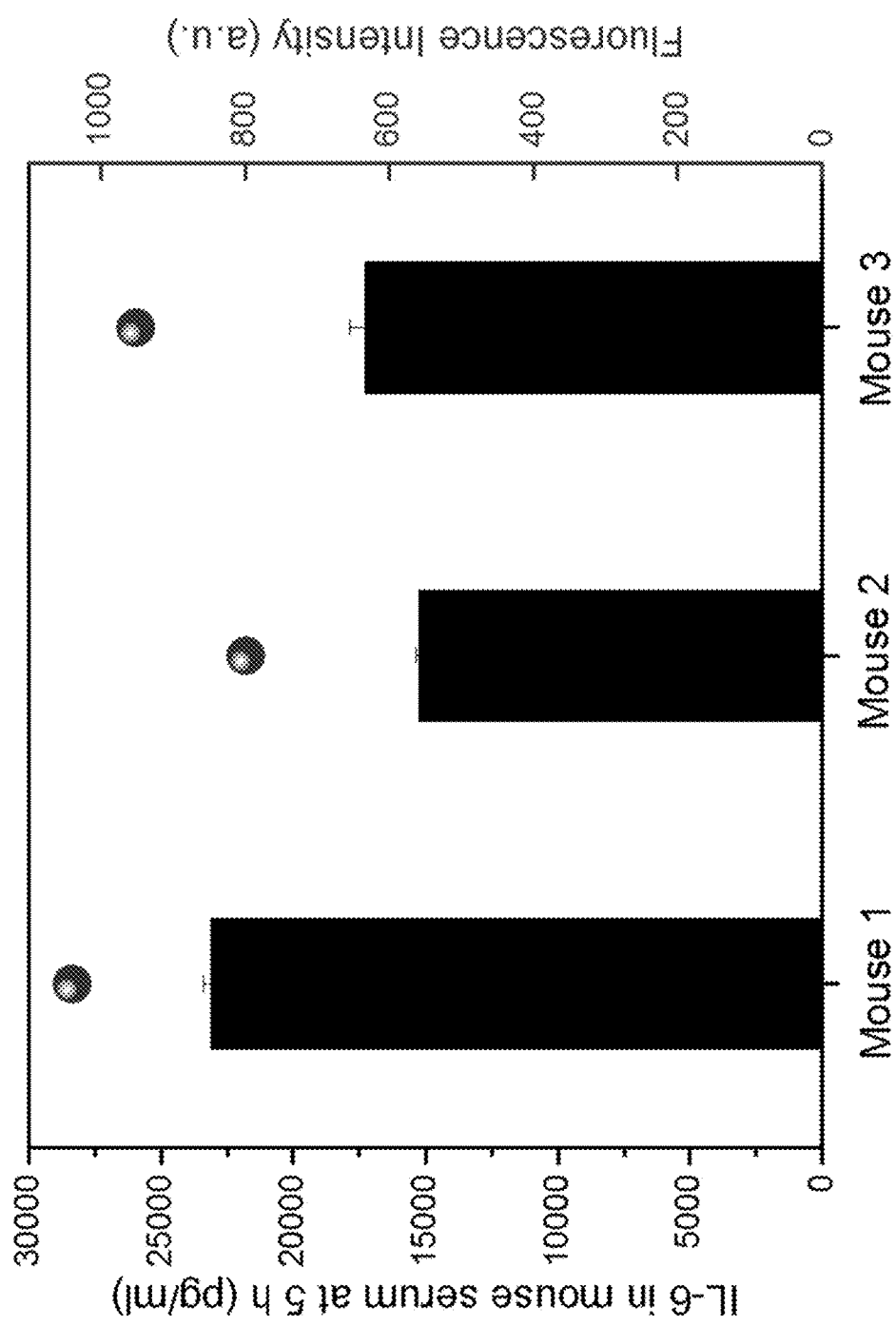
FIG. 67 is an exemplary embodiment of cytokine detection in dermal ISF through a microneedle patch at 5 h in accordance with the present disclosure.

BALB/C mice were injected intra-peritoneally with LPS (1 μg/g) to induce an acute phase response and systemic inflammation. Using functionalized microneedle patches, the longitudinal concentrations of mouse interleukin-6 (IL-6) in ISF was measured, which is known to increase in serum over 4 hours after LPS administration. Microneedle patches, pre-functionalized with IL-6 capture antibodies (as capture biorecognition elements), were administered at different time points on mouse ventral skin and left undisturbed for 20 minutes (FIG. 61). Fluorescence of IL-6 on microneedles was detectable at pg/ml concentrations (FIG. 62). A standard curve of IL-6 on microneedle which has a much broader dynamic range and lower detection limit. In control mice, there is only a tiny increase of the signal on microneedle, while the signal from LPS injected mice steadily increases. The fluorescence intensity from microneedle correlated well with serum (FIG. 63-65). Cytokine detection in dermal ISF through microneedle patch showed that, after immune adjuvant injection (LPS), cytokines including IL-6 gradually increased and reached 20-50 ng/ml level in serum within 4-5 hours (FIGS. 66 and 67). Repeated trials showed similar results and trends on microneedle and were comparable with results and trends in serum.

The microneedle patch was administered every 1-1.5 hours where blood collection normally is hard to perform in such high frequency within this short time. After the last administration, blood was collected to perform a gold standard ELISA to correlate with microneedle patch values.

Figure 68:
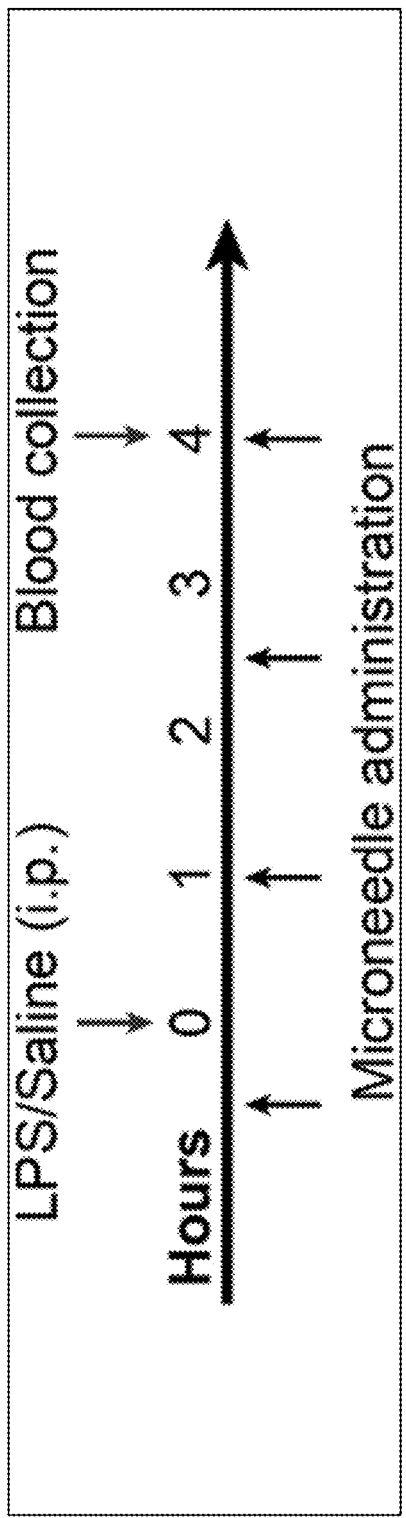
FIG. 68 is an exemplary embodiment of another timeline of endotoxic shock (LPS injection), longitudinal microneedle administration on mice, and blood collection (for validation of the microneedle test) in accordance with the present disclosure.
Figure 69:
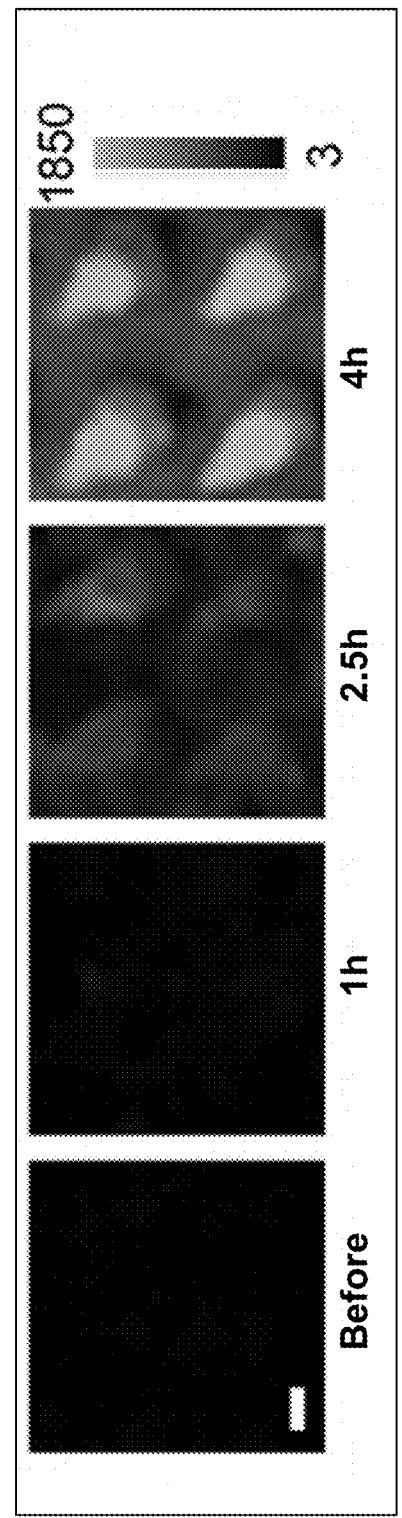
FIG. 69 is an exemplary embodiment of a representative fluorescence map representing mouse IL-6 captured on the microneedles before and at 1, 2.5 and 4 hours post LPS injection in accordance with the present disclosure. Scale bar 200 mm.
Figure 70:
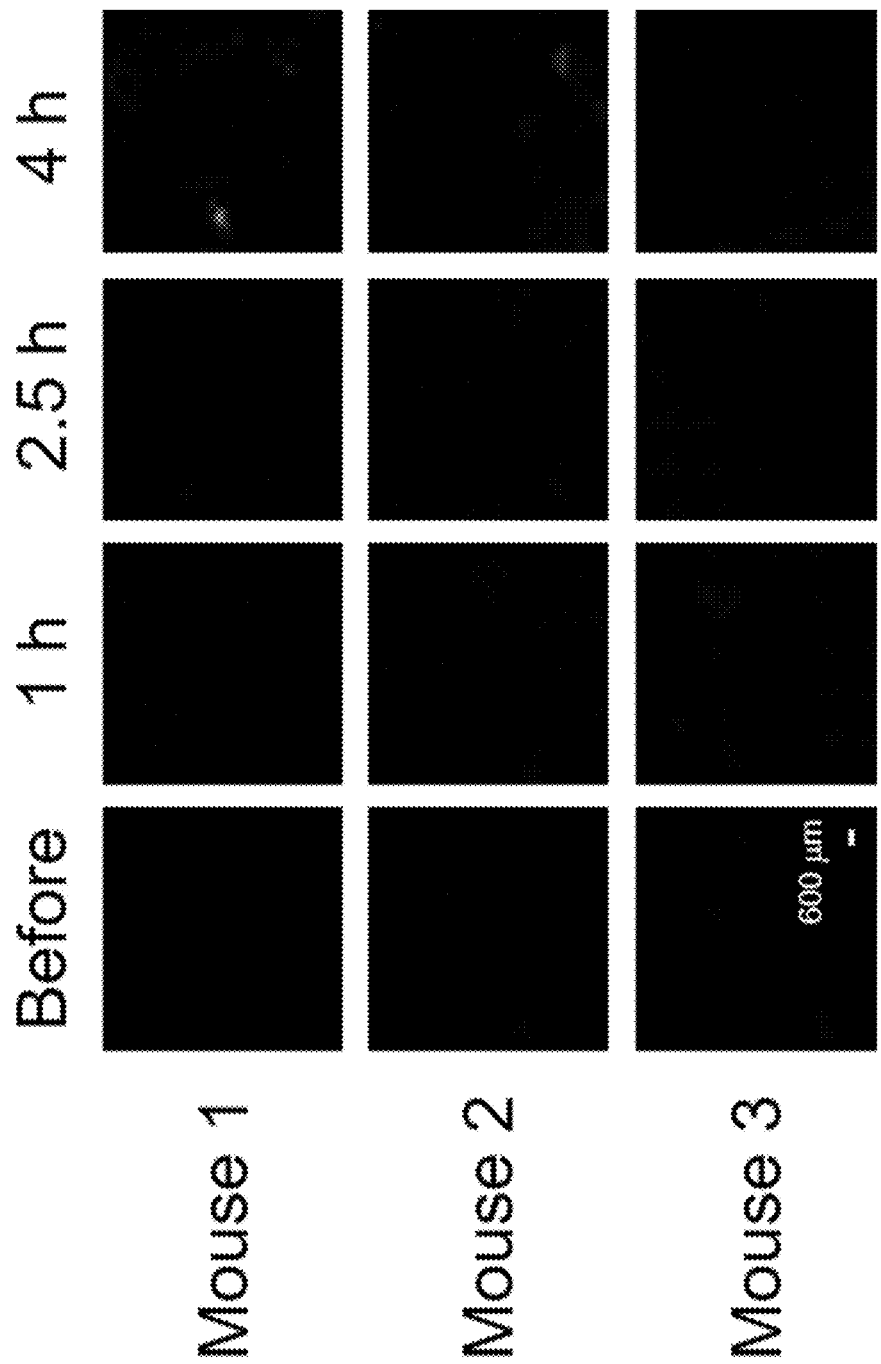
FIG. 70 is an exemplary embodiment of fluorescence intensity maps of microneedle patches before and at 1, 2.5 and 4 hours post PBS injection as control group in accordance with the present disclosure.
Figure 71:
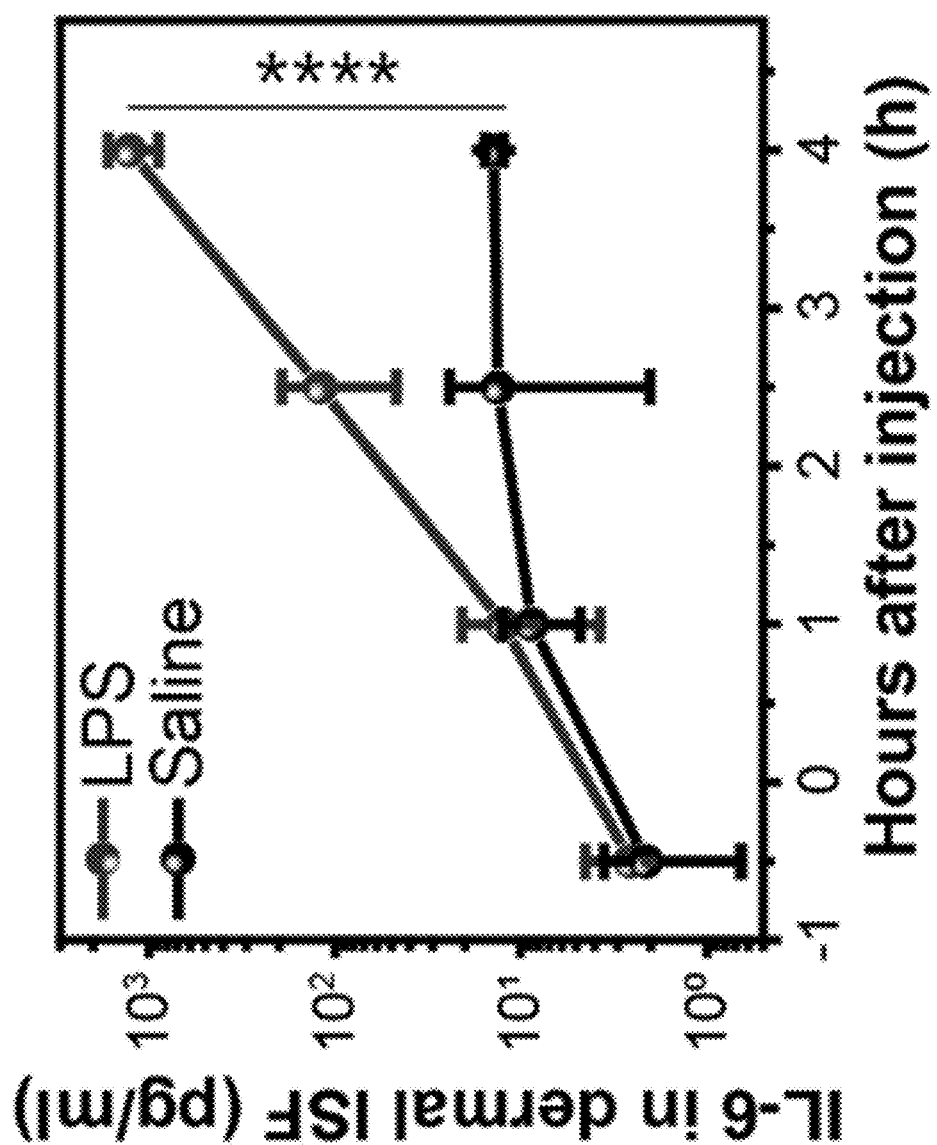
FIG. 71 is an exemplary embodiment of a plot depicting concentrations of mouse IL-6 in ISF before and at 1, 2.5 and 4 hours post LPS/saline injection measured using a microneedle in accordance with the present disclosure. Data statistically significant, **** P<0.0001 by two-way analysis of variance (ANOVA) with Sidak's multiple-comparison test.
Figure 72:
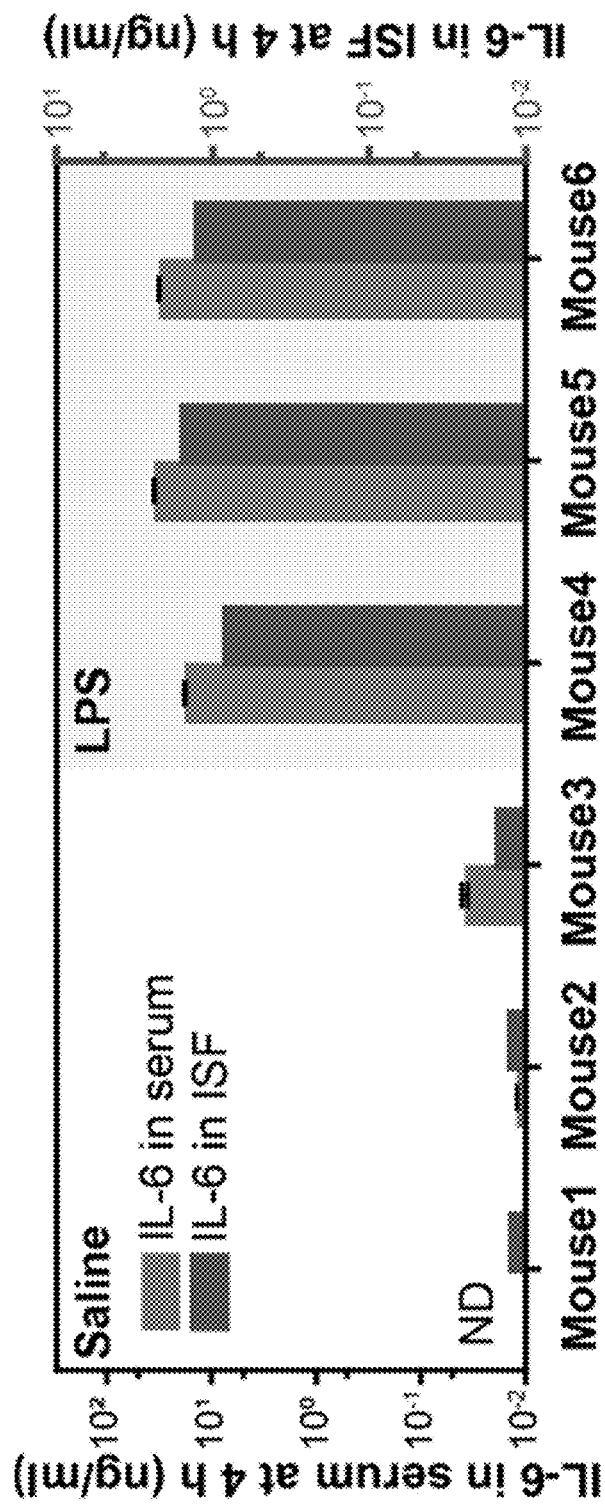
FIG. 72 is an exemplary embodiment of a plot showing the comparison of concentrations of IL-6 measured in serum and ISF in accordance with the present disclosure.

After removing the microneedle patches from the skin, p-FLISA was performed ex vivo to measure the concentration of IL-6. Fluorescence intensity corresponding to the plasmonic-fluors on the microneedle patches exhibited a gradual increase from 1 to 4 hours post LPS injection (FIGS. 68 and 69), while no significant change was observed in mice injected with saline (negative control group) (FIG. 69, 70). Note that the microneedle patches shown in FIG. 70 exhibited extremely weak fluorescence indicating the extremely low concentrations of IL-6 in dermal ISF for these control mice. Based on the standard curve (obtained using microneedle patches exposed to known concentrations of IL-6), the concentrations of IL-6 in mouse ISF were determined to be equivalent to 2.6±1.9, 12.3±8.6, 120.4±73.4 and 1271.9±393.4 pg/ml at 0, 1, 2.5 and 4 hours post LPS injection, respectively (FIG. 71). The IL-6 concentration in sera collected 4 hours after LPS/saline injection exhibited good qualitative correlation with that measured in ISF using the microneedle method at the same time point (FIG. 72). At 4 hours post LPS injection, IL-6 in dermal ISF determined by plasmonic-fluor enhanced microneedle (blue) exhibited good qualitative correlation with that in serum tested by conventional ELISA (grey). However, the serum IL-6 concentration was found to be nearly 22-fold higher compared to that in the ISF. The absolute concentration of the protein biomarkers in ISF is lower than the concentration in blood, which can partly be ascribed to the difference between microneedle-based analyte sampling method and solution-based standard curve, as well as inherent variation of proteins in body fluids. The p-FLISA standard curve, which is used for estimating the concentration of the analyte, is obtained by exposing the microneedle patches to known concentrations of IL-6 in standard dilution buffer. In contrast, microneedle based ISF sampling occurs in a "dense tissue matrix", resulting in slower diffusion kinetics and consequently a lower "apparent concentration" of the analyte. Nevertheless, the analyte concentration determined using the microneedle-based method exhibited excellent qualitative agreement with the measured concentrations in serum samples (FIG. 72).

Frequent and timely measurement of protein biomarkers is critical for disease monitoring and diagnostics in both biomedical research and clinical applications. Unfortunately, conventional longitudinal measurements require frequent blood draws in a short period, which may cause iatrogenic anemia and elevate morbidity of patients. Moreover, it is often impossible to repeatedly draw blood from small experimental animals, which will result in their death. The minimally-invasive microneedle method represents a transformative approach to perform frequent, sensitive, and accurate measurements of protein biomarkers in a longitudinal manner in the same mouse.

Figure 73:
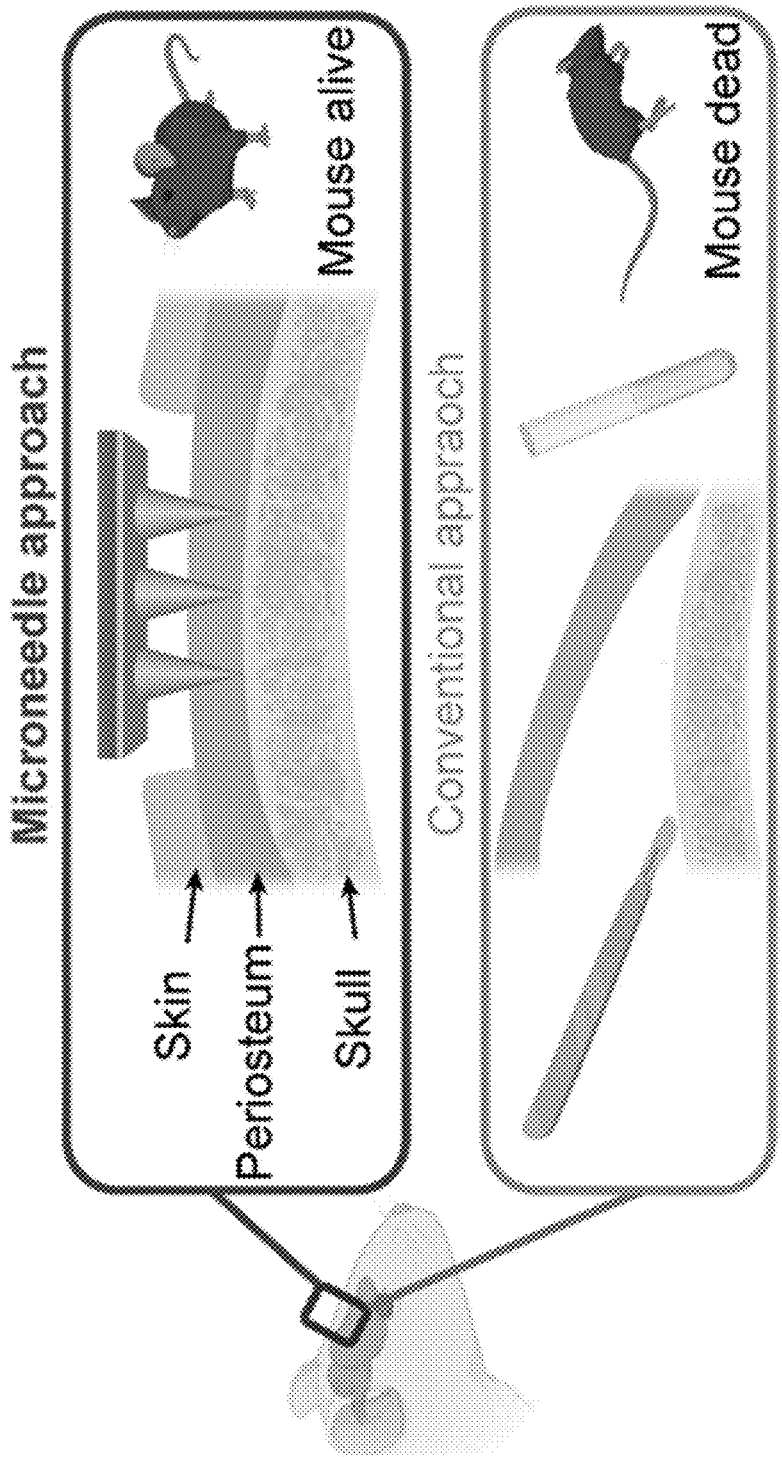
FIG. 73 is an exemplary embodiment of a schematic illustration showing the microneedle approach and conventional approach to measure the endogenous biomarkers in calvarial periosteum in accordance with the present disclosure.

Example 6: Detection and Quantification of Endogenous Matricellular Protein in Periosteum The quantification of endogenous biomarkers at specific sites or tissues of interest is highly desirable for biomedical and clinical research. Conventional biofluids, such as blood, are not able to reflect local concentrations of biomarkers. Furthermore, such local detection and monitoring of relevant biomolecules remains challenging due to the difficulty in collecting an adequate amount of biofluid in a minimally invasive manner. To overcome these challenges, the microneedle patch described herein was developed to efficiently sample and measure protein analytes at specific tissue or membrane locations with high sensitivity and specificity (FIG. 73). Microneedle detection is minimally-destructive, and mice can recover after testing; standard analysis requires scraping of the skull and isolation of periosteum, which usually necessitates euthanasia. Endogenous matricellular periostin was detected in calvarial periosteum and skin of the wild type (WT) mice but not the periostin knockout (Postn$^{KO}$) mice with microneedle patch.

Figure 74:
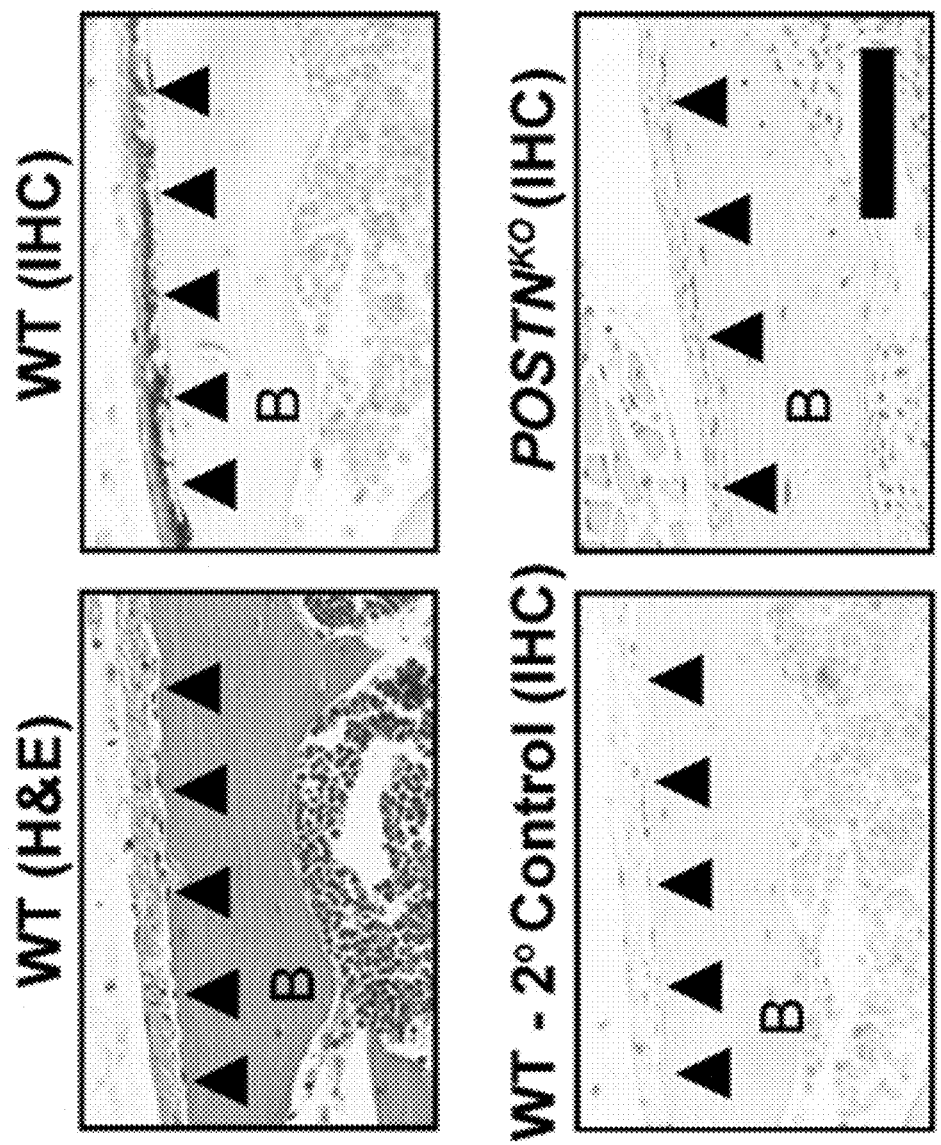
FIG. 74 is an exemplary embodiment of representative images of histology (H&E) and immunohistochemistry (IHC) showing a high local concentration of the periostin in accordance with the present disclosure.

The periosteum is a fibro-cellular membrane, which covers the outer surface of bones and plays key roles in bone growth, fracture healing and skeletal regeneration. In rodents and humans, the average thickness of the periosteum is 40 μm and 100 μm for both tibia and femur, respectively. In mouse calvaria discussed herein, the average periosteal thickness was 29±15 μm (FIG. 74). The extracellular matrix of the periosteum contains a high local concentration of the matricellular protein, periostin. It is encoded by Postn gene and plays important roles in bone regeneration and bone tumor metastasis. In addition, a circulating isoform of periostin has been identified as a potential biomarker of bone density loss and osteoporosis, tumor metastasis, and airway disease. As disclosed herein, the applicability of the microneedle patch was tested for the detection and quantification of periostin in a novel tissue, the calvarial periosteum, and in the dermal ISF.

Figure 75:
FIG. 75 is an exemplary embodiment of optical images showing the administration of the microneedle patch on mouse calvarial periosteum (head of mice was stabilized on a stereotaxic instrument) in accordance with the present disclosure.
Figure 76:
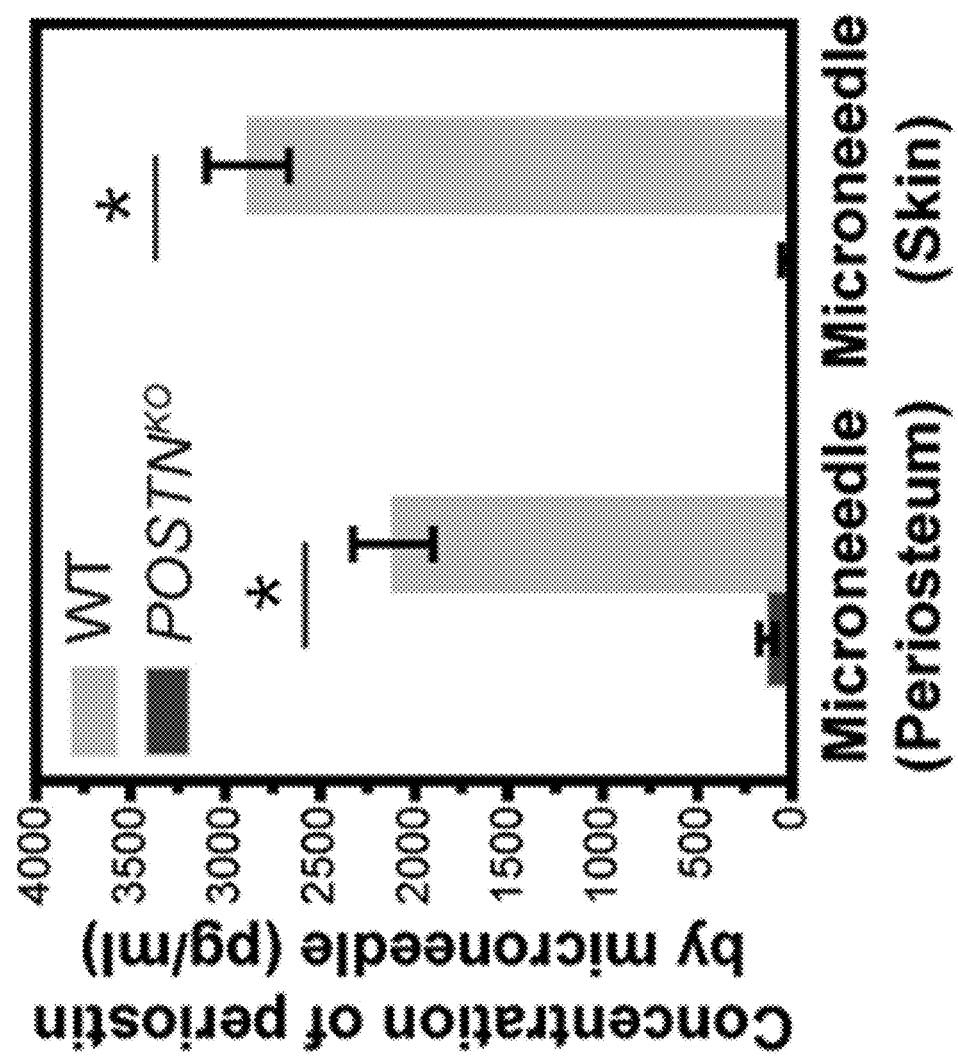
FIG. 76 is an exemplary embodiment of a plot depicting concentration of periostin on skin and periosteum of the WT and Postn$^{KO}$ mice determined by microneedle patches in accordance with the present disclosure. Error bars, s.d. Data statistically significant P value=0.0206 for microneedle on periosteum and P value=0.0153 for microneedle on skin, * P<0.1 by one-tailed unpaired t-test with Welch's correction.

Transgenic periostin knock-out mice (Postn$^{KO}$) and wild type mice (WT) were employed as experimental and control groups, respectively. WT mice demonstrated high expression of POSTN protein in the calvarial periosteum by immunohistochemistry (IHC), which was absent in Postn$^{KO}$ mice (FIG. 74). The calvaria of WT and Postn$^{KO}$ mice were immunostained with antibodies against periostin (brown). Periosteum (top, arrowheads) of WT mice exhibit strong expression of periostin, while staining was absent in WT sections lacking primary antibody (secondary antibody only control) and in sections of calvaria from Postn$^{KO}$ mice. Across the surface of skull, the average thickness of the calvarial periosteum was 29+/−15 um. "B" represents the position of bone. To detect periostin, microneedles were pre-functionalized with anti-periostin antibodies and administered to the calvarial periosteum layer for 10 minutes (FIG. 75). Simultaneously, another pre-functionalized patch was administered on the dorsal skin of the same mouse for 10 minutes. Subsequently, p-FLISA assay was performed ex vivo to measure the local concentrations of periostin. Both periosteum and skin of WT mice (n=2) demonstrate high concentration of periostin, while Postn$^{KO}$ mice (n=2) show negligible amount. Fluorescence intensity corresponding to the plasmonic-fluors on the microneedle patches (both on periosteum and dorsal skin) exhibited a strong signal from WT mice, while no significant signal was observed in Postn$^{KO}$ mice (FIG. 76). Based on the standard curve, concentrations of periostin in periosteum and skin were around 2000 pg/ml from WT, as compared to negligible amount in transgenic Postn$^{KO}$ mice.

Figure 77:
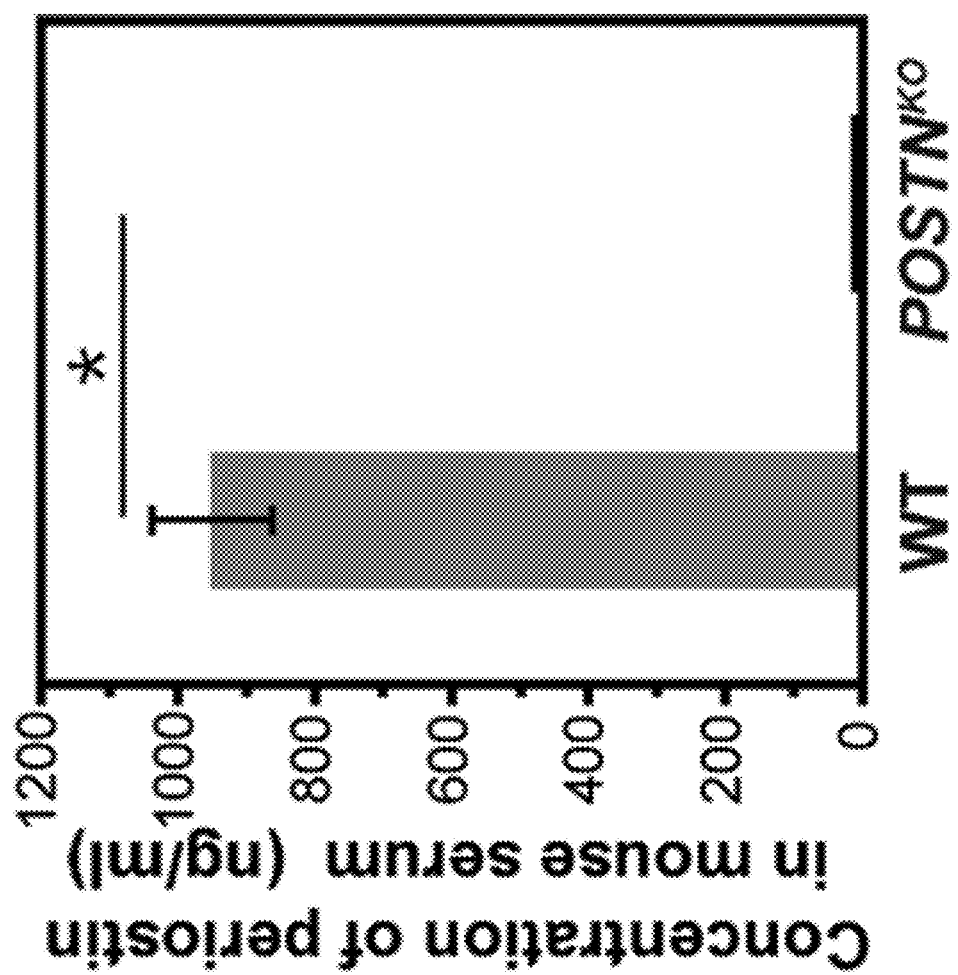
FIG. 77 is an exemplary embodiment of a plot showing concentration of periostin in serum of the WT and Postn$^{KO}$ mice in accordance with the present disclosure. Error bars, s.d. Data statistically significant P value=0.0205, * P<0.1 by one-tailed unpaired t-test with Welch's correction.

Compared to conventional methods, the plasmonic-fluor enhanced microneedle method did not require extraction or isolation of periosteum during analysis, indicating that multi-round testing and long-term monitoring is achievable (FIG. 73). Serum of WT mice revealed high concentration of periostin, while Postn$^{KO}$ mice had a negligible amount. It is of note that the concentration of periostin in periosteum and skin measured by microneedle is nearly 450-fold and 330-fold lower than the concentration in mouse serum, which was around 950 ng/ml (FIG. 77). This phenomenon is possibly due to binding and retention of periostin within the extracellular matrix, reducing the amount of available periostin which can be captured by the microneedle. In general, these results indicate that microneedle patch was used to evaluate the amount of an endogenous matricellular protein biomarker at specific tissue location in a minimally-invasive manner.

Conclusions

In some embodiments, a minimally-invasive, ultrasensitive and quantitative biodetection technology is disclosed based on a bilayered microneedle patch with plasmonic-enhanced fluoroimmunoassay. Through a series of mouse models, this novel technology was demonstrated to enable both simple and timely detection of biomarkers of interest including longitudinal monitoring of inflammatory immune responses, evaluation of vaccine efficiency in a minimally-invasive manner, as well as quantification of localized changes protein content within the tissue microenvironment. While largely retaining or enhancing the sensitivity and convenient workflow of conventional immunoassays, the plasmonic-enhanced microneedle method overcomes the need for tedious sample collection (e.g., blood draw, ISF extraction), making it highly attractive for clinical diagnostics. In addition to the biomedical research applications discussed herein, this microneedle technology is employed in point-of-care and resource limited settings, such as the patient's home, underserved urban and rural clinics, to facilitate rapid disease diagnosis and efficient therapeutic intervention in a more patient-friendly manner.

Exemplary Materials and Methods

The following materials and methods are exemplary in nature, and the present disclosure is not limited to the specific materials and methods described in this section.

Animals. All procedures have been approved by the Institutional Animal Care and Use Committee (IACUC) at Washington University in St. Louis. Mice were housed in the housing facility at a constant temperature (21-23° C.) and humidity (45-50%) on a 12 hours light-dark cycle (lights on 0700-1900 hr), with food and water available ad libitum throughout the studies.

Synthesis of magnetic nanoparticles. Magnetic nanoparticles ($Fe_3O_4$ NPs) were synthesized via previously reported polyol synthesis method. Briefly, 0.15 g of iron (III) chloride hexahydrate (Sigma Aldrich, 236489) was dissolved in a mixture of 3 mL ethylene glycol (Sigma Aldrich, 102466) and 1 mL ethanolamine (Sigma Aldrich, 398136) to form a stable light brown solution. After 30 minutes, 167.5 mg of polyethylene glycol (Sigma Aldrich, P3640) and 663.6 mg of sodium acetate trihydrate (Sigma Aldrich, 58625) was added under vigorous stirring. Subsequently, the solution was transferred to a Teflon-lined stainless-steel autoclave and heated to 200° C. for 8 hours. The $Fe_3O_4$ NPs were collected and washed three times, with ethanol and water, and re-dispersed in ethanol for further use.

Fabrication of microneedle. Microneedles were prepared using silicone molds with conical holes (Blueacre Technology Ltd.). In some embodiments, each microneedle is 600 µm in length with a diameter of 300 µm at the base. In some embodiments, the center-to-center spacing between the microneedles is 600 µm. Polystyrene/dichloromethane solution (25% w/v) was deposited on the silicone mold and left under vacuum at the bottom to create a negative pressure, followed by drying at room temperature for at least 4 hours, allowing the evaporation of the solvent and the formation of the polystyrene microneedle. $Fe_3O_4$ nanoparticles dispersed in polystyrene/dichloromethane solution (final concentration: 15% w/v of polystyrene and 8 mg/ml $Fe_3O_4$ nanoparticle in dichloromethane) were deposited on the back of the polystyrene microneedle patch, followed by vacuum condition. After drying in room temperature for 4 hours, microneedle patch was carefully separated from the mold and tailored into small pieces with square shape for further use. The preparation and storage of microneedle patches were performed in sterilized condition.

Fluorescence Enhancement Using Plasmonic-Fluor

Synthesis of AuNR. In some embodiments, the wavelength of gold nanorods was tuned to couple with dye molecules in order to achieve best enhancement factor. To prepare plasmonic-fluor-800CW, AuNR-760 (LSPR wavelength ~760 nm) was prepared by seed-mediated method. To prepare seed solution, 0.6 ml of 10 mM ice-cold $NaBH_4$ solution (Sigma Aldrich, 71321) was added into a solution containing 9.75 ml 0.1 M CTAB (Sigma Aldrich, H5882) and 0.25 ml 10 mM $HAuCl_4$ (Sigma Aldrich, 520918) under vigorous stirring at room temperature for 10 min. The solution changed from yellow to brown which indicates the formation of Au seed. To synthesize gold nanorods, the growth solution was prepared by the sequential addition of 2 ml 0.01 M $HAuCl_4$ aqueous solution, 38 ml 0.1 M CTAB, 0.55 ml 0.01 M $AgNO_3$ (Sigma Aldrich, 20439 0), 0.8 ml 1 M HCl (Sigma Aldrich, H9892) and 0.22 ml 0.1 M ascorbic acid (Sigma Aldrich, A92902) followed by gentle homogenization. Subsequently, 5 µl of the seed solution was added into the growth solution and left undisturbed in dark for 24 hours. AuNR solution was collected by centrifugation at 6000 rpm for 40 minutes to remove the supernatant. AuNR was then re-dispersed into nanopure water for further use.

Conjugation procedures. Bovine serum albumin (BSA) was first conjugated with biotin and 800CW sequentially through EDC/NHS chemistry. Specifically, 2 mg NHS-PEG4-biotin (Thermo Scientific, prod number 21329) was added to 2.2 ml 5 mg/ml BSA (Sigma-Aldrich, A7030) in 1×PBS and incubated at room temperature for 1 hour. BSA-biotin conjugation was purified by a desalting column (Thermo Scientific, Prod number 21329, 7000 MWCO). Next, 800CW was conjugated to BSA-biotin. 0.1 ml 1 M potassium phosphate buffer ($K_2HPO_4$, pH=9) was added into 1 ml purified BSA-biotin solution to raise the pH. Next, 25 µl 4 mg/ml NHS-800CW (Licor, P/N 929-70020) was added to the mixture and the solution was incubated at room temperature for 2.5 hours. BSA-biotin-800CW was purified by Zeba desalting column pre-equilibrated with nanopure water.

Synthesis of plasmonic-fluor. To prepare plasmonic-fluor-800CW, AuNR (wavelength around 760) was employed as the nanoantenna. 1 µl MPTMS (Sigma Aldrich, 175617) was added to 1 ml AuNR (extinction ~2) and the mixture was shaken on rocking bed for 1 hour. Subsequently, MPTMS-modified AuNR was collected by centrifugation at 6000 rpm for 10 mins and was further mixed with 2 µl APTMS (Sigma Aldrich, 281778) and 2 µl TMPS (Sigma Aldrich, 662275) to form the polymer spacer layer. Finally, AuNR/polymer solution was collected by twice centrifugation at 6000 rpm for 10 minutes to remove the free monomer and concentrated into a final volume of 10 µl. Next, BSA-biotin-800CW conjugate was coated around AuNR/polymer modified from a previously reported method. Specifically, pH of 100 µl 4 mg/ml BSA-biotin-800CW was first lowered by adding 1 µl 20 mg/ml citric acid (Alfa Aesar, 36664). Subsequently, concentrated AuNR/polymer solution was added into BSA-biotin-800CW solution and sonicated for 20 minutes under dark condition. The coated nanostructures were then collected by centrifugation at 5000 rpm for 5 minutes and subsequently incubated with 0.5 ml 0.4 mg/ml BSA-biotin-800CW (pH=10) for 3 days in 4° C. Finally, the nanostructures were washed four times using alkaline nanopure water (pH=10) by centrifugation at 6000 rpm and re-dispersed in 1% BSA 1×PBS solution for further use.

Figure 23:
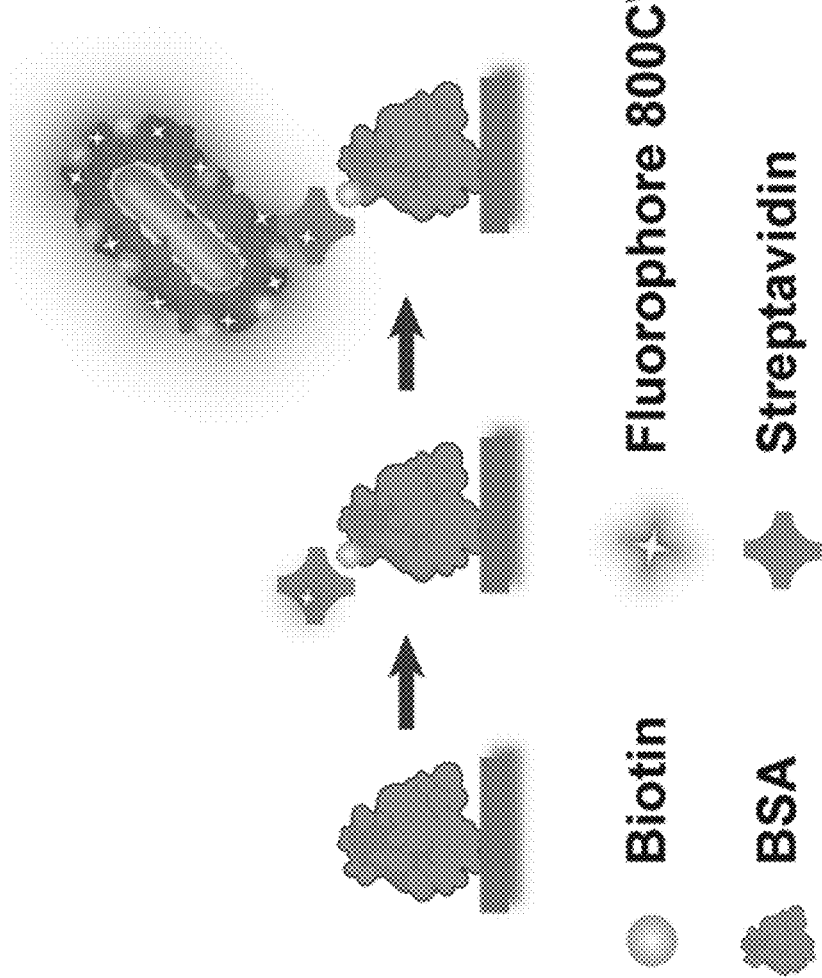
FIG. 23 is an exemplary embodiment of a schematic illustration of a model system designed to understand the enhancement of fluorescence signal using plasmonic-fluors compared to conventional fluorophores in accordance with the present disclosure.

Fluorescence enhancement using plasmonic-fluor. An exemplary test procedure is schematically illustrated in FIG. 23. Specifically, BSA-biotin was first immobilized on 96-well plate by incubating the well with 50 ng/ml BSA-biotin in 1×PBS at room temperature for 15 minutes. The plate was washed three times by using PBST (0.05% Tween 20 in 1×PBS) and then blocked using Odyssey® Blocking Buffer (PBS) (Licor, P/N 927-40100). 1 µg/ml streptavidin-800CW was subsequently added and incubated for 10 minutes. Next, the plate was washed three times using PBST and then incubated with ~76 pM plasmonic-fluor-800CW (in 1% BSA). Finally, after washing, 200 µl of PBST was added into each well and the fluorescence signal before and after the addition of plasmonic-fluor was recorded using Licor CLX fluorescence imager with the following scanning parameters: laser power~L2; resolution~169 µm; channel: 800; height: 4 mm.

Material characterization. Transmission electron microscopy (TEM) images were obtained using a JEOL JEM-2100F field emission (FE) instrument. A drop of aqueous solution was dried on a carbon-coated grid, which had been made hydrophilic by glow discharge. SEM images were obtained using a FEI Nova 2300 field-emission scanning electron microscope at an acceleration voltage of 10 kV. The extinction spectra of plasmonic nanostructures were obtained using a Shimadzu UV-1800 spectrophotometer. Fluorescence mappings were recorded using LI-COR Odyssey CLx imaging system. The X-ray diffraction (XRD) patterns of the $Fe_3O_4$ nanoparticles were obtained using a Bruker D8-Advance X-ray powder diffractometer using Cu Kα radiation ($\lambda$=1.5406 Å) over the 2θ range 10°-90°.

Mechanical test. The mechanical properties of the microneedle patch were measured by displacement-force test station (Instron 5583 electro-mechanical Universal Testing Machine) (FIG. 40). A microneedle patch was attached to a rigid platform with microneedles facing up. The sensor probe was brought in contact with the microneedles in the vertical direction at a speed of 0.1 mm $5^{-1}$. The initial distance between the sensor and microneedle tips was set to be 1 cm. Displacement-force measurements were acquired from the point at which the sensor first touched the microneedle tips to the onset of buckling of the microneedles.

Skin penetration efficiency test. Mouse skin after administration of microneedle patch was imaged by digital camera to assess skin penetration efficiency. After administration of microneedle patch for 15 minutes, mouse ventral skin was stained with trypan blue for 20 minutes. Mouse was subsequently euthanized, and the skin sample was imaged by digital camera after wiping remaining dye from the skin. In a separate experiment, after 15 minutes of administration of microneedle patch, mouse was euthanized, and its ventral skin was isolated carefully. These excised skins were washed with deionized water and then fixed with 4% formalin solution to stain with hematoxylin and eosin (H&E). Histological examination was conducted by an optical microscope under bright field illumination (Biotek Lionheart FX).

Protein retention test. To access stability of protein bound on the microneedles, the microneedles were coated with BSA-CW800. After washing with PBST and drying, fluorescence images were recorded using LI-COR Odyssey CLx imaging system. Subsequently, microneedles were administered on mouse dorsal skin and left for different periods of time, varying from 15 seconds to 60 minutes. Fluorescence images were recorded again using the same parameters in LI-COR Odyssey CLx imaging system. The fluorescence intensity before and after administration was compared to assess the retained fraction of the protein on the microneedle surface.

Assessing in vitro biocompatibility of microneedle patch. To evaluate toxicity of microneedle in vitro, human dermal fibroblast cells (HDF) were selected as a model system. Pristine microneedle and BSA coated microneedle were incubated in cell culture medium for 1 hour and 16 hours, representing short-term and potentially long-term contact with skin tissues. After removing microneedle patch, cell culture medium was employed to incubate with HDF for 24 hours. The cell viability was quantified using the 3-(4,5-dimethylthiazol-2-yl)-5-(3-carboxymethoxyphenyl)-2-(4-sulfophenyl)-2H-tetrazolium (MTS) assay.

Assessing systemic toxicity of microneedle patch. For toxicity assessment in vivo, mice administered with BSA-coated microneedle patch were selected as the treatment group, while mice without administration were used as control group. The representative organs including heart, lung, liver, kidney and spleen in each group were harvested and fixed in 4% neutral buffered formalin for histological analysis, which were subsequently processed by The Musculoskeletal Histology and Morphometry Core at Washington University in St. Louis for paraffin embedding, sectioning, and hematoxylin and eosin staining (H&E staining). Histological examination was conducted by an optical microscope under bright field illumination (Biotek Lionheart FX).

Bacterial endotoxin level of microneedle patch. To evaluate bacterial endotoxin level on microneedle surface, especially after blocking with BSA, microneedle patch coated with BSA were first incubated with endotoxin-free water overnight. Subsequently, the bacterial endotoxin level inside was detected and measured by Kinetic Chromogenic Limulus Amebocyte Lysate (LAL) assay (Thermo Scientific, Catalog number #88282).

Mouse IL-6 ELISA on microneedle and on microtiter plate. Mouse IL-6 DuoSet ELISA kit (R&D systems, catalog number DY406, lot number P1195781) was employed in the study. As-prepared magnetic microneedle patches were first placed in a 24 well plate (Corning, PART #3526) which was clamped on a magnetic plate separator (Luminex Corporation, PART #CN-0269-01) designed to accommodate the microplate. Microneedle patches were immersed and incubated with 1 ml of capture antibodies (2 µg/ml in PBS, R&D systems, PART #840171) through overnight incubation at room temperature, followed by washing and blocking with 2 ml reagent diluent (1×PBS containing 3% BSA, 0.2 µm filtered). During incubation and washing steps, microneedle patches were tightly attached to the bottom of well. After three times washing with PBST, 1 ml of serial diluted standard samples (R&D systems, PART #840173) were added into different wells and microneedle patches were incubated at room temperature for 2 hours. Subsequently, patches were washed and incubated with biotinylated detection antibodies (R&D systems, PART #840172, 75 ng/ml in reagent diluent) for 2 hours, washed again with PBST, and incubated with HRP-labeled streptavidin (R&D systems, PART #893975, 40-fold dilution using reagent diluent) for 20 mins. 1 ml of substrate solution (1:1 mixture of Color Reagent A ($H_2O_2$) and Color Reagent B (tetramethylbenzidine) (R&D Systems, Catalog #DY999)) was added to each well and the reaction was stopped by adding 500 µl of $H_2SO_4$ (2 N) (R&D Systems, Catalog #DY994) after 20 mins. Optical density of each well was determined immediately using a microplate reader set to 450 nm, after removing microneedle patch from each well. IL-6 ELISA on 96 well plate was implemented in the same manner.

Mouse IL-6 FLISA and p-FLISA on microneedle. Mouse IL-6 FLISA was implemented adopting the similar approach as the ELISA described above, except that HRP-labeled streptavidin was replaced by 800CW-labeled streptavidin (LI-COR P/N 926-32230, 20 ng/ml for 20 minutes). The patches were washed three times each using PBST followed by nanopure water. In case of p-FLISA, 1 ml plasmonic-fluor-800CW was added subsequently (extinction ~0.5), incubated for 30 minutes, and the patches were washed 3 times each with reagent diluent followed by PBST. Patches were imaged using Licor CLx fluorescence imager with the following scanning parameters: laser power~L2; resolution~21 µm; channel: 800; height: 0 mm.

Detection of Cocaine-Specific Antibody (IgG) in an Immunized Mouse Model

Animals and cocaine immunization. Male mice (C57BL/6, Jackson Lab #000664), at the age of 5-6 weeks, were purchased from Jackson Labs (Bar Harbor, ME, USA). Mice were housed four per cage and allowed to acclimate for 7 days before the experiment in the housing facility. Eleven mice were randomly divided into two groups, vaccination group and control group. For each mouse in vaccination group, cocaine vaccination solution including 100 g cocaine-BSA conjugate (Fitzgerald Industries, PART #80-1037) and 2 g lipopolysaccharide (InvivoGen, catalog code: vac-3pelps) in 100 l saline mixed with 100 l 2% Alhydrogel (InvivoGen, catalog code: vac-alu-250) was freshly prepared prior to vaccination. Each mouse was first vaccinated subcutaneously with totally 200 l of cocaine vaccine solution on four injection sites and boosted with half total dosage on two sites at day 14, 21 and 28, both on the dorsal side. Two weeks post last boost, blood from both vaccinated and control group was collected via the submandibular vein and serum was stored at −20° C.

Detection of anti-cocaine antibody in mouse serum. 96-well ELISA plates (Thermo Scientific, Catalog #15041) were coated with 1 g/ml BSA or cocaine-BSA conjugate in PBS at 4° C. overnight and blocked with 300 l of Odyssey® Blocking Buffer for 1 hour. Serum was diluted in PBST at a range of dilution in duplicates and applied on both BSA and cocaine-BSA conjugate coated wells for 1 hour at room temperature. After washing with PBST, plate was incubated with a biotin labeled donkey anti-mouse antibody (R&D systems, Catalog #BAF018, 1:2000 in 1% BSA-PBST, 100 µl per well) for another 1 hour, followed by HRP-labeled streptavidin (R&D systems, PART #893975, 40-fold dilution) for 20 mins. 100 l of substrate solution (1:1 mixture of Color Reagent A ($H_2O_2$) and Color Reagent B (tetramethylbenzidine) (R&D Systems, Catalog #DY999)) was added to each well and the reaction was stopped by 50 µl of $H_2SO_4$ (2 N) (R&D Systems, Catalog #DY994) and absorbance measured at 450 nm. Within vaccination group, anti-cocaine-BSA titer of each mouse was defined by three times of standard deviation plus its mean anti-BSA titer. Mice with higher anti-cocaine-BSA antibody titer than the anti-BSA titer were defined as "vaccine responders".

In Situ Sampling and Quantification of Cocaine Specific Antibody in Mouse Dermal ISF Through Microneedle Studying effect of administration time antibody detection. Microneedle patches were incubated with BSA (1 g/ml in PBS) in a 24-well plate at room temperature overnight, followed by washing and blocking with Odyssey® Blocking Buffer for 1 hour. After three times washing with PBST and blow drying with nitrogen gas, microneedle patches were administered on dorsal skin of mouse (vaccine responder) under anesthesia. The period of administration varied from 30 seconds to 5 minutes. Subsequently, patches were washed with PBST and blocked by Odyssey® Blocking Buffer for another 30 minutes, followed by incubation with biotin labeled donkey anti-mouse antibody (1:2000 in 1% BSA-PBST) for 1 hour and 800CW-labeled streptavidin (20 ng/ml) for 20 minutes. 1 ml Plasmonic-fluor-800CW (extinction ~0.5) was added subsequently, incubated for 30 minutes, and the patches were washed 3 times each with PBST. Patches were imaged using Licor CLx fluorescence imager with the following scanning parameters: laser power~L2; resolution~21 µm; channel: 800; height: 0 mm.

Studying effect of administration location for antibody detection. Eight microneedle patches were incubated with BSA (1 g/ml in PBS) in a 24-well plate at room temperature overnight, followed by washing and blocking with Odyssey® Blocking Buffer for 1 hour. After three times washing with PBST and blow drying with nitrogen gas, four microneedle patches were administered on dorsal skin and another four patches were administered on ventral skin of mice for 30 seconds, simultaneously. Subsequently, patches were washed with PBST and blocked by Odyssey® Blocking Buffer for another 30 minutes, followed by incubation with biotin labeled donkey anti-mouse antibody (1:2000 in 1% BSA-PBST) for 1 hour and 800CW-labeled streptavidin (20 ng/ml) for 20 minutes. 1 ml Plasmonic-fluor-800CW (extinction ~0.5) was added subsequently, incubated for 30 minutes, and the patches were washed 3 times each with PBST. Patches were imaged using Licor CLx fluorescence imager with the following scanning parameters: laser power~L2; resolution~21 µm; channel: 800; height: 0 mm.

Intensity of fluorescence signal represents the amount of anti-BSA antibody binding to the BSA on microneedle surface.

Detection of anti-cocaine antibody through microneedle. Microneedle patches were incubated with BSA or BSA-cocaine conjugate (1 g/ml in PBS) in a 24-well plate at room temperature overnight, followed by washing and blocking with Odyssey® Blocking Buffer for 1 hour. After washing and drying, two microneedle patches coated with BSA and BSA-cocaine conjugate were simultaneously administered on dorsal skin of mouse under anesthesia for 30 seconds. Subsequently, microneedle patches were washed and blocked, followed by incubation with anti-mouse antibody for 1 hour and 800CW-labeled streptavidin for 20 minutes. 1 ml plasmonic-fluor-800CW was added subsequently (extinction ~0.5) and incubated for 1 hour. Patches were imaged using LICOR CLx fluorescence imager using the same scanning parameters as stated above.

Detection and Quantification of Cytokines in an Endotoxin Shock Mouse Model

Animals and induction of endotoxin shock. Female mice (BALB/C, Jackson Lab #000651), at the age of 5-6 weeks, were purchased from Jackson Lab (Bar Harbor, ME, USA). Mice were housed three per cage and allowed to acclimate for 7 days in the housing facility before the microneedle experiment. To induce endotoxin shock, mice received intraperitoneal (i.p.) injection of lipopolysaccharide (InvivoGen, catalog code: vac-3pelps, 1 mg/kg mouse), while in control group mice received i.p. injection of saline solution.

In situ sampling and quantification of mouse IL-6 in dermal ISF through plasmonic-fluor enhanced microneedle. To sample IL-6 in mouse dermal ISF, microneedle patches were pre-functionalized with IL-6 capture antibody, followed by washing with PBST and blocking with reagent diluent (1×PBS containing 3% BSA, 0.2 µm filtered) for 1 hour. Microneedle patches were administered on mice ventral skin under anesthesia for 20 minutes for obtaining baseline IL-6 measurements. Subsequently, mice were injected with LPS and microneedle patches were administered on mice at 1, 2.5 and 4 hours after injection. Followed by additional 30 minutes blocking of reagent diluent (1×PBS containing 3% BSA, 0.2 µm filtered), microneedle patches were exposed to biotinylated detection antibody, streptavidin-800CW and plasmonic-fluor as described above. Fluorescence images of microneedle patches were obtained using LICOR CLx fluorescence imager using the same scanning parameters described above. Blood was collected via the submandibular vein right after the removal of microneedle patch at last time point (4 h post LPS injection) and serum was stored at −20° C. for further analysis. IL-6 ELISA was performed as previously described on 96 well microtiter plate to determine the concentration of IL-6 in mouse serum.

Detection and Quantification of Endogenous Matricellular Protein Periostin in Periosteum and Skin Animals. Periostin knockout mice and wild type littermate controls on a mixed B6; 129 background ($Postn^{tm1Jmol}$, Jackson Labs #009067) were a gift from Dr. Muhammad Farooq Rai (Department of Orthopedic Surgery, Washington University in St. Louis). Two wild type (WT) male and two periostin knockout ($Postn^{KO}$) male mice were used for the plasmonic-fluor enhanced microneedle detection of periostin at the age of 12 weeks.

Histology and Immunohistochemistry. The calvaria of wild type (WT) and periostin knockout ($Postn^{KO}$) mice were processed by Musculoskeletal Histology and Morphometry Core at Washington University in St. Louis for paraffin embedding, sectioning, and hematoxylin and eosin staining (H&E staining). Unstained tissue slides were acquired from the core for periostin immunostaining. Briefly, antigen retrieval was performed in sodium citrate buffer (10 mM sodium citrate, 0.05% Tween 20, pH 6.0) at 50-55° C. overnight. The tissues were then permeabilized in 0.2% Triton X-100 buffer (Sigma-Aldrich 9002-93-1) for 10 minutes, blocked in 2.5% normal horse serum (IMMPRESS HRP Anti-Rabbit IgG kit, Vector Laboratories, MP-7401) for 1 hour at room temperature, and incubated with anti-periostin antibody (Sigma-Aldrich HPA012306) with a dilution rate of 1:200 at 4° C. overnight. The endogenous peroxidase was quenched in 0.3% $H_2O_2$ for 30 minutes and the sections were incubated with biotinylated secondary antibody (IMMPRESS® HRP Anti-Rabbit IgG kit, Vector Laboratory, Catalog number, MP-7401-15) for 30 minutes at room temperature and the stain was developed by incubating with Metal Enhanced DAB Substrate (IMMPACT® DAB kit, Vector Laboratories, SK-4105). Nuclei were counter-stained with hematoxylin (Ricca chemical 3536-16). All washes between steps were performed in either double-distilled water or TNT buffer (0.1 M Tris-HCl, 0.15 M NaCl, 0.05 Tween).

In situ sampling and quantification of periostin in mouse periosteum and skin through plasmonic-fluor enhanced microneedle. Mouse periostin Duoset ELISA kit (R&D systems, catalog number DY2955, lot number P217047) was employed in the study. To sample periostin in mouse periosteum and dermal ISF, microneedle patches were pre-functionalized with periostin capture antibody (PART #842318) in a 24 well plate clamping on a magnetic plate separator, followed by washing with PBST and blocking with reagent diluent (1×PBS containing 3% BSA, 0.2 µm filtered). Skin above periosteum layer was carefully incised using scissors. A microneedle patch was administered on periosteum and another patch was administered on dorsal skin for 10 minutes, under anesthesia. Followed by another 30 minutes of blocking with reagent diluent (1×PBS containing 3% BSA, 0.2 µm filtered), microneedle patches were exposed to biotinylated detection antibody (PART #842319), streptavidin-800CW and plasmonic-fluor. Fluorescence maps of microneedle patches were imaged using LICOR CLx fluorescence imager using the same scanning parameters as described above. Blood was collected by cardiac puncture and serum was stored at −20° C. for further analysis. Periostin ELISA for mouse serum were implemented in similar approach on 96 well microtiter plate.

Statistics. For analyzing the statistical difference between two groups, an unpaired one-tailed t-test with Welch's correction was used. For analyzing the statistical difference between each data point in two groups, the two-way analysis of variance (ANOVA) with Sidak's multiple-comparison test was used. For analyzing the statistical difference between two or more groups, the one-way analysis of variance (ANOVA) with Tukey's multiple-comparison test was used. Statistical significance of the data was calculated at 95% ($P<0.05$) confidence intervals. All values are expressed as mean±s.d. GraphPad Prism 8 was used for all statistical analysis. Four-parameter logistic or polynomial fit was employed to calculate the LOD in the standard curves of bioassays. The LOD is defined as the analyte concentration corresponding to the mean fluorescence intensity of blank plus three times of its standard deviation (mean+3σ). Origin 2016 was employed for calculating the LOD.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

Any non-limiting examples are provided to further illustrate the present disclosure. It should be appreciated by those of skill in the art that the techniques disclosed in the examples represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

What is claimed is:

1. A bilayered microneedle patch comprising:
   a magnetic backing layer, wherein the magnetic backing layer comprises at least one magnetic nanoparticle; and
   a microneedle layer attached to the magnetic backing layer, wherein the microneedle layer comprises an array of microneedles.

2. The microneedle patch of claim 1, wherein each microneedle of the array of microneedles is coated with a plurality of capture biorecognition elements.

3. The microneedle patch of claim 1, wherein the microneedle layer comprises at least one of polystyrene, polyvinyl chloride, polypropylene, and cycloolefin.

4. The microneedle patch of claim 1, wherein the magnetic backing layer comprises a mixture of at least one polymer and at least one magnetic nanoparticle, wherein the polymers are selected from the group consisting of polystyrene, polyvinyl chloride, polypropylene, cycloolefin and the magnetic nanoparticles are selected from the group consisting of iron-containing magnetic materials, nickel-containing magnetic materials and cobalt-containing magnetic materials.

5. The microneedle patch of claim 1, wherein the array of microneedles has a center-to-center spacing of at least about 100 μm between microneedles.

6. An assay for detection of a target interstitial fluid (ISF) analyte, the assay comprising:
   a microneedle patch comprising a magnetic backing layer and a microneedle layer attached to the magnetic backing layer, wherein the microneedle layer comprises an array of microneedles coated with a plurality of capture biorecognition elements;
   a plurality of detection biorecognition elements; and
   a plurality of fluorescent labels comprising a plasmonic-fluor.

7. The assay of claim 6, wherein the plurality of detection biorecognition elements comprises biotin.

8. The assay of claim 6, wherein the plurality of fluorescent labels further comprise streptavidin.

9. The assay of claim 6, wherein the target ISF analyte is selected from the group consisting of a protein biomarker comprising a pro-inflammatory cytokine, an antibody in response to a bacterial infection, an antibody in response to a viral infection, an antibody in response to a vaccination, a biomarker, and a small molecule.

10. The assay of claim 9, wherein the pro-inflammatory cytokine is mouse interleukin 6 (IL-6).

11. The assay of claim 6, wherein the plurality of capture biorecognition elements comprises periostin.

12. The assay of claim 6, wherein the microneedle layer comprises at least one of polystyrene, polyvinyl chloride, polypropylene, and cycloolefin.

13. The assay of claim 6, wherein the magnetic backing layer comprises a mixture of at least one polymer and at least one magnetic nanoparticle, wherein the polymers are selected from the group consisting of polystyrene, polyvinyl chloride, polypropylene, cycloolefin and the magnetic nanoparticles are selected from the group consisting of iron-containing magnetic materials, nickel-containing magnetic materials and cobalt-containing magnetic materials.

14. The assay of claim 6, wherein the array of microneedles has a center-to-center spacing of at least about 100 μm between microneedles.

15. A method for detecting a target interstitial fluid (ISF) analyte comprising:

administering a microneedle patch to penetrate a dermal layer of a subject and sample the ISF of the subject, wherein the microneedle patch comprises a magnetic backing layer and a microneedle layer attached to the magnetic backing layer, wherein the microneedle layer comprises an array of microneedles coated with a plurality of capture biorecognition elements;

removing the microneedle patch from the dermal layer of the subject;

adding a plurality of detection biorecognition elements to the microneedle patch;

adding a plurality of fluorescent labels to the microneedle patch, wherein each of the plurality of fluorescent labels comprises a plasmonic-fluor; and detecting the target ISF analyte based on a fluorescence signal from the plasmonic-fluor.

16. The method of claim 15, wherein the plurality of detection biorecognition elements comprises biotin.

17. The method of claim 15, wherein the plurality of fluorescent labels further comprise streptavidin.

18. The method of claim 15, wherein the target ISF analyte is selected from the group consisting of a protein biomarker comprising a pro-inflammatory cytokine, an antibody in response to a bacterial infection, an antibody in response to a viral infection, an antibody in response to a vaccination, a biomarker, and a small molecule.

19. The method of claim 18, wherein the pro-inflammatory cytokine is mouse interleukin 6 (IL-6).

20. The method of claim 15, wherein the plurality of capture biorecognition elements comprises periostin.

* * * * *